(12) United States Patent
Cosman

(10) Patent No.: US 7,014,853 B2
(45) Date of Patent: Mar. 21, 2006

(54) FAMILY OF IMMUNOREGULATORS DESIGNATED LEUKOCYTE IMMUNOGLOBULIN-LIKE RECEPTORS (LIR)

(75) Inventor: David J. Cosman, Bainbridge Island, WA (US)

(73) Assignee: Immunex Corporation, Seattle, WA (US)

(*) Notice: Subject to any disclaimer, the term of this patent is extended or adjusted under 35 U.S.C. 154(b) by 0 days.

(21) Appl. No.: 10/143,618

(22) Filed: May 8, 2002

(65) Prior Publication Data
US 2003/0166073 A1 Sep. 4, 2003

Related U.S. Application Data

(63) Continuation of application No. 08/842,248, filed on Apr. 24, 1997, now Pat. No. 6,448,035.

(51) Int. Cl.
*A61K 39/395* (2006.01)
*C07K 16/00* (2006.01)
*C12P 21/08* (2006.01)

(52) U.S. Cl. ............................... 424/135.1; 424/141.1; 530/387.9; 530/389.1; 530/388.1

(58) Field of Classification Search ............. 530/389.1, 530/387.1, 388.1; 424/139.1, 141.1, 130.1
See application file for complete search history.

(56) References Cited

U.S. PATENT DOCUMENTS 6,140,076 A * 10/2000 Adema et al.
6,448,035 B1    9/2002 Cosman (Continued)

FOREIGN PATENT DOCUMENTS

| WO | WO 98/09638 | 3/1998 |
| WO | WO 98/24906 | 6/1998 |
| WO | WO 98/31806 | 7/1998 |

OTHER PUBLICATIONS

Samaridis, J. et al., "Cloning of novel immunoglobulin superfamily receptors expressed on human myeloid and lymphoid cells: structural evidence for new stimulatory and inhibitory pathways," *Eur. J. Immunol.* 27:660–665, 1997.
Rojo, S. et al., "Type I Transmembrane Receptor with Inhibitory Function in Mouse Mast Cells and NK Cells," *J. Immunol.* 158 (*1*):9–12, 1997.
Hayami et al., "Molecular Cloning of a Novel Murine Cell-surface Glycoprotein Homologous to Killer Cell Inhibitory Receptors," *J of Bio Chem* 272:7320–7327, Mar. 1999.
Kubagawa et al., "A novel pair of immunoglobulin–like receptors expressed by B cells and myeloid cells," *Proc. Natl. Acad. Sci ISA* 94:5261–5266, May 1997.
Cella et al., "A novel Inhibitory Receptor (ILT3) Expressed on Monocyates, Macrophages, and Dendritic Cells Involved in Antigen Processing," *J Exp. Med.* 1185(10): 1743–1751.
Colonna et al., "Cloning of Immunoglobulin–Superfamily Members Associated with HLA–C and HLA–B Recognition by Human Natural Killer Cells," *Science* 268:405–408, Apr. 1995.
Moretta et al., "Existence of Both Inhibitory (p58) and Activatory (p50) Receptors for HLA–C Molecules in Human Natural Killer Cells," *J Exp. Med.* 182:875–884, Sep. 1995.
Katz et al., Mouse mast cell gp49B1 contains two immunoreceptor tyrosine–based inhibition motifs and suppresses mast cell activation when coligated with the high–affinity Fc receptor or IGE, *Proc. Natl. Acad. Sci USA* 93:10809–10814, Oct. 1996.
Biassoni et al., "The Human Leukocyte Antigen (HLA)–C–specific 'Activatory' or 'Inhibitory' Natural Killer Cell Receptors Display Highly Homologous Extracellular Domains but Differ in their Transmembrane and Intracytoplasmic Portions," *J Exp Med* 183:645–640, Feb. 1996.
Burshtyn et al., "Recruitment of Tyrosine Phosphatase HCP by the Killer Cell Inhibitory Receptor," *Immunity* 4:77–85, Jan. 1996/.
Fry et al., "Phosphotyrosines in the Killer Cell Inhibitory Receptor Motif of NKB1 are Required for Negative Signaling and for Association with Protein Tyrosine Phosphatase 1C," *Exp Med* 184:295–300, Jul. 1996.
Lanier et al., "Inhibitory MHC class I receptors NK cells and T cells," *Immunology Today*, Feb. 1996.
Imboden J., "Inate immunity: Turning off natural killers," *Current Biology* 6(9):1070–1072, 1996.
Arm, J. et al., "Molecular Identification of a Novel Family of Human Ig Superfamily Members That Possess Immunoreceptor Tyrosine–Based Inhibition Motifs and Homology to the Mouse gp49B1 Inhibitory Receptor," *J. Immunol.* 159 (*5*):2342–2349, 1997.

(Continued)

*Primary Examiner*—Christina Chan
*Assistant Examiner*—Michail Belyavskyi
(74) *Attorney, Agent, or Firm*—Paul B.. Tran; Ron Levy; Stuart L. Watt

(57) ABSTRACT

A new family of immunoreceptor molecules of the immunoglobulin superfamily, (LIR) polypeptides is described. Disclosed are sequences encoding LIR family members and their deduced amino acid sequences, polypeptides encoded by DNA that hybridize to oligonucleotide probes having defined sequences, processes for producing polypeptides of the LIR family, and antagonistic antibodies to LIR family members. LIR family members can be used to treat autoimmune diseases and disease states associated with suppressed immune function.

9 Claims, No Drawings

U.S. PATENT DOCUMENTS 6,479,638 B1 11/2002 Adema et al.
2003/0105303 A1 6/2003 Adema et al.

OTHER PUBLICATIONS

Cosman, D. et al., "A Novel Immunoglobulin superfamily Receptor for Cellular and Viral MHC Class I Molecules," *Immunity* 7:273–282, 1997.

Borges, L. et al., "A Family of Human Lymphoid and Myeloid Ig–Like Receptors, Some of Which Bind to MHC Class I Molecules," *J. Immunol.* 159 (11):5192–5196, 1997.

Lewis L. Lanier, "Natural killer cell receptors and MHC class I Interactions," 9 (1):126–131, 1997.

Samaridis J and Colonna M., GenBank Accession No. U82279, Mar. 27, 1997; also disclosed in: "Cloning of novel immunoglobulin superfamily receptors expressed on human mycloid and lumphoid cells: structural evidence for new stimulatory and inhibitory pathways" *Eur J Immunol* 27:660–665, 1997.

Hillier L. et al., GenBank Accession No. 95687, Apr. 9, 1996.

Naeve CW et al., "Accuracy of automated DNA sequencing; a multilaboratory comparision of sequencing results," *Biotechniques* 19(3):448–452, 1995.

* cited by examiner

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 2922 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (vi) ORIGINAL SOURCE:
      (A) ORGANISM: Leukocyte Immunoglobulin Receptor P3G2

(ix) FEATURE:
      (A) NAME/KEY: CDS
      (B) LOCATION: 310..2259

(xi) SEQUENCE DESCRIPTION: SEQ ID NO: 1:

```
AGGGCCACGC GTGCATGCGT CGACTGGAAC GAGACGACCT GCTGTGACCC CCTTGTGGGC    60

ACTCCATTGG TTTTATGGCG CCTCTACTTT CTGGAGTTTG TGTAAAACAA AAATATTATG   120

GTCTTTGTGC ACATTTACAT CAAGCTCAGC CTGGGCGGCA CAGCCAGATG CGAGATGCGT   180

CTCTGCTGAT CTGAGTCTGC CTGCAGCATG GACCTGGGTC TTCCCTGAAG CATCTCCAGG   240

GCTGGAGGGA CGACTGCCAT GCACCGAGGG CTCATCCATC CACAGAGCAG GGCAGTGGGA   300

GGAGACGCC ATG ACC CCC ATC CTC ACG GTC CTG ATC TGT CTC GGG CTG       348
           Met Thr Pro Ile Leu Thr Val Leu Ile Cys Leu Gly Leu
             1               5                  10

AGT CTG GGC CCC CGG ACC CAC GTG CAG GCA GGG CAC CTC CCC AAG CCC    396
Ser Leu Gly Pro Arg Thr His Val Gln Ala Gly His Leu Pro Lys Pro
    15                  20                  25

ACC CTC TGG GCT GAA CCA GGC TCT GTG ATC ACC CAG GGG AGT CCT GTG    444
Thr Leu Trp Ala Glu Pro Gly Ser Val Ile Thr Gln Gly Ser Pro Val
 30                  35                  40                  45

ACC CTC AGG TGT CAG GGG GGC CAG GAG ACC CAG GAG TAC CGT CTA TAT    492
Thr Leu Arg Cys Gln Gly Gly Gln Glu Thr Gln Glu Tyr Arg Leu Tyr
                 50                  55                  60

AGA GAA AAG AAA ACA GCA CCC TGG ATT ACA CGG ATC CCA CAG GAG CTT    540
Arg Glu Lys Lys Thr Ala Pro Trp Ile Thr Arg Ile Pro Gln Glu Leu
             65                  70                  75

GTG AAG AAG GGC CAG TTC CCC ATC CCA TCC ATC ACC TGG GAA CAT GCA    588
Val Lys Lys Gly Gln Phe Pro Ile Pro Ser Ile Thr Trp Glu His Ala
         80                  85                  90

GGG CGG TAT CGC TGT TAC TAT GGT AGC GAC ACT GCA GGC CGC TCA GAG    636
Gly Arg Tyr Arg Cys Tyr Tyr Gly Ser Asp Thr Ala Gly Arg Ser Glu
     95                 100                 105

AGC AGT GAC CCC CTG GAG CTG GTG GTG ACA GGA GCC TAC ATC AAA CCC    684
Ser Ser Asp Pro Leu Glu Leu Val Val Thr Gly Ala Tyr Ile Lys Pro
110                 115                 120                 125
```

-continued

```
ACC CTC TCA GCC CAG CCC AGC CCC GTG GTG AAC TCA GGA GGG AAT GTA    732
Thr Leu Ser Ala Gln Pro Ser Pro Val Val Asn Ser Gly Gly Asn Val
            130                 135                 140

ACC CTC CAG TGT GAC TCA CAG GTG GCA TTT GAT GGC TTC ATT CTG TGT    780
Thr Leu Gln Cys Asp Ser Gln Val Ala Phe Asp Gly Phe Ile Leu Cys
            145                 150                 155

AAG GAA GGA GAA GAT GAA CAC CCA CAA TGC CTG AAC TCC CAG CCC CAT    828
Lys Glu Gly Glu Asp Glu His Pro Gln Cys Leu Asn Ser Gln Pro His
            160                 165                 170

GCC CGT GGG TCG TCC CGC GCC ATC TTC TCC GTG GGC CCC GTG AGC CCG    876
Ala Arg Gly Ser Ser Arg Ala Ile Phe Ser Val Gly Pro Val Ser Pro
175                 180                 185

AGT CGC AGG TGG TGG TAC AGG TGC TAT GCT TAT GAC TCG AAC TCT CCC    924
Ser Arg Arg Trp Trp Tyr Arg Cys Tyr Ala Tyr Asp Ser Asn Ser Pro
190                 195                 200                 205

TAT GAG TGG TCT CTA CCC AGT GAT CTC CTG GAG CTC CTG GTC CTA GGT    972
Tyr Glu Trp Ser Leu Pro Ser Asp Leu Leu Glu Leu Leu Val Leu Gly
                210                 215                 220

GTT TCT AAG AAG CCA TCA CTC TCA GTG CAG CCA GGT CCT ATC GTG GCC    1020
Val Ser Lys Lys Pro Ser Leu Ser Val Gln Pro Gly Pro Ile Val Ala
                225                 230                 235

CCT GAG GAG ACC CTG ACT CTG CAG TGT GGC TCT GAT GCT GGC TAC AAC    1068
Pro Glu Glu Thr Leu Thr Leu Gln Cys Gly Ser Asp Ala Gly Tyr Asn
            240                 245                 250

AGA TTT GTT CTG TAT AAG GAC GGG GAA CGT GAC TTC CTT CAG CTC GCT    1116
Arg Phe Val Leu Tyr Lys Asp Gly Glu Arg Asp Phe Leu Gln Leu Ala
            255                 260                 265

GGC GCA CAG CCC CAG GCT GGG CTC TCC CAG GCC AAC TTC ACC CTG GGC    1164
Gly Ala Gln Pro Gln Ala Gly Leu Ser Gln Ala Asn Phe Thr Leu Gly
270                 275                 280                 285

CCT GTG AGC CGC TCC TAC GGG GGC CAG TAC AGA TGC TAC GGT GCA CAC    1212
Pro Val Ser Arg Ser Tyr Gly Gly Gln Tyr Arg Cys Tyr Gly Ala His
                290                 295                 300

AAC CTC TCC TCC GAG TGG TCG GCC CCC AGC GAC CCC CTG GAC ATC CTG    1260
Asn Leu Ser Ser Glu Trp Ser Ala Pro Ser Asp Pro Leu Asp Ile Leu
                305                 310                 315

ATC GCA GGA CAG TTC TAT GAC AGA GTC TCC CTC TCG GTG CAG CCG GGC    1308
Ile Ala Gly Gln Phe Tyr Asp Arg Val Ser Leu Ser Val Gln Pro Gly
            320                 325                 330

CCC ACG GTG GCC TCA GGA GAG AAC GTG ACC CTG CTG TGT CAG TCA CAG    1356
Pro Thr Val Ala Ser Gly Glu Asn Val Thr Leu Leu Cys Gln Ser Gln
            335                 340                 345

GGA TGG ATG CAA ACT TTC CTT CTG ACC AAG GAG GGG GCA GCT GAT GAC    1404
Gly Trp Met Gln Thr Phe Leu Leu Thr Lys Glu Gly Ala Ala Asp Asp
350                 355                 360                 365

CCA TGG CGT CTA AGA TCA ACG TAC CAA TCT CAA AAA TAC CAG GCT GAA    1452
Pro Trp Arg Leu Arg Ser Thr Tyr Gln Ser Gln Lys Tyr Gln Ala Glu
                370                 375                 380

TTC CCC ATG GGT CCT GTG ACC TCA GCC CAT GCG GGG ACC TAC AGG TGC    1500
Phe Pro Met Gly Pro Val Thr Ser Ala His Ala Gly Thr Tyr Arg Cys
                385                 390                 395

TAC GGC TCA CAG AGC TCC AAA CCC TAC CTG CTG ACT CAC CCC AGT GAC    1548
Tyr Gly Ser Gln Ser Ser Lys Pro Tyr Leu Leu Thr His Pro Ser Asp
            400                 405                 410

CCC CTG GAG CTC GTG GTC TCA GGA CCG TCT GGG GGC CCC AGC TCC CCG    1596
Pro Leu Glu Leu Val Val Ser Gly Pro Ser Gly Gly Pro Ser Ser Pro
            415                 420                 425

ACA ACA GGC CCC ACC TCC ACA TCT GGC CCT GAG GAC CAG CCC CTC ACC    1644
Thr Thr Gly Pro Thr Ser Thr Ser Gly Pro Glu Asp Gln Pro Leu Thr
```

```
     430              435              440              445
CCC ACC GGG TCG GAT CCC CAG AGT GGT CTG GGA AGG CAC CTG GGG GTT    1692
Pro Thr Gly Ser Asp Pro Gln Ser Gly Leu Gly Arg His Leu Gly Val
                450              455              460

GTG ATC GGC ATC TTG GTG GCC GTC ATC CTA CTG CTC CTC CTC CTC CTC    1740
Val Ile Gly Ile Leu Val Ala Val Ile Leu Leu Leu Leu Leu Leu Leu
            465              470              475

CTC CTC TTC CTC ATC CTC CGA CAT CGA CGT CAG GGC AAA CAC TGG ACA    1788
Leu Leu Phe Leu Ile Leu Arg His Arg Arg Gln Gly Lys His Trp Thr
        480              485              490

TCG ACC CAG AGA AAG GCT GAT TTC CAA CAT CCT GCA GGG GCT GTG GGG    1836
Ser Thr Gln Arg Lys Ala Asp Phe Gln His Pro Ala Gly Ala Val Gly
    495              500              505

CCA GAG CCC ACA GAC AGA GGC CTG CAG TGG AGG TCC AGC CCA GCT GCC    1884
Pro Glu Pro Thr Asp Arg Gly Leu Gln Trp Arg Ser Ser Pro Ala Ala
510              515              520              525

GAT GCC CAG GAA GAA AAC CTC TAT GCT GCC GTG AAG CAC ACA CAG CCT    1932
Asp Ala Gln Glu Glu Asn Leu Tyr Ala Ala Val Lys His Thr Gln Pro
            530              535              540

GAG GAT GGG GTG GAG ATG GAC ACT CGG AGC CCA CAC GAT GAA GAC CCC    1980
Glu Asp Gly Val Glu Met Asp Thr Arg Ser Pro His Asp Glu Asp Pro
        545              550              555

CAG GCA GTG ACG TAT GCC GAG GTG AAA CAC TCC AGA CCT AGG AGA GAA    2028
Gln Ala Val Thr Tyr Ala Glu Val Lys His Ser Arg Pro Arg Arg Glu
    560              565              570

ATG GCC TCT CCT CCT TCC CCA CTG TCT GGG GAA TTC CTG GAC ACA AAG    2076
Met Ala Ser Pro Pro Ser Pro Leu Ser Gly Glu Phe Leu Asp Thr Lys
575              580              585

GAC AGA CAG GCG GAA GAG GAC AGG CAG ATG GAC ACT GAG GCT GCT GCA    2124
Asp Arg Gln Ala Glu Glu Asp Arg Gln Met Asp Thr Glu Ala Ala Ala
590              595              600              605

TCT GAA GCC CCC CAG GAT GTG ACC TAC GCC CAG CTG CAC AGC TTG ACC    2172
Ser Glu Ala Pro Gln Asp Val Thr Tyr Ala Gln Leu His Ser Leu Thr
            610              615              620

CTT AGA CGG AAG GCA ACT GAG CCT CCT CCA TCC CAG GAA GGG CCC TCT    2220
Leu Arg Arg Lys Ala Thr Glu Pro Pro Pro Ser Gln Glu Gly Pro Ser
        625              630              635

CCA GCT GTG CCC AGC ATC TAC GCC ACT CTG GCC ATC CAC TAG             2262
Pro Ala Val Pro Ser Ile Tyr Ala Thr Leu Ala Ile His
    640              645              650

CCCAGGGGGG GACGCAGACC CCACACTCCA TGGAGTCTGG AATGCATGGG AGCTGCCCCC    2322

CCAGTGGACA CCATTGGACC CCACCCAGCC TGGATCTACC CCAGGAGACT CTGGGAACTT    2382

TTAGGGGTCA CTCAATTCTG CAGTATAAAT AACTAATGTC TCTACAATTT TGAAATAAAG    2442

CAACAGACTT CTCAATAATC AATGAAGTAG CTGAGAAAAC TAAGTCAGAA AGTGCATTAA    2502

ACTGAATCAC AATGTAAATA TTACACATCA AGCGATGAAA CTGGAAAACT ACAAGCCACG    2562

AATGAATGAA TTAGGAAAGA AAAAAGTAG GAAATGAATG ATCTTGGCTT TCCTATAAGA    2622

AATTTAGGGC AGGGCACGGT GGCTCACGCC TGTAATTCCA GCACTTTGGG AGGCCGAGGC    2682

GGGCAGATCA CGAGTTCAGG AGATCGAGAC CATCTTGGCC AACATGGTGA AACCCTGTCT    2742

CTCCTAAAAA TACAAAAATT AGCTGGATGT GGTGGCAGTG CCTGTAATCC CAGCTATTTG    2802

GGAGGCTGAG GCAGGAGAAT CGCTTGAACC AGGGAGTCAG AGGTTTCAGT GAGCCAAGAT    2862

CGCACCACTG CTCTCCAGCC TGGCGACAAG CAGGTCGTCT CGTTCCAGTC GACGGCCCAT    2922
```

(2) INFORMATION FOR SEQ ID NO: 2:

(i) SEQUENCE CHARACTERISTICS:
    (A) LENGTH: 650 amino acids
    (B) TYPE: amino acid
    (D) TOPOLOGY: linear (ii) MOLECULE TYPE: protein (xi) SEQUENCE DESCRIPTION: SEQ ID NO: 2:

Met Thr Pro Ile Leu Thr Val Leu Ile Cys Leu Gly Leu Ser Leu Gly
 1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
            85                  90                  95

Arg Cys Tyr Tyr Gly Ser Asp Thr Ala Gly Arg Ser Glu Ser Ser Asp
        100                 105                 110

Pro Leu Glu Leu Val Val Thr Gly Ala Tyr Ile Lys Pro Thr Leu Ser
    115                 120                 125

Ala Gln Pro Ser Pro Val Val Asn Ser Gly Gly Asn Val Thr Leu Gln
130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
            165                 170                 175

Ser Ser Arg Ala Ile Phe Ser Val Gly Pro Val Ser Pro Ser Arg Arg
        180                 185                 190

Trp Trp Tyr Arg Cys Tyr Ala Tyr Asp Ser Asn Ser Pro Tyr Glu Trp
    195                 200                 205

Ser Leu Pro Ser Asp Leu Leu Glu Leu Leu Val Leu Gly Val Ser Lys
210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
            245                 250                 255

Leu Tyr Lys Asp Gly Glu Arg Asp Phe Leu Gln Leu Ala Gly Ala Gln
        260                 265                 270

Pro Gln Ala Gly Leu Ser Gln Ala Asn Phe Thr Leu Gly Pro Val Ser
    275                 280                 285

Arg Ser Tyr Gly Gly Gln Tyr Arg Cys Tyr Gly Ala His Asn Leu Ser
290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
            325                 330                 335

Ala Ser Gly Glu Asn Val Thr Leu Leu Cys Gln Ser Gln Gly Trp Met
        340                 345                 350

Gln Thr Phe Leu Leu Thr Lys Glu Gly Ala Ala Asp Asp Pro Trp Arg
    355                 360                 365

Leu Arg Ser Thr Tyr Gln Ser Gln Lys Tyr Gln Ala Glu Phe Pro Met

```
            370                 375                 380
Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
                420                 425                 430

Pro Thr Ser Thr Ser Gly Pro Glu Asp Gln Pro Leu Thr Pro Thr Gly
                435                 440                 445

Ser Asp Pro Gln Ser Gly Leu Gly Arg His Leu Gly Val Val Ile Gly
450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys His Thr Gln Pro Glu Asp Gly
530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
                580                 585                 590

Ala Glu Glu Asp Arg Gln Met Asp Thr Glu Ala Ala Ser Glu Ala
                595                 600                 605

Pro Gln Asp Val Thr Tyr Ala Gln Leu His Ser Leu Thr Leu Arg Arg
                610                 615                 620

Lys Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650

(2) INFORMATION FOR SEQ ID NO: 3:

(i) SEQUENCE CHARACTERISTICS:
        (A) LENGTH: 2777 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: 18a3

(ix) FEATURE:
        (A) NAME/KEY: CDS
        (B) LOCATION: 168..2123

(xi) SEQUENCE DESCRIPTION: SEQ ID NO: 3:

AGCTCAGCCT GGGCGGCACA GCCAGATGCG AGATGCGTCT CTGCTGATCT GAGTCTGCCT      60

GCAGCATGGA CCTGGGTCTT CCCTGAAGCA TCTCCAGGGC TGGAGGGACG ACTGCCATGC     120

ACCGAGGGCT CATCCATCCA CAGAGCAGGG CAGTGGGAGG AGACGCC ATG ACC CCC       176
                                                 Met Thr Pro
```

```
ATC CTC ACG GTC CTG ATC TGT CTC GGG CTG AGT CTG GGC CCC AGG ACC      224
Ile Leu Thr Val Leu Ile Cys Leu Gly Leu Ser Leu Gly Pro Arg Thr
     5              10                  15

CAC GTG CAG GCA GGG CAC CTC CCC AAG CCC ACC CTC TGG GCT GAA CCA      272
His Val Gln Ala Gly His Leu Pro Lys Pro Thr Leu Trp Ala Glu Pro
 20              25                  30                  35

GGC TCT GTG ATC ACC CAG GGG AGT CCT GTG ACC CTC AGG TGT CAG GGG      320
Gly Ser Val Ile Thr Gln Gly Ser Pro Val Thr Leu Arg Cys Gln Gly
                 40                  45                  50

GGC CAG GAG ACC CAG GAG TAC CGT CTA TAT AGA GAA AAG AAA ACA GCA      368
Gly Gln Glu Thr Gln Glu Tyr Arg Leu Tyr Arg Glu Lys Lys Thr Ala
             55                  60                  65

CTC TGG ATT ACA CGG ATC CCA CAG GAG CTT GTG AAG AAG GGC CAG TTC      416
Leu Trp Ile Thr Arg Ile Pro Gln Glu Leu Val Lys Lys Gly Gln Phe
         70                  75                  80

CCC ATC CCA TCC ATC ACC TGG GAA CAT GCA GGG CGG TAT CGC TGT TAC      464
Pro Ile Pro Ser Ile Thr Trp Glu His Ala Gly Arg Tyr Arg Cys Tyr
     85                  90                  95

TAT GGT AGC GAC ACT GCA GGC CGC TCA GAG AGC AGT GAC CCC CTG GAG      512
Tyr Gly Ser Asp Thr Ala Gly Arg Ser Glu Ser Ser Asp Pro Leu Glu
100                 105                 110                 115

CTG GTG GTG ACA GGA GCC TAC ATC AAA CCC ACC CTC TCA GCC CAG CCC      560
Leu Val Val Thr Gly Ala Tyr Ile Lys Pro Thr Leu Ser Ala Gln Pro
                 120                 125                 130

AGC CCC GTG GTG AAC TCA GGA GGG AAT GTA ATC CTC CAG TGT GAC TCA      608
Ser Pro Val Val Asn Ser Gly Gly Asn Val Ile Leu Gln Cys Asp Ser
             135                 140                 145

CAG GTG GCA TTT GAT GGC TTC AGT CTG TGT AAG GAA GGA GAA GAT GAA      656
Gln Val Ala Phe Asp Gly Phe Ser Leu Cys Lys Glu Gly Glu Asp Glu
         150                 155                 160

CAC CCA CAA TGC CTG AAC TCC CAG CCC CAT GCC CGT GGG TCG TCC CGC      704
His Pro Gln Cys Leu Asn Ser Gln Pro His Ala Arg Gly Ser Ser Arg
     165                 170                 175

GCC ATC TTC TCC GTG GGC CCC GTG AGC CCG AGT CGC AGG TGG TGG TAC      752
Ala Ile Phe Ser Val Gly Pro Val Ser Pro Ser Arg Arg Trp Trp Tyr
180                 185                 190                 195

AGG TGC TAT GCT TAT GAC TCG AAC TCT CCC TAT GAG TGG TCT CTA CCC      800
Arg Cys Tyr Ala Tyr Asp Ser Asn Ser Pro Tyr Glu Trp Ser Leu Pro
                 200                 205                 210

AGT GAT CTC CTG GAG CTC CTG GTC CTA GGT GTT TCT AAG AAG CCA TCA      848
Ser Asp Leu Leu Glu Leu Leu Val Leu Gly Val Ser Lys Lys Pro Ser
             215                 220                 225

CTC TCA GTG CAG CCA GGT CCT ATC GTG GCC CCT GAG GAG ACC CTG ACT      896
Leu Ser Val Gln Pro Gly Pro Ile Val Ala Pro Glu Glu Thr Leu Thr
         230                 235                 240

CTG CAG TGT GGC TCT GAT GCT GGC TAC AAC AGA TTT GTT CTG TAT AAG      944
Leu Gln Cys Gly Ser Asp Ala Gly Tyr Asn Arg Phe Val Leu Tyr Lys
     245                 250                 255

GAC GGG GAA CGT GAC TTC CTT CAG CTC GCT GGC GCA CAG CCC CAG GCT      992
Asp Gly Glu Arg Asp Phe Leu Gln Leu Ala Gly Ala Gln Pro Gln Ala
260                 265                 270                 275

GGG CTC TCC CAG GCC AAC TTC ACC CTG GGC CCT GTG AGC CGC TCC TAC     1040
Gly Leu Ser Gln Ala Asn Phe Thr Leu Gly Pro Val Ser Arg Ser Tyr
                 280                 285                 290

GGG GGC CAG TAC AGA TGC TAC GGT GCA CAC AAC CTC TCC TCC GAG TGG     1088
Gly Gly Gln Tyr Arg Cys Tyr Gly Ala His Asn Leu Ser Ser Glu Trp
             295                 300                 305

TCG GCC CCC AGT GAC CCC CTG GAC ATC CTG ATC GCA GGA CAG TTC TAT     1136
Ser Ala Pro Ser Asp Pro Leu Asp Ile Leu Ile Ala Gly Gln Phe Tyr
```

```
                                        -continued

Ser Ala Pro Ser Asp Pro Leu Asp Ile Leu Ile Ala Gly Gln Phe Tyr
        310                 315                 320

GAC AGA GTC TCC CTC TCG GTG CAG CCG GGC CCC ACG GTG GCC TCA GGA      1184
Asp Arg Val Ser Leu Ser Val Gln Pro Gly Pro Thr Val Ala Ser Gly
325                 330                 335

GAG AAC GTG ACC CTG CTG TGT CAG TCA CAG GGA TGG ATG CAA ACT TTC      1232
Glu Asn Val Thr Leu Leu Cys Gln Ser Gln Gly Trp Met Gln Thr Phe
340                 345                 350                 355

CTT CTG ACC AAG GAG GGG GCA GCT GAT GAC CCA TGG CGT CTA AGA TCA      1280
Leu Leu Thr Lys Glu Gly Ala Ala Asp Asp Pro Trp Arg Leu Arg Ser
                360                 365                 370

ACG TAC CAA TCT CAA AAA TAC CAG GCT GAA TTC CCC ATG GGT CCT GTG      1328
Thr Tyr Gln Ser Gln Lys Tyr Gln Ala Glu Phe Pro Met Gly Pro Val
            375                 380                 385

ACC TCA GCC CAT GCG GGG ACC TAC AGG TGC TAC GGC TCA CAG AGC TCC      1376
Thr Ser Ala His Ala Gly Thr Tyr Arg Cys Tyr Gly Ser Gln Ser Ser
        390                 395                 400

AAA CCC TAC CTG CTG ACT CAC CCC AGT GAC CCC CTG GAG CTC GTG GTC      1424
Lys Pro Tyr Leu Leu Thr His Pro Ser Asp Pro Leu Glu Leu Val Val
405                 410                 415

TCA GGA CCG TCT GGG GGC CCC AGC TCC CCG ACA ACA GGC CCC ACC TCC      1472
Ser Gly Pro Ser Gly Gly Pro Ser Ser Pro Thr Thr Gly Pro Thr Ser
420                 425                 430                 435

ACA TCT GCA GGC CCT GAG GAC CAG CCC CTC ACC CCC ACC GGG TCG GAT      1520
Thr Ser Ala Gly Pro Glu Asp Gln Pro Leu Thr Pro Thr Gly Ser Asp
                440                 445                 450

CCC CAG AGT GGT CTG GGA AGG CAC CTG GGG GTT GTG ATC GGC ATC TTG      1568
Pro Gln Ser Gly Leu Gly Arg His Leu Gly Val Val Ile Gly Ile Leu
            455                 460                 465

GTG GCC GTC ATC CTA CTG CTC CTC CTC CTC CTC CTC TTC CTC ATC          1616
Val Ala Val Ile Leu Leu Leu Leu Leu Leu Leu Leu Phe Leu Ile
        470                 475                 480

CTC CGA CAT CGA CGT CAG GGC AAA CAC TGG ACA TCG ACC CAG AGA AAG      1664
Leu Arg His Arg Arg Gln Gly Lys His Trp Thr Ser Thr Gln Arg Lys
485                 490                 495

GCT GAT TTC CAA CAT CCT GCA GGG GCT GTG GGG CCA GAG CCC ACA GAC      1712
Ala Asp Phe Gln His Pro Ala Gly Ala Val Gly Pro Glu Pro Thr Asp
500                 505                 510                 515

AGA GGC CTG CAG TGG AGG TCC AGC CCA GCT GCC GAT GCC CAG GAA GAA      1760
Arg Gly Leu Gln Trp Arg Ser Ser Pro Ala Ala Asp Ala Gln Glu Glu
                520                 525                 530

AAC CTC TAT GCT GCC GTG AAG CAC ACA CAG CCT GAG GAT GGG GTG GAG      1808
Asn Leu Tyr Ala Ala Val Lys His Thr Gln Pro Glu Asp Gly Val Glu
            535                 540                 545

ATG GAC ACT CGG CAG AGC CCA CAC GAT GAA GAC CCC CAG GCA GTG ACG      1856
Met Asp Thr Arg Gln Ser Pro His Asp Glu Asp Pro Gln Ala Val Thr
        550                 555                 560

TAT GCC GAG GTG AAA CAC TCC AGA CCT AGG AGA GAA ATG GCC TCT CCT      1904
Tyr Ala Glu Val Lys His Ser Arg Pro Arg Arg Glu Met Ala Ser Pro
    565                 570                 575

CCT TCC CCA CTG TCT GGG GAA TTC CTG GAC ACA AAG GAC AGA CAG GCG      1952
Pro Ser Pro Leu Ser Gly Glu Phe Leu Asp Thr Lys Asp Arg Gln Ala
580                 585                 590                 595

GAA GAG GAC AGG CAG ATG GAC ACT GAG GCT GCT GCA TCT GAA GCC CCC      2000
Glu Glu Asp Arg Gln Met Asp Thr Glu Ala Ala Ala Ser Glu Ala Pro
                600                 605                 610

CAG GAT GTG ACC TAC GCC CAG CTG CAC AGC TTG ACC CTC AGA CGG GAG      2048
Gln Asp Val Thr Tyr Ala Gln Leu His Ser Leu Thr Leu Arg Arg Glu
            615                 620                 625
```

```
GCA ACT GAG CCT CCT CCA TCC CAG GAA GGG CCC TCT CCA GCT GTG CCC    2096
Ala Thr Glu Pro Pro Pro Ser Gln Glu Gly Pro Ser Pro Ala Val Pro
        630             635             640

AGC ATC TAC GCC ACT CTG GCC ATC CAC TAG CCCAGGGGGG GACGCAGACC      2146
Ser Ile Tyr Ala Thr Leu Ala Ile His
        645             650

CCACACTCCA TGGAGTCTGG AATGCATGGG AGCTGCCCCC CCAGTGGACA CCATTGGACC  2206

CCACCCAGCC TGGATCTACC CCAGGAGACT CTGGGAACTT TTAGGGGTCA CTCAATTCTG  2266

CAGTATAAAT AACTAATGTC TCTACAATTT TGAAATAAAG CAATAGACTT CTCAATAATC  2326

AATGAAGTAG CTGAGAAAAC TAAGTCAGAA AGTGCATTAA ACTGAATCAC AATGTAAATA  2386

TTACACATCA AGCGATGAAA CTGGAAAACT ACAAGCCACG AATGAATGAA TTAGGAAAGA  2446

AAAAAAGTAG GAAATGAATG ATCTTGGCTT TCCTATAAGA AATTTAGGGC AGGGCACGGT  2506

GGCTCACGCC TGTAATTCCA GCACTTTGGG AGGCCGAGGC GGGCAGATCA CGAGTTCAGG  2566

AGATCGAGAC CATCTTGGCC AACATGGTGA AACCCTGTCT CTCCTAAAAA TACAAAAATT  2626

AGCTGGGATGT GGTGGCAGTG CCTGTAATCC CAGCTATTTG GGAGGCTGAG GCAGGAGAAT  2686

CGCTTGAACC AGGGAGTCAG AGGTTTCAGT GAGCCAAGAT CGCACCACTG CTCTCCAGCC  2746

TGGCGACAGA GGGAGACTCC ATCTCAAATT A                                 2777

(2) INFORMATION FOR SEQ ID NO: 4:

(i) SEQUENCE CHARACTERISTICS:
        (A) LENGTH: 652 amino acids
        (B) TYPE: amino acid
        (D) TOPOLOGY: linear (ii) MOLECULE TYPE: protein (xi) SEQUENCE DESCRIPTION: SEQ ID NO: 4:

Met Thr Pro Ile Leu Thr Val Leu Ile Cys Leu Gly Leu Ser Leu Gly
 1               5                  10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Leu Trp Ile Thr Arg Ile Pro Gln Glu Leu Val Lys Lys
 65                 70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
               100                 105                 110

Pro Leu Glu Leu Val Val Thr Gly Ala Tyr Ile Lys Pro Thr Leu Ser
           115                 120                 125

Ala Gln Pro Ser Pro Val Val Asn Ser Gly Gly Asn Val Ile Leu Gln
       130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
               165                 170                 175

Ser Ser Arg Ala Ile Phe Ser Val Gly Pro Val Ser Pro Ser Arg Arg
           180                 185                 190

Trp Trp Tyr Arg Cys Tyr Ala Tyr Asp Ser Asn Ser Pro Tyr Glu Trp
```

-continued

```
            195                 200                 205
Ser Leu Pro Ser Asp Leu Leu Glu Leu Leu Val Leu Gly Val Ser Lys
210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
                260                 265                 270

Pro Gln Ala Gly Leu Ser Gln Ala Asn Phe Thr Leu Gly Pro Val Ser
                275                 280                 285

Arg Ser Tyr Gly Gly Gln Tyr Arg Cys Tyr Gly Ala His Asn Leu Ser
290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
                340                 345                 350

Gln Thr Phe Leu Leu Thr Lys Glu Gly Ala Ala Asp Asp Pro Trp Arg
                355                 360                 365

Leu Arg Ser Thr Tyr Gln Ser Gln Lys Tyr Gln Ala Glu Phe Pro Met
                370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
                420                 425                 430

Pro Thr Ser Thr Ser Ala Gly Pro Glu Asp Gln Pro Leu Thr Pro Thr
                435                 440                 445

Gly Ser Asp Pro Gln Ser Gly Leu Gly Arg His Leu Gly Val Val Ile
450                 455                 460

Gly Ile Leu Val Ala Val Ile Leu Leu Leu Leu Leu Leu Leu Leu Leu
465                 470                 475                 480

Phe Leu Ile Leu Arg His Arg Arg Gln Gly Lys His Trp Thr Ser Thr
                485                 490                 495

Gln Arg Lys Ala Asp Phe Gln His Pro Ala Gly Ala Val Gly Pro Glu
                500                 505                 510

Pro Thr Asp Arg Gly Leu Gln Trp Arg Ser Ser Pro Ala Ala Asp Ala
                515                 520                 525

Gln Glu Glu Asn Leu Tyr Ala Ala Val Lys His Thr Gln Pro Glu Asp
                530                 535                 540

Gly Val Glu Met Asp Thr Arg Gln Ser Pro His Asp Glu Asp Pro Gln
545                 550                 555                 560

Ala Val Thr Tyr Ala Glu Val Lys His Ser Arg Pro Arg Arg Glu Met
                565                 570                 575

Ala Ser Pro Pro Ser Pro Leu Ser Gly Glu Phe Leu Asp Thr Lys Asp
                580                 585                 590

Arg Gln Ala Glu Glu Asp Arg Gln Met Asp Thr Glu Ala Ala Ala Ser
                595                 600                 605

Glu Ala Pro Gln Asp Val Thr Tyr Ala Gln Leu His Ser Leu Thr Leu
610                 615                 620
```

```
Arg Arg Glu Ala Thr Glu Pro Pro Ser Gln Glu Gly Pro Ser Pro
625                 630                 635                 640

Ala Val Pro Ser Ile Tyr Ala Thr Leu Ala Ile His
                645                 650
```

(2) INFORMATION FOR SEQ ID NO: 5:

(i) SEQUENCE CHARACTERISTICS:
        (A) LENGTH: 30 nucleotides
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 5:

```
TATGTCGACC ATGACCCCCA TCCTCACGGT                                    30
```

(2) INFORMATION FOR SEQ ID NO: 6:

(i) SEQUENCE CHARACTERISTICS:
        (A) LENGTH: 52 nucleotides
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO: 6:

```
TATGGGCTCT GCTCCAGGAG AAGATCTTCC TTCTATAACC CCCAGGTGCC TT            52
```

(2) INFORMATION FOR SEQ ID NO: 7:

(i) SEQUENCE CHARACTERISTICS:
        (A) LENGTH: 1605 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: pbm25

(ix) FEATURE:
        (A) NAME/KEY: CDS
        (B) LOCATION: 93..1409

(xi) SEQUENCE DESCRIPTION: SEQ ID NO: 7:

```
GAGCCTCCAA GTGTCCACAC CCTGTGTGTC CTCTGTCCTG CCAGCACCGA GGGCTCATCC    60

ATCCACAGAG CAGTGCAGTG GGAGGAGACG CC ATG ACC CCC ATC CTC ACG GTC    113
                                   Met Thr Pro Ile Leu Thr Val
                                     1               5

CTG ATC TGT CTC GGG CTG AGC CTG GAC CCC AGG ACC CAC GTG CAG GCA    161
Leu Ile Cys Leu Gly Leu Ser Leu Asp Pro Arg Thr His Val Gln Ala
         10                  15                  20

GGG CCC CTC CCC AAG CCC ACC CTC TGG GCT GAG CCA GGC TCT GTG ATC    209
Gly Pro Leu Pro Lys Pro Thr Leu Trp Ala Glu Pro Gly Ser Val Ile
     25                  30                  35

ACC CAA GGG AGT CCT GTG ACC CTC AGG TGT CAG GGG AGC CTG GAG ACG    257
Thr Gln Gly Ser Pro Val Thr Leu Arg Cys Gln Gly Ser Leu Glu Thr
 40                  45                  50                  55

CAG GAG TAC CAT CTA TAT AGA GAA AAG AAA ACA GCA CTC TGG ATT ACA    305
Gln Glu Tyr His Leu Tyr Arg Glu Lys Lys Thr Ala Leu Trp Ile Thr
                 60                  65                  70
```

```
CGG ATC CCA CAG GAG CTT GTG AAG AAG GGC CAG TTC CCC ATC CTA TCC      353
Arg Ile Pro Gln Glu Leu Val Lys Lys Gly Gln Phe Pro Ile Leu Ser
         75                  80                  85

ATC ACC TGG GAA CAT GCA GGG CGG TAT TGC TGT ATC TAT GGC AGC CAC      401
Ile Thr Trp Glu His Ala Gly Arg Tyr Cys Cys Ile Tyr Gly Ser His
         90                  95                 100

ACT GCA GGC CTC TCA GAG AGC AGT GAC CCC CTG GAG CTG GTG GTG ACA      449
Thr Ala Gly Leu Ser Glu Ser Ser Asp Pro Leu Glu Leu Val Val Thr
        105                 110                 115

GGA GCC TAC AGC AAA CCC ACC CTC TCA GCT CTG CCC AGC CCT GTG GTG      497
Gly Ala Tyr Ser Lys Pro Thr Leu Ser Ala Leu Pro Ser Pro Val Val
120                 125                 130                 135

ACC TCA GGA AGG AAT GTG ACC ATC CAG TGT GAC TCA CAG GTG GCA TTT      545
Thr Ser Gly Arg Asn Val Thr Ile Gln Cys Asp Ser Gln Val Ala Phe
        140                 145                 150

GAT GGC TTC ATT CTG TGT AAG GAA GGA GAA GAT GAA CAC CCA CAA TGC      593
Asp Gly Phe Ile Leu Cys Lys Glu Gly Glu Asp Glu His Pro Gln Cys
        155                 160                 165

CTG AAC TCC CAT TCC CAT GCC CGT GGG TCA TCC CGG GCC ATC TTC TCC      641
Leu Asn Ser His Ser His Ala Arg Gly Ser Ser Arg Ala Ile Phe Ser
        170                 175                 180

GTG GGC CCC GTG AGC CCA AGT CGC AGG TGG TCG TAC AGG TGC TAT GGT      689
Val Gly Pro Val Ser Pro Ser Arg Arg Trp Ser Tyr Arg Cys Tyr Gly
        185                 190                 195

TAT GAC TCG CGC GCT CCC TAT GTG TGG TCT CTA CCC AGT GAT CTC CTG      737
Tyr Asp Ser Arg Ala Pro Tyr Val Trp Ser Leu Pro Ser Asp Leu Leu
200                 205                 210                 215

GGG CTC CTG GTC CCA GGT GTT TCT AAG AAG CCA TCA CTC TCA GTG CAG      785
Gly Leu Leu Val Pro Gly Val Ser Lys Lys Pro Ser Leu Ser Val Gln
        220                 225                 230

CCG GGT CCT GTC GTG GCC CCT GGG GAG AAG CTG ACC TTC CAG TGT GGC      833
Pro Gly Pro Val Val Ala Pro Gly Glu Lys Leu Thr Phe Gln Cys Gly
        235                 240                 245

TCT GAT GCC GGC TAC GAC AGA TTT GTT CTG TAC AAG GAG TGG GGA CGT      881
Ser Asp Ala Gly Tyr Asp Arg Phe Val Leu Tyr Lys Glu Trp Gly Arg
        250                 255                 260

GAC TTC CTC CAG CGC CCT GGC CGG CAG CCC CAG GCT GGG CTC TCC CAG      929
Asp Phe Leu Gln Arg Pro Gly Arg Gln Pro Gln Ala Gly Leu Ser Gln
        265                 270                 275

GCC AAC TTC ACC CTG GGC CCT GTG AGC CGC TCC TAC GGG GGC CAG TAC      977
Ala Asn Phe Thr Leu Gly Pro Val Ser Arg Ser Tyr Gly Gly Gln Tyr
280                 285                 290                 295

ACA TGC TCC GGT GCA TAC AAC CTC TCC TCC GAG TGG TCG GCC CCC AGC     1025
Thr Cys Ser Gly Ala Tyr Asn Leu Ser Ser Glu Trp Ser Ala Pro Ser
        300                 305                 310

GAC CCC CTG GAC ATC CTG ATC ACA GGA CAG ATC CGT GCC AGA CCC TTC     1073
Asp Pro Leu Asp Ile Leu Ile Thr Gly Gln Ile Arg Ala Arg Pro Phe
        315                 320                 325

CTC TCC GTG CGG CCG GGC CCC ACA GTG GCC TCA GGA GAG AAC GTG ACC     1121
Leu Ser Val Arg Pro Gly Pro Thr Val Ala Ser Gly Glu Asn Val Thr
        330                 335                 340

CTG CTG TGT CAG TCA CAG GGA GGG ATG CAC ACT TTC CTT TTG ACC AAG     1169
Leu Leu Cys Gln Ser Gln Gly Gly Met His Thr Phe Leu Leu Thr Lys
        345                 350                 355

GAG GGG GCA GCT GAT TCC CCG CTG CGT CTA AAA TCA AAG CGC CAA TCT     1217
Glu Gly Ala Ala Asp Ser Pro Leu Arg Leu Lys Ser Lys Arg Gln Ser
360                 365                 370                 375

CAT AAG TAC CAG GCT GAA TTC CCC ATG AGT CCT GTG ACC TCG GCC CAC     1265
His Lys Tyr Gln Ala Glu Phe Pro Met Ser Pro Val Thr Ser Ala His
        380                 385                 390
```

```
GCG GGG ACC TAC AGG TGC TAC GGC TCA CTC AGC TCC AAC CCC TAC CTG    1313
Ala Gly Thr Tyr Arg Cys Tyr Gly Ser Leu Ser Ser Asn Pro Tyr Leu
            395                 400                 405

CTG ACT CAC CCC AGT GAC CCC CTG GAG CTC GTG GTC TCA GGA GCA GCT    1361
Leu Thr His Pro Ser Asp Pro Leu Glu Leu Val Val Ser Gly Ala Ala
        410                 415                 420

GAG ACC CTC AGC CCA CCA CAA AAC AAG TCC GAC TCC AAG GCT GGT GAG    1409
Glu Thr Leu Ser Pro Pro Gln Asn Lys Ser Asp Ser Lys Ala Gly Glu
    425                 430                 435

TGA GGAGATGCTT GCCGTGATGA CGCTGGGCAC AGAGGGTCAG GTCCTGTCAA         1462
 *
440

GAGGAGCTGG GTGTCCTGGG TGGACATTTG AAGAATTATA TTCATTCCAA CTTGAAGAAT  1522

TATTCAACAC CTTTAACAAT GTATATGTGA AGTACTTTAT TCTTTCATAT TTTAAAAATA  1582

AAAGATAATT ATCCATGAGA AAA                                         1605

(2) INFORMATION FOR SEQ ID NO: 8:

(i) SEQUENCE CHARACTERISTICS:
        (A) LENGTH: 439 amino acids
        (B) TYPE: amino acid
        (D) TOPOLOGY: linear (ii) MOLECULE TYPE: protein (xi) SEQUENCE DESCRIPTION: SEQ ID NO: 8:

Met Thr Pro Ile Leu Thr Val Leu Ile Cys Leu Gly Leu Ser Leu Asp
 1               5                  10                  15

Pro Arg Thr His Val Gln Ala Gly Pro Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Ser Leu Glu Thr Gln Glu Tyr His Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Leu Ser Ile Thr Trp Glu His Ala Gly Arg Tyr
                85                  90                  95

Cys Cys Ile Tyr Gly Ser His Thr Ala Gly Leu Ser Glu Ser Ser Asp
            100                 105                 110

Pro Leu Glu Leu Val Val Thr Gly Ala Tyr Ser Lys Pro Thr Leu Ser
        115                 120                 125

Ala Leu Pro Ser Pro Val Val Thr Ser Gly Arg Asn Val Thr Ile Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Leu Val Pro Gly Val Ser Lys
    210                 215                 220

Lys Pro Ser Leu Ser Val Gln Pro Gly Pro Val Val Ala Pro Gly Glu
225                 230                 235                 240
```

```
Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Thr Cys Ser Gly Ala Tyr Asn Leu Ser
    290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
    370                 375                 380

Ser Pro Val Thr Ser Ala His Ala Gly Thr Tyr Arg Cys Tyr Gly Ser
385                 390                 395                 400

Leu Ser Ser Asn Pro Tyr Leu Leu Thr His Pro Ser Asp Pro Leu Glu
                405                 410                 415

Leu Val Val Ser Gly Ala Ala Glu Thr Leu Ser Pro Pro Gln Asn Lys
            420                 425                 430

Ser Asp Ser Lys Ala Gly Glu
        435

(2) INFORMATION FOR SEQ ID NO: 9:

(i) SEQUENCE CHARACTERISTICS:
        (A) LENGTH: 2221 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: pbm8

(ix) FEATURE:
        (A) NAME/KEY: CDS
        (B) LOCATION: 184..1977

(xi) SEQUENCE DESCRIPTION: SEQ ID NO: 9:

GCTCACTGCC ACACGCAGCT CAGCCTGGGC GGCACAGCCA GATGCGAGAT GCGTCTCTGC      60

TGATCTGAGT CTGCCTGCAG CATGGACCTG GGTCTTCCCT GAAGCATCTC CAGGGCTGGA     120

GGGACGACTG CCATGCACCG AGGGCTCATC CATCCGCAGA GCAGGGCAGT GGGAGGAGAC     180

GCC ATG ACC CCC ATC GTC ACA GTC CTG ATC TGT CTC GGG CTG AGT CTG       228
    Met Thr Pro Ile Val Thr Val Leu Ile Cys Leu Gly Leu Ser Leu
    1               5                   10                  15

GGC CCC AGG ACC CAC GTG CAG ACA GGG ACC ATC CCC AAG CCC ACC CTG       276
Gly Pro Arg Thr His Val Gln Thr Gly Thr Ile Pro Lys Pro Thr Leu
            20                  25                  30

TGG GCT GAG CCA GAC TCT GTG ATC ACC CAG GGG AGT CCC GTC ACC CTC       324
Trp Ala Glu Pro Asp Ser Val Ile Thr Gln Gly Ser Pro Val Thr Leu
        35                  40                  45

AGT TGT CAG GGG AGC CTT GAA GCC CAG GAG TAC CGT CTA TAT AGG GAG       372
```

```
Ser Cys Gln Gly Ser Leu Glu Ala Gln Glu Tyr Arg Leu Tyr Arg Glu
         50                  55                  60

AAA AAA TCA GCA TCT TGG ATT ACA CGG ATA CGA CCA GAG CTT GTG AAG          420
Lys Lys Ser Ala Ser Trp Ile Thr Arg Ile Arg Pro Glu Leu Val Lys
     65                  70                  75

AAC GGC CAG TTC CAC ATC CCA TCC ATC ACC TGG GAA CAC ACA GGG CGA          468
Asn Gly Gln Phe His Ile Pro Ser Ile Thr Trp Glu His Thr Gly Arg
 80                  85                  90                  95

TAT GGC TGT CAG TAT TAC AGC CGC GCT CGG TGG TCT GAG CTC AGT GAC          516
Tyr Gly Cys Gln Tyr Tyr Ser Arg Ala Arg Trp Ser Glu Leu Ser Asp
                100                 105                 110

CCC CTG GTG CTG GTG ATG ACA GGA GCC TAC CCA AAA CCC ACC CTC TCA          564
Pro Leu Val Leu Val Met Thr Gly Ala Tyr Pro Lys Pro Thr Leu Ser
                115                 120                 125

GCC CAG CCC AGC CCT GTG GTG ACC TCA GGA GGA AGG GTG ACC CTC CAG          612
Ala Gln Pro Ser Pro Val Val Thr Ser Gly Gly Arg Val Thr Leu Gln
        130                 135                 140

TGT GAG TCA CAG GTG GCA TTT GGC GGC TTC ATT CTG TGT AAG GAA GGA          660
Cys Glu Ser Gln Val Ala Phe Gly Gly Phe Ile Leu Cys Lys Glu Gly
        145                 150                 155

GAA GAT GAA CAC CCA CAA TGC CTG AAC TCC CAG CCC CAT GCC CGT GGG          708
Glu Asp Glu His Pro Gln Cys Leu Asn Ser Gln Pro His Ala Arg Gly
160                 165                 170                 175

TCG TCC CGC GCC ATC TTC TCC GTG GGC CCC GTG AGC CCG AAT CGC AGG          756
Ser Ser Arg Ala Ile Phe Ser Val Gly Pro Val Ser Pro Asn Arg Arg
                180                 185                 190

TGG TCG CAC AGG TGC TAT GGT TAT GAC TTG AAC TCT CCC TAT GTG TGG          804
Trp Ser His Arg Cys Tyr Gly Tyr Asp Leu Asn Ser Pro Tyr Val Trp
                195                 200                 205

TCT TCA CCC AGT GAT CTC CTG GAG CTC CTG GTC CCA GGT GTT TCT AAG          852
Ser Ser Pro Ser Asp Leu Leu Glu Leu Leu Val Pro Gly Val Ser Lys
        210                 215                 220

AAG CCA TCA CTC TCA GTG CAG CCG GGT CCT GTC GTG GCC CCT GGG GAA          900
Lys Pro Ser Leu Ser Val Gln Pro Gly Pro Val Val Ala Pro Gly Glu
225                 230                 235

AGC CTG ACC CTC CAG TGT GTC TCT GAT GTC GGC TAT GAC AGA TTT GTT          948
Ser Leu Thr Leu Gln Cys Val Ser Asp Val Gly Tyr Asp Arg Phe Val
240                 245                 250                 255

CTG TAC AAG GAG GGG GAA CGT GAC CTT CGC CAG CTC CCT GGC CGG CAG          996
Leu Tyr Lys Glu Gly Glu Arg Asp Leu Arg Gln Leu Pro Gly Arg Gln
                260                 265                 270

CCC CAG GCT GGG CTC TCC CAG GCC AAC TTC ACC CTG GGC CCT GTG AGC         1044
Pro Gln Ala Gly Leu Ser Gln Ala Asn Phe Thr Leu Gly Pro Val Ser
                275                 280                 285

CGC TCC TAC GGG GGC CAG TAC AGA TGC TAC GGT GCA TAC AAC CTC TCC         1092
Arg Ser Tyr Gly Gly Gln Tyr Arg Cys Tyr Gly Ala Tyr Asn Leu Ser
        290                 295                 300

TCC GAG TGG TCG GCC CCC AGC GAC CCC CTG GAC ATC CTG ATC ACA GGA         1140
Ser Glu Trp Ser Ala Pro Ser Asp Pro Leu Asp Ile Leu Ile Thr Gly
        305                 310                 315

CAG ATC CAT GGC ACA CCC TTC ATC TCA GTG CAG CCA GGC CCC ACA GTG         1188
Gln Ile His Gly Thr Pro Phe Ile Ser Val Gln Pro Gly Pro Thr Val
320                 325                 330                 335

GCC TCA GGA GAG AAC GTG ACC CTG CTG TGT CAG TCA TGG CGG CAG TTC         1236
Ala Ser Gly Glu Asn Val Thr Leu Leu Cys Gln Ser Trp Arg Gln Phe
                340                 345                 350

CAC ACT TTC CTT CTG ACC AAG GCG GGA GCA GCT GAT GCC CCA CTC CGT         1284
His Thr Phe Leu Leu Thr Lys Ala Gly Ala Ala Asp Ala Pro Leu Arg
                355                 360                 365
```

```
CTA AGA TCA ATA CAC GAA TAT CCT AAG TAC CAG GCT GAA TTC CCC ATG    1332
Leu Arg Ser Ile His Glu Tyr Pro Lys Tyr Gln Ala Glu Phe Pro Met
        370                 375                 380

AGT CCT GTG ACC TCA GCC CAC GCG GGG ACC TAC AGG TGC TAC GGC TCA    1380
Ser Pro Val Thr Ser Ala His Ala Gly Thr Tyr Arg Cys Tyr Gly Ser
385                 390                 395

CTC AAC TCC GAC CCC TAC CTG CTG TCT CAC CCC AGT GAG CCC CTG GAG    1428
Leu Asn Ser Asp Pro Tyr Leu Leu Ser His Pro Ser Glu Pro Leu Glu
400                 405                 410                 415

CTC GTG GTC TCA GGA CCC TCC ATG GGT TCC AGC CCC CCA CCC ACC GGT    1476
Leu Val Val Ser Gly Pro Ser Met Gly Ser Ser Pro Pro Pro Thr Gly
                420                 425                 430

CCC ATC TCC ACA CCT GCA GGC CCT GAG GAC CAG CCC CTC ACC CCC ACT    1524
Pro Ile Ser Thr Pro Ala Gly Pro Glu Asp Gln Pro Leu Thr Pro Thr
            435                 440                 445

GGG TCG GAT CCC CAA AGT GGT CTG GGA AGG CAC CTG GGG GTT GTG ATC    1572
Gly Ser Asp Pro Gln Ser Gly Leu Gly Arg His Leu Gly Val Val Ile
        450                 455                 460

GGC ATC TTG GTG GCC GTC GTC CTA CTG CTC CTC CTC CTC CTC CTC CTC    1620
Gly Ile Leu Val Ala Val Val Leu Leu Leu Leu Leu Leu Leu Leu Leu
465                 470                 475

TTC CTC ATC CTC CGA CAT CGA CGT CAG GGC AAA CAC TGG ACA TCG ACC    1668
Phe Leu Ile Leu Arg His Arg Arg Gln Gly Lys His Trp Thr Ser Thr
480                 485                 490                 495

CAG AGA AAG GCT GAT TTC CAA CAT CCT GCA GGG GCT GTG GGG CCA GAG    1716
Gln Arg Lys Ala Asp Phe Gln His Pro Ala Gly Ala Val Gly Pro Glu
                500                 505                 510

CCC ACA GAC AGA GGC CTG CAG TGG AGG TCC AGC CCA GCT GCC GAC GCC    1764
Pro Thr Asp Arg Gly Leu Gln Trp Arg Ser Ser Pro Ala Ala Asp Ala
            515                 520                 525

CAG GAA GAA AAC CTC TAT GCT GCC GTG AAG GAC ACA CAG CCT GAA GAT    1812
Gln Glu Glu Asn Leu Tyr Ala Ala Val Lys Asp Thr Gln Pro Glu Asp
        530                 535                 540

GGG GTG GAG ATG GAC ACT CGG GCT GCT GCA TCT GAA GCC CCC CAG GAT    1860
Gly Val Glu Met Asp Thr Arg Ala Ala Ala Ser Glu Ala Pro Gln Asp
545                 550                 555

GTG ACC TAC GCC CAG CTG CAC AGC TTG ACC CTC AGA CGG AAG GCA ACT    1908
Val Thr Tyr Ala Gln Leu His Ser Leu Thr Leu Arg Arg Lys Ala Thr
560                 565                 570                 575

GAG CCT CCT CCA TCC CAG GAA AGG GAA CCT CCA GCT GAG CCC AGC ATC    1956
Glu Pro Pro Pro Ser Gln Glu Arg Glu Pro Pro Ala Glu Pro Ser Ile
                580                 585                 590

TAC GCC ACC CTG GCC ATC CAC TAG CCCGGAGGGT ACGCAGACTC CACACTCAGT   2010
Tyr Ala Thr Leu Ala Ile His
            595

AGAAGGAGAC TCAGGACTGC TGAAGGCACG GGAGCTGCCC CCAGTGGACA CCAATGAACC   2070

CCAGTCAGCC TGGACCCCTA ACAAAGACCA TGAGGAGATG CTGGGAACTT TGGGACTCAC   2130

TTGATTCTGC AGTCGAAATA ACTAATATCC CTACATTTTT TAATTAAAGC AACAGACTTC   2190

TCAATAAAAG CAGGTCGTCT CGTTCCAATC T                                 2221

(2) INFORMATION FOR SEQ ID NO: 10:

(i) SEQUENCE CHARACTERISTICS:
        (A) LENGTH: 598 amino acids
        (B) TYPE: amino acid
        (D) TOPOLOGY: linear (ii) MOLECULE TYPE: protein (xi) SEQUENCE DESCRIPTION: SEQ ID NO: 10:
```

```
Met Thr Pro Ile Val Thr Val Leu Ile Cys Leu Gly Leu Ser Leu Gly
  1               5                  10                  15

Pro Arg Thr His Val Gln Thr Gly Ile Pro Lys Pro Thr Leu Trp
             20                  25                  30

Ala Glu Pro Asp Ser Val Ile Thr Gln Gly Ser Pro Val Thr Leu Ser
             35                  40                  45

Cys Gln Gly Ser Leu Glu Ala Gln Glu Tyr Arg Leu Tyr Arg Glu Lys
 50                  55                  60

Lys Ser Ala Ser Trp Ile Thr Arg Ile Arg Pro Glu Leu Val Lys Asn
 65                  70                  75                  80

Gly Gln Phe His Ile Pro Ser Ile Thr Trp Glu His Thr Gly Arg Tyr
                 85                  90                  95

Gly Cys Gln Tyr Tyr Ser Arg Ala Arg Trp Ser Glu Leu Ser Asp Pro
                100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
            195                 200                 205

Ser Pro Ser Asp Leu Leu Glu Leu Leu Val Pro Gly Val Ser Lys Lys
            210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
                260                 265                 270

Gln Ala Gly Leu Ser Gln Ala Asn Phe Thr Leu Gly Pro Val Ser Arg
            275                 280                 285

Ser Tyr Gly Gly Gln Tyr Arg Cys Tyr Gly Ala Tyr Asn Leu Ser Ser
290                 295                 300

Glu Trp Ser Ala Pro Ser Asp Pro Leu Asp Ile Leu Ile Thr Gly Gln
305                 310                 315                 320

Ile His Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
            355                 360                 365

Arg Ser Ile His Glu Tyr Pro Lys Tyr Gln Ala Glu Phe Pro Met Ser
            370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415
```

```
Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys Asp Thr Gln Pro Glu Asp Gly
    530                 535                 540

Val Glu Met Asp Thr Arg Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
                580                 585                 590

Ala Thr Leu Ala Ile His
            595

(2) INFORMATION FOR SEQ ID NO: 11:

(i) SEQUENCE CHARACTERISTICS:
        (A) LENGTH: 2446 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: pbm36-2

(ix) FEATURE:
        (A) NAME/KEY: CDS
        (B) LOCATION: 171..1037

(xi) SEQUENCE DESCRIPTION: SEQ ID NO: 11:

CGCAGCTCAA CCTGAGCTAC ACAGCCAGAT GCGAGATGCT TCTCTGCTGA TCTGAGTCTG      60

CCTGCAGCAT GGACCTTGGT CTTCCCTGAA GCATCTCCAG GGCTGGAGGG ACGACTGCCA     120

TGCACCTAGG GCTTATCCAT CCGCAGAGCA GGGCAGTGGG AGGAGACGCT ATG ACC       176
                                                        Met Thr
                                                          1

CCC ATC CTC ACG GTC CTG ATC TGT CTC GGG CTG AGT CTG GGC CCC CGG     224
Pro Ile Leu Thr Val Leu Ile Cys Leu Gly Leu Ser Leu Gly Pro Arg
        5                   10                  15

ACC CAC GTG CAG GCA GGG ACC CTC CCC AAG CCC ACA CTC TGG GCT GAG     272
Thr His Val Gln Ala Gly Thr Leu Pro Lys Pro Thr Leu Trp Ala Glu
    20                  25                  30

CCA GGC TCT GTG ATC ACC CAG GGG AGT CCC GTG ACC CTC TGG TGT CAG     320
Pro Gly Ser Val Ile Thr Gln Gly Ser Pro Val Thr Leu Trp Cys Gln
35                  40                  45                  50

GGG ATC CTG GAG ACC CAG GAG TAC CGT CTG TAT AGA GAA AAG AAA ACA     368
Gly Ile Leu Glu Thr Gln Glu Tyr Arg Leu Tyr Arg Glu Lys Lys Thr
                55                  60                  65
```

-continued

```
GCA CCC TGG ATT ACA CGG ATC CCA CAG GAG ATT GTG AAG AAG GGC CAG    416
Ala Pro Trp Ile Thr Arg Ile Pro Gln Glu Ile Val Lys Lys Gly Gln
            70                  75                  80

TTC CCC ATC CCG TCC ATC ACC TGG GAA CAC ACC GGG CGG TAT CGC TGT    464
Phe Pro Ile Pro Ser Ile Thr Trp Glu His Thr Gly Arg Tyr Arg Cys
        85                  90                  95

TTC TAC GGT AGC CAC ACT GCA GGC TGG TCA GAG CCC AGT GAC CCC CTG    512
Phe Tyr Gly Ser His Thr Ala Gly Trp Ser Glu Pro Ser Asp Pro Leu
    100                 105                 110

GAG CTG GTG GTG ACA GGA GCC TAC ATC AAA CCC ACC CTC TCG GCT CTA    560
Glu Leu Val Val Thr Gly Ala Tyr Ile Lys Pro Thr Leu Ser Ala Leu
115                 120                 125                 130

CCC AGC CCT GTG GTG ACC TCA GGA GGG AAC GTG ACC CTC CAT TGT GTC    608
Pro Ser Pro Val Val Thr Ser Gly Gly Asn Val Thr Leu His Cys Val
                135                 140                 145

TCA CAG GTG GCA TTT GGC AGC TTC ATT CTG TGT AAG GAA GGA GAA GAT    656
Ser Gln Val Ala Phe Gly Ser Phe Ile Leu Cys Lys Glu Gly Glu Asp
            150                 155                 160

GAA CAC CCA CAA TGC CTG AAC TCA CAG CCC CGT ACC CAT GGG TGG TCC    704
Glu His Pro Gln Cys Leu Asn Ser Gln Pro Arg Thr His Gly Trp Ser
        165                 170                 175

CGG GCC ATC TTC TCT GTG GGC CCC GTG AGC CCG AGT CGC AGG TGG TCG    752
Arg Ala Ile Phe Ser Val Gly Pro Val Ser Pro Ser Arg Arg Trp Ser
    180                 185                 190

TAC AGG TGC TAT GCT TAT GAC TCG AAC TCT CCC CAT GTG TGG TCT CTA    800
Tyr Arg Cys Tyr Ala Tyr Asp Ser Asn Ser Pro His Val Trp Ser Leu
195                 200                 205                 210

CCC AGT GAT CTC CTG GAG CTC CTG GTC CCA GGA GCA GCT GAG ACC CTC    848
Pro Ser Asp Leu Leu Glu Leu Leu Val Pro Gly Ala Ala Glu Thr Leu
                215                 220                 225

AGC CCA CCA CAA AAC AAG TCC GAT TCC AAG GCT GGA GCA GCT AAC ACC    896
Ser Pro Pro Gln Asn Lys Ser Asp Ser Lys Ala Gly Ala Ala Asn Thr
            230                 235                 240

CTC AGC CCA TCA CAA AAC AAG ACT GCC TCA CAC CCC CAG GAT TAC ACA    944
Leu Ser Pro Ser Gln Asn Lys Thr Ala Ser His Pro Gln Asp Tyr Thr
        245                 250                 255

GTG GAG AAT CTC ATC CGC ATG GGC ATA GCT GGC TTG GTC CTG GTG GTC    992
Val Glu Asn Leu Ile Arg Met Gly Ile Ala Gly Leu Val Leu Val Val
    260                 265                 270

CTC GGG ATT CTG CTA TTT GAG GCT CAG CAC AGC CAG AGA AGC CTC TGA   1040
Leu Gly Ile Leu Leu Phe Glu Ala Gln His Ser Gln Arg Ser Leu
275                 280                 285

GATGCAGCCG GGAGGTGAAC AGCAGAGAGA AGAATGTACC CTTCAGAGTG GTGGAGCCTT  1100

GGGAACAGAT CTGATGATGC CAGGAGGTTC CGGGAGACAA TTTAGGGCTG ATGCTATCTG  1160

GACTGTCTGC CAATCATTTT TAGAGGGAGG AATCAGTGTT GGATTGCAGA GACATTTTCT  1220

GGAGTGATCC ATGAAGGACC ATTAACATGT GATACCTTTC CTCTCTATTA ATGTTGACTT  1280

CCCTTGGTTG GATCCTCTTC TTTCCCCACC CCCAGACAGA CATGAGGCTA CATCCCACAT  1340

GGCAGCGTTG GTCCACACC TCTGCACATC TGTGTGCTCT GGTCCATGGT GTGTAACACA   1400

GTCTTCTTTA TTACTCATTG CCATACTCCC TGGTGTGCTT TACTGAGCCT CCATCTCTTC  1460

AATTCAGAGT TCCAAACGTG CTTCAGTAAC TAAATCAATG GGAGAGTATC GGATTTCAAC  1520

CAGGAAAAGA TAAATCCACC CTGATGCCCT GACACCCTCT CTGAACCCTA CGAGCCCTTC  1580

CCTCCTTCTC ACATGCTACC TGTGCAGCTT CTCCTTAGAT CATTGTGTAA CCATCACTGC  1640

CATCCTGTTC CACACATGGT CATCACCCTA CACCCATTCA GCAGCCACTC CCCATTCCCT  1700
```

```
CTTCCCTCCA GCACCTGCTA ACCACAAATG TGCTTTCTGT CTCTACGGAT TTGCCTATTC    1760

TGTCTGAAAA CATTTCAATC TCCTTTGACC TGTGAGCTCC TCACTTCGAG ACTTCCTGCC    1820

TTTCCAGGCA GAACCAAAGT ACACCACGTC AAAAGCAATG ATAGGCATTT GCAGTGTGTT    1880

GGTGATCCAC GAAAGGAAAA TCACGGAAGC AGGATAGAAA TCCAGCTGCA GACAAGACCT    1940

CAGGTCGATG AATCTTGACA AGCAGTTGAG CTGTTTTTTT CTACTCACCT AGGACAGTCA    2000

GGCAGAAGTA TGCAAAATGA CTGGGGCTGA TTCTTTTCTG AATTGTCGCA AACAGCAAGA    2060

GGACTTGAGT CCTAGCATTA AAGAGTTCAA CATGTCTAGG TCCAAGACCA CTGTTGTGTT    2120

TGAAGGATGT AAAACCCTGC TGCATAGGAT GGAATATTTG GAGGGAGGAT CCTGAAAAAC    2180

ATGAGGGATC AAATAGTCCT CAACTTTCTA GGACAAAGGG AGCAGCTATT TGCCATCTAC    2240

CCTCCAGAAT AAAGAAATCT TATCATTCAC CATCTACCCT CTAGAATAAA GAAATCTTAT    2300

CATTCGCCAT CTACCCTGTA GAATAAAGAA ATCTTATCAT TCACCGTCTA CCCTCTAGAG    2360

TAAACAAATC TTATCATTCA CCATCTACCC TCTAGAATAA AGAAATCTTA TCATTCGCCA    2420

TCTACCCTCT AGAATAAAGA AATCTT                                        2446
```

(2) INFORMATION FOR SEQ ID NO: 12:

(i) SEQUENCE CHARACTERISTICS:
        (A) LENGTH: 289 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Thr Pro Ile Leu Thr Val Leu Ile Cys Leu Gly Leu Ser Leu Gly
 1               5                  10                  15

Pro Arg Thr His Val Gln Ala Gly Thr Leu Pro Lys Pro Thr Leu Trp
                20                  25                  30

Ala Glu Pro Gly Ser Val Ile Thr Gln Gly Ser Pro Val Thr Leu Trp
            35                  40                  45

Cys Gln Gly Ile Leu Glu Thr Gln Glu Tyr Arg Leu Tyr Arg Glu Lys
        50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Pro Gly Ala Ala Glu
    210                 215                 220
```

-continued

```
Thr Leu Ser Pro Pro Gln Asn Lys Ser Asp Ser Lys Ala Gly Ala Ala
225                 230                 235                 240

Asn Thr Leu Ser Pro Ser Gln Asn Lys Thr Ala Ser His Pro Gln Asp
                245                 250                 255

Tyr Thr Val Glu Asn Leu Ile Arg Met Gly Ile Ala Gly Leu Val Leu
            260                 265                 270

Val Val Leu Gly Ile Leu Leu Phe Glu Ala Gln His Ser Gln Arg Ser
        275                 280                 285

Leu
```

(2) INFORMATION FOR SEQ ID NO: 13:

(i) SEQUENCE CHARACTERISTICS:
        (A) LENGTH: 1910 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: pbm36-4

(ix) FEATURE:
        (A) NAME/KEY: CDS
        (B) LOCATION: 183..1649

(xi) SEQUENCE DESCRIPTION: SEQ ID NO: 13:

```
CTCACTGCCA CACGCAGCTC AACCTGAGCT ACACAGCCAG ATGCGAGATG CTTCTCTGCT      60

GATCTGAGTC TGCCTGCAGC ATGGACCTTG GTCTTCCCTG AAGCATCTCC AGGGCTGGAG     120

GGACGACTGC CATGCACCGA GGGCTCATCC ATCCGCAGAG CAGGGCAGTG GGAGGAGACG     180

CT ATG ACC CCC ATC GTC ACA GTC CTG ATC TGT CTC AGG CTG AGT CTG        227
   Met Thr Pro Ile Val Thr Val Leu Ile Cys Leu Arg Leu Ser Leu
   1               5                  10                  15

GGC CCC CGG ACC CAC GTG CAG GCA GGG ACC CTC CCC AAG CCC ACA CTC        275
Gly Pro Arg Thr His Val Gln Ala Gly Thr Leu Pro Lys Pro Thr Leu
            20                  25                  30

TGG GCT GAG CCA GGC TCT GTG ATC ACC CAG GGG AGT CCC GTG ACC CTC        323
Trp Ala Glu Pro Gly Ser Val Ile Thr Gln Gly Ser Pro Val Thr Leu
        35                  40                  45

TGG TGT CAG GGG ATC CTG GAG ACC CAG GAG TAC CGT CTG TAT AGA GAA        371
Trp Cys Gln Gly Ile Leu Glu Thr Gln Glu Tyr Arg Leu Tyr Arg Glu
    50                  55                  60

AAG AAA ACA GCA CCC TGG ATT ACA CGG ATC CCA CAG GAG ATT GTG AAG        419
Lys Lys Thr Ala Pro Trp Ile Thr Arg Ile Pro Gln Glu Ile Val Lys
65                  70                  75

AAG GGC CAG TTC CCC ATC CCA TCC ATC ACC TGG GAA CAC ACA GGG CGG        467
Lys Gly Gln Phe Pro Ile Pro Ser Ile Thr Trp Glu His Thr Gly Arg
 80                  85                  90                  95

TAT CGC TGT TTC TAC GGT AGC CAC ACT GCA GGC TGG TCA GAG CCC AGT        515
Tyr Arg Cys Phe Tyr Gly Ser His Thr Ala Gly Trp Ser Glu Pro Ser
                100                 105                 110

GAC CCC CTG GAG CTG GTG GTG ACA GGA GCC TAC ATC AAA CCC ACC CTC        563
Asp Pro Leu Glu Leu Val Val Thr Gly Ala Tyr Ile Lys Pro Thr Leu
            115                 120                 125

TCA GCT CTA CCC AGC CCT GTG GTG ACC TCA GGA GGG AAC GTG ACC CTC        611
Ser Ala Leu Pro Ser Pro Val Val Thr Ser Gly Gly Asn Val Thr Leu
        130                 135                 140

CAT TGT GTC TCA CAG GTG GCA TTT GGC AGC TTC ATT CTG TGT AAG GAA        659
```

```
                His Cys Val Ser Gln Val Ala Phe Gly Ser Phe Ile Leu Cys Lys Glu
                    145                 150                 155

GGA GAA GAT GAA CAC CCA CAA TGC CTG AAC TCA CAG CCC CGT ACC CAT         707
Gly Glu Asp Glu His Pro Gln Cys Leu Asn Ser Gln Pro Arg Thr His
160                 165                 170                 175

GGG TGG TCC CGG GCC ATC TTC TCT GTG GGC CCC GTG AGC CCG AGT CGC         755
Gly Trp Ser Arg Ala Ile Phe Ser Val Gly Pro Val Ser Pro Ser Arg
                    180                 185                 190

AGG TGG TCG TAC AGG TGC TAT GCT TAT GAC TCG AAC TCT CCC CAT GTG         803
Arg Trp Ser Tyr Arg Cys Tyr Ala Tyr Asp Ser Asn Ser Pro His Val
                195                 200                 205

TGG TCT CTA CCC AGT GAT CTC CTG GAG CTC CTG GTC CTA GGT GTT TCT         851
Trp Ser Leu Pro Ser Asp Leu Leu Glu Leu Leu Val Leu Gly Val Ser
        210                 215                 220

AAG AAG CCA TCA CTC TCA GTG CAG CCA GGT CCT ATA GTG GCC CCT GGG         899
Lys Lys Pro Ser Leu Ser Val Gln Pro Gly Pro Ile Val Ala Pro Gly
        225                 230                 235

GAG AGC CTG ACC CTC CAG TGT GTT TCT GAT GTC AGC TAC GAC AGA TTT         947
Glu Ser Leu Thr Leu Gln Cys Val Ser Asp Val Ser Tyr Asp Arg Phe
240                 245                 250                 255

GTT CTG TAT AAG GAG GGA GAA CGT GAC TTC CTC CAG CTC CCT GGC CCA         995
Val Leu Tyr Lys Glu Gly Glu Arg Asp Phe Leu Gln Leu Pro Gly Pro
                260                 265                 270

CAG CCC CAG GCT GGG CTC TCC CAG GCC AAC TTC ACC CTG GGC CCT GTG        1043
Gln Pro Gln Ala Gly Leu Ser Gln Ala Asn Phe Thr Leu Gly Pro Val
            275                 280                 285

AGC CGC TCC TAC GGG GGC CAG TAC AGA TGC TCC GGT GCA TAC AAC CTC        1091
Ser Arg Ser Tyr Gly Gly Gln Tyr Arg Cys Ser Gly Ala Tyr Asn Leu
        290                 295                 300

TCC TCC GAG TGG TCG GCC CCC AGC GAC CCC CTG GAC ATC CTG ATC GCA        1139
Ser Ser Glu Trp Ser Ala Pro Ser Asp Pro Leu Asp Ile Leu Ile Ala
        305                 310                 315

GGA CAG TTC CGT GGC AGA CCC TTC ATC TCG GTG CAT CCG GGC CCC ACG        1187
Gly Gln Phe Arg Gly Arg Pro Phe Ile Ser Val His Pro Gly Pro Thr
320                 325                 330                 335

GTG GCC TCA GGA GAG AAC GTG ACC CTG CTG TGT CAG TCA TGG GGG CCG        1235
Val Ala Ser Gly Glu Asn Val Thr Leu Leu Cys Gln Ser Trp Gly Pro
                340                 345                 350

TTC CAC ACT TTC CTT CTG ACC AAG GCG GGA GCA GCT GAT GCC CCC CTC        1283
Phe His Thr Phe Leu Leu Thr Lys Ala Gly Ala Ala Asp Ala Pro Leu
            355                 360                 365

CGT CTC AGA TCA ATA CAC GAA TAT CCT AAG TAC CAG GCT GAA TTC CCT        1331
Arg Leu Arg Ser Ile His Glu Tyr Pro Lys Tyr Gln Ala Glu Phe Pro
        370                 375                 380

ATG AGT CCT GTG ACC TCA GCC CAC TCG GGG ACC TAC AGG TGC TAC GGC        1379
Met Ser Pro Val Thr Ser Ala His Ser Gly Thr Tyr Arg Cys Tyr Gly
        385                 390                 395

TCA CTC AGC TCC AAC CCC TAC CTG CTG TCT CAC CCC AGT GAC TCC CTG        1427
Ser Leu Ser Ser Asn Pro Tyr Leu Leu Ser His Pro Ser Asp Ser Leu
400                 405                 410                 415

GAG CTC ATG GTC TCA GGA GCA GCT GAG ACC CTC AGC CCA CCA CAA AAC        1475
Glu Leu Met Val Ser Gly Ala Ala Glu Thr Leu Ser Pro Pro Gln Asn
                420                 425                 430

AAG TCC GAT TCC AAG GCT GGA GCA GCT AAC ACC CTC AGC CCA TCA CAA        1523
Lys Ser Asp Ser Lys Ala Gly Ala Ala Asn Thr Leu Ser Pro Ser Gln
            435                 440                 445

AAC AAG ACT GCC TCA CAC CCC CAG GAT TAC ACA GTG GAG AAT CTC ATC        1571
Asn Lys Thr Ala Ser His Pro Gln Asp Tyr Thr Val Glu Asn Leu Ile
        450                 455                 460
```

```
CGC ATG GGC ATA GCT GGC TTG GTC CTG GTG GTC CTC GGG ATT CTG CTA     1619
Arg Met Gly Ile Ala Gly Leu Val Leu Val Val Leu Gly Ile Leu Leu
    465                 470                 475

TTT GAG GCT CAG CAC AGC CAG AGA AGC CTC TGA GATGCAGCCG GGAGGTGAAC   1672
Phe Glu Ala Gln His Ser Gln Arg Ser Leu
480                 485

AGCAGAGAGA AGAATGTACC CTTCAGAGTG GTGGAGCCTT GGGAACAGAT CTGATGATGC   1732

CAGGAGGTTC CGGGAGACAA TTTAGGGCTG ATGTTATCTG GACTGTCTGC CAATCATTTT   1792

TAGAGGGAGG AATCAGTGTT GGATTGCAGA GACATTTTCT GGAGTGATCC ATGAAGGACC   1852

ATTAACATGT GATACCTTTC CTCTCTATTA ATGTTGACTT CCCTTGGTTG GATCCTCT    1910
```

(2) INFORMATION FOR SEQ ID NO: 14:

(i) SEQUENCE CHARACTERISTICS:
        (A) LENGTH: 489 amino acids
        (B) TYPE: amino acid
        (D) TOPOLOGY: linear (ii) MOLECULE TYPE: protein (xi) SEQUENCE DESCRIPTION: SEQ ID NO: 14:

```
Met Thr Pro Ile Val Thr Val Leu Ile Cys Leu Arg Leu Ser Leu Gly
 1               5                  10                  15

Pro Arg Thr His Val Gln Ala Gly Thr Leu Pro Lys Pro Thr Leu Trp
            20                  25                  30

Ala Glu Pro Gly Ser Val Ile Thr Gln Gly Ser Pro Val Thr Leu Trp
        35                  40                  45

Cys Gln Gly Ile Leu Glu Thr Gln Glu Tyr Arg Leu Tyr Arg Glu Lys
    50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Gly Glu
225                 230                 235                 240

Ser Leu Thr Leu Gln Cys Val Ser Asp Val Ser Tyr Asp Arg Phe Val
                245                 250                 255

Leu Tyr Lys Glu Gly Glu Arg Asp Phe Leu Gln Leu Pro Gly Pro Gln
            260                 265                 270
```

```
Pro Gln Ala Gly Leu Ser Gln Ala Asn Phe Thr Leu Gly Pro Val Ser
        275                 280                 285

Arg Ser Tyr Gly Gly Gln Tyr Arg Cys Ser Gly Ala Tyr Asn Leu Ser
    290                 295                 300

Ser Glu Trp Ser Ala Pro Ser Asp Pro Leu Asp Ile Leu Ile Ala Gly
305                 310                 315                 320

Gln Phe Arg Gly Arg Pro Phe Ile Ser Val His Pro Gly Pro Thr Val
                325                 330                 335

Ala Ser Gly Glu Asn Val Thr Leu Leu Cys Gln Ser Trp Gly Pro Phe
                340                 345                 350

His Thr Phe Leu Leu Thr Lys Ala Gly Ala Ala Asp Ala Pro Leu Arg
            355                 360                 365

Leu Arg Ser Ile His Glu Tyr Pro Lys Tyr Gln Ala Glu Phe Pro Met
    370                 375                 380

Ser Pro Val Thr Ser Ala His Ser Gly Thr Tyr Arg Cys Tyr Gly Ser
385                 390                 395                 400

Leu Ser Ser Asn Pro Tyr Leu Leu Ser His Pro Ser Asp Ser Leu Glu
                405                 410                 415

Leu Met Val Ser Gly Ala Ala Glu Thr Leu Ser Pro Pro Gln Asn Lys
            420                 425                 430

Ser Asp Ser Lys Ala Gly Ala Ala Asn Thr Leu Ser Pro Ser Gln Asn
    435                 440                 445

Lys Thr Ala Ser His Pro Gln Asp Tyr Thr Val Glu Asn Leu Ile Arg
450                 455                 460

Met Gly Ile Ala Gly Leu Val Leu Val Val Leu Gly Ile Leu Leu Phe
465                 470                 475                 480

Glu Ala Gln His Ser Gln Arg Ser Leu
                485
```

(2) INFORMATION FOR SEQ ID NO: 15:

(i) SEQUENCE CHARACTERISTICS:
        (A) LENGTH: 1725 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: pbmhh (ix) FEATURE:
        (A) NAME/KEY: CDS
        (B) LOCATION: 40..1488

(xi) SEQUENCE DESCRIPTION: SEQ ID NO: 15:

```
CTCATCCATC CGCAGAGCAG GGCAGTGGGA GGAGACGCC ATG ACC CCC ATC CTC        54
                                          Met Thr Pro Ile Leu
                                           1               5

ACG GTC CTG ATC TGT CTC GGG CTG AGT CTG GGC CCC AGG ACC CAC GTG      102
Thr Val Leu Ile Cys Leu Gly Leu Ser Leu Gly Pro Arg Thr His Val
             10                  15                  20

CAG GCA GGG CAC CTC CCC AAG CCC ACC CTC TGG GCT GAG CCA GGC TCT      150
Gln Ala Gly His Leu Pro Lys Pro Thr Leu Trp Ala Glu Pro Gly Ser
         25                  30                  35

GTG ATC ATC CAG GGA AGT CCT GTG ACC CTC AGG TGT CAG GGG AGC CTT      198
Val Ile Ile Gln Gly Ser Pro Val Thr Leu Arg Cys Gln Gly Ser Leu
     40                  45                  50

CAG GCT GAG GAG TAC CAT CTA TAT AGG GAA AAC AAA TCA GCA TCC TGG      246
```

```
                                                    -continued

Gln Ala Glu Glu Tyr His Leu Tyr Arg Glu Asn Lys Ser Ala Ser Trp
     55                  60                  65

GTT AGA CGG ATA CAA GAG CCT GGG AAG AAT GGC CAG TTC CCC ATC CCA       294
Val Arg Arg Ile Gln Glu Pro Gly Lys Asn Gly Gln Phe Pro Ile Pro
 70                  75                  80                  85

TCC ATC ACC TGG GAA CAC GCA GGG CGG TAT CAC TGT CAG TAC TAC AGC       342
Ser Ile Thr Trp Glu His Ala Gly Arg Tyr His Cys Gln Tyr Tyr Ser
                 90                  95                 100

CAC AAT CAC TCA TCA GAG TAC AGT GAC CCC CTG GAG CTG GTG GTG ACA       390
His Asn His Ser Ser Glu Tyr Ser Asp Pro Leu Glu Leu Val Val Thr
            105                 110                 115

GGA GCC TAC AGC AAA CCC ACC CTC TCA GCT CTG CCC AGC CCT GTG GTG       438
Gly Ala Tyr Ser Lys Pro Thr Leu Ser Ala Leu Pro Ser Pro Val Val
        120                 125                 130

ACC TTA GGA GGG AAC GTG ACC CTC CAG TGT GTC TCA CAG GTG GCA TTT       486
Thr Leu Gly Gly Asn Val Thr Leu Gln Cys Val Ser Gln Val Ala Phe
    135                 140                 145

GAC GGC TTC ATT CTG TGT AAG GAA GGA GAA GAT GAA CAC CCA CAA CGC       534
Asp Gly Phe Ile Leu Cys Lys Glu Gly Glu Asp Glu His Pro Gln Arg
150                 155                 160                 165

CTG AAC TCC CAT TCC CAT GCC CGT GGG TGG TCC TGG GCC ATC TTC TCC       582
Leu Asn Ser His Ser His Ala Arg Gly Trp Ser Trp Ala Ile Phe Ser
                170                 175                 180

GTG GGC CCC GTG AGC CCG AGT CGC AGG TGG TCG TAC AGG TGC TAT GCT       630
Val Gly Pro Val Ser Pro Ser Arg Arg Trp Ser Tyr Arg Cys Tyr Ala
            185                 190                 195

TAT GAC TCG AAC TCT CCC TAT GTG TGG TCT CTA CCC AGT GAT CTC CTG       678
Tyr Asp Ser Asn Ser Pro Tyr Val Trp Ser Leu Pro Ser Asp Leu Leu
        200                 205                 210

GAG CTC CTG GTC CCA GGT GTT TCT AAG AAG CCA TCA CTC TCA GTG CAG       726
Glu Leu Leu Val Pro Gly Val Ser Lys Lys Pro Ser Leu Ser Val Gln
    215                 220                 225

CCA GGT CCT ATG GTG GCC CCC GGG GAG AGC CTG ACC CTC CAG TGT GTC       774
Pro Gly Pro Met Val Ala Pro Gly Glu Ser Leu Thr Leu Gln Cys Val
230                 235                 240                 245

TCT GAT GTC GGC TAC GAC AGA TTT GTT CTG TAT AAG GAG GGA GAA CGT       822
Ser Asp Val Gly Tyr Asp Arg Phe Val Leu Tyr Lys Glu Gly Glu Arg
                250                 255                 260

GAC TTC CTC CAG CGC CCT GGT TGG CAG CCC CAG GCT GGG CTC TCC CAG       870
Asp Phe Leu Gln Arg Pro Gly Trp Gln Pro Gln Ala Gly Leu Ser Gln
            265                 270                 275

GCC AAC TTC ACC CTG GGC CCT GTG AGC CCC TCC CAC GGG GGC CAG TAC       918
Ala Asn Phe Thr Leu Gly Pro Val Ser Pro Ser His Gly Gly Gln Tyr
        280                 285                 290

AGA TGC TAC AGT GCA CAC AAC CTC TCC TCC GAG TGG TCG GCC CCC AGT       966
Arg Cys Tyr Ser Ala His Asn Leu Ser Ser Glu Trp Ser Ala Pro Ser
    295                 300                 305

GAC CCC CTG GAC ATC CTG ATC ACA GGA CAG TTC TAT GAC AGA CCC TCT      1014
Asp Pro Leu Asp Ile Leu Ile Thr Gly Gln Phe Tyr Asp Arg Pro Ser
310                 315                 320                 325

CTC TCG GTG CAG CCG GTC CCC ACA GTA GCC CCA GGA AAG AAC GTG ACC      1062
Leu Ser Val Gln Pro Val Pro Thr Val Ala Pro Gly Lys Asn Val Thr
                330                 335                 340

CTG CTG TGT CAG TCA CGG GGG CAG TTC CAC ACT TTC CTT CTG ACC AAG      1110
Leu Leu Cys Gln Ser Arg Gly Gln Phe His Thr Phe Leu Leu Thr Lys
            345                 350                 355

GAG GGG GCA GGC CAT CCC CCA CTG CAT CTG AGA TCA GAG CAC CAA GCT      1158
Glu Gly Ala Gly His Pro Pro Leu His Leu Arg Ser Glu His Gln Ala
        360                 365                 370
```

-continued

```
CAG CAG AAC CAG GCT GAA TTC CGC ATG GGT CCT GTG ACC TCA GCC CAC      1206
Gln Gln Asn Gln Ala Glu Phe Arg Met Gly Pro Val Thr Ser Ala His
        375                 380                 385

GTG GGG ACC TAC AGA TGC TAC AGC TCA CTC AGC TCC AAC CCC TAC CTG      1254
Val Gly Thr Tyr Arg Cys Tyr Ser Ser Leu Ser Ser Asn Pro Tyr Leu
390                 395                 400                 405

CTG TCT CTC CCC AGT GAC CCC CTG GAG CTC GTG GTC TCA GAA GCA GCT      1302
Leu Ser Leu Pro Ser Asp Pro Leu Glu Leu Val Val Ser Glu Ala Ala
                410                 415                 420

GAG ACC CTC AGC CCA TCA CAA AAC AAG ACA GAC TCC ACG ACT ACA TCC      1350
Glu Thr Leu Ser Pro Ser Gln Asn Lys Thr Asp Ser Thr Thr Thr Ser
            425                 430                 435

CTA GGC CAA CAC CCC CAG GAT TAC ACA GTG GAG AAT CTC ATC CGC ATG      1398
Leu Gly Gln His Pro Gln Asp Tyr Thr Val Glu Asn Leu Ile Arg Met
        440                 445                 450

GGT GTG GCT GGC TTG GTC CTG GTG GTC CTC GGG ATT CTG CTA TTT GAG      1446
Gly Val Ala Gly Leu Val Leu Val Val Leu Gly Ile Leu Leu Phe Glu
455                 460                 465

GCT CAG CAC AGC CAG AGA AGC CTA CAA GAT GCA GCC GGG AGG TGA          1491
Ala Gln His Ser Gln Arg Ser Leu Gln Asp Ala Ala Gly Arg
470                 475                 480

ACAGCAGAGA GGACAATGCA TCCTTCAGCG TGGTGGAGCC TCAGGACAG ATCTGATGAT     1551

CCCAGGAGGC TCTGGAGGAC AATCTAGGAC CTACATTATC TGGACTGTAT GCTGGTCATT    1611

TCTAGAGACA GCAATCAATA TTTGAGTGTA AGGAAACTGT CTGGGGTGAT TCCTAGAAGA    1671

TCATTAAACT GTGGTACATT TTTTTGTCTA AAAAGCAGGT CGTCTCGTTC CAAG          1725

(2) INFORMATION FOR SEQ ID NO: 16:

(i) SEQUENCE CHARACTERISTICS:
        (A) LENGTH: 483 amino acids
        (B) TYPE: amino acid
        (D) TOPOLOGY: linear (ii) MOLECULE TYPE: protein (xi) SEQUENCE DESCRIPTION: SEQ ID NO: 16:

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Ile Gln Gly Ser Pro Val Thr Leu Arg
        35                  40                  45

Cys Gln Gly Ser Leu Gln Ala Glu Glu Tyr His Leu Tyr Arg Glu Asn
    50                  55                  60

Lys Ser Ala Ser Trp Val Arg Arg Ile Gln Glu Pro Gly Lys Asn Gly
65                  70                  75                  80

Gln Phe Pro Ile Pro Ser Ile Thr Trp Glu His Ala Gly Arg Tyr His
                85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
```

-continued

```
                165                 170                 175
Trp Ala Ile Phe Ser Val Gly Pro Val Ser Pro Arg Arg Trp Ser
            180                 185                 190
Tyr Arg Cys Tyr Ala Tyr Asp Ser Asn Ser Pro Tyr Val Trp Ser Leu
            195                 200                 205
Pro Ser Asp Leu Leu Glu Leu Leu Val Pro Gly Val Ser Lys Lys Pro
            210                 215                 220
Ser Leu Ser Val Gln Pro Gly Pro Met Val Ala Pro Gly Glu Ser Leu
225                 230                 235                 240
Thr Leu Gln Cys Val Ser Asp Val Gly Tyr Asp Arg Phe Val Leu Tyr
            245                 250                 255
Lys Glu Gly Glu Arg Asp Phe Leu Gln Arg Pro Gly Trp Gln Pro Gln
            260                 265                 270
Ala Gly Leu Ser Gln Ala Asn Phe Thr Leu Gly Pro Val Ser Pro Ser
            275                 280                 285
His Gly Gly Gln Tyr Arg Cys Tyr Ser Ala His Asn Leu Ser Ser Glu
            290                 295                 300
Trp Ser Ala Pro Ser Asp Pro Leu Asp Ile Leu Ile Thr Gly Gln Phe
305                 310                 315                 320
Tyr Asp Arg Pro Ser Leu Ser Val Gln Pro Val Pro Thr Val Ala Pro
            325                 330                 335
Gly Lys Asn Val Thr Leu Leu Cys Gln Ser Arg Gly Gln Phe His Thr
            340                 345                 350
Phe Leu Leu Thr Lys Glu Gly Ala Gly His Pro Pro Leu His Leu Arg
            355                 360                 365
Ser Glu His Gln Ala Gln Gln Asn Gln Ala Glu Phe Arg Met Gly Pro
            370                 375                 380
Val Thr Ser Ala His Val Gly Thr Tyr Arg Cys Tyr Ser Ser Leu Ser
385                 390                 395                 400
Ser Asn Pro Tyr Leu Leu Ser Leu Pro Ser Asp Pro Leu Glu Leu Val
            405                 410                 415
Val Ser Glu Ala Ala Glu Thr Leu Ser Pro Ser Gln Asn Lys Thr Asp
            420                 425                 430
Ser Thr Thr Thr Ser Leu Gly Gln His Pro Gln Asp Tyr Thr Val Glu
            435                 440                 445
Asn Leu Ile Arg Met Gly Val Ala Gly Leu Val Leu Val Val Leu Gly
            450                 455                 460
Ile Leu Leu Phe Glu Ala Gln His Ser Gln Arg Ser Leu Gln Asp Ala
465                 470                 475                 480
Ala Gly Arg
```

(2) INFORMATION FOR SEQ ID NO: 17:

(i) SEQUENCE CHARACTERISTICS:
  (A) LENGTH: 1625 base pairs
  (B) TYPE: nucleic acid
  (C) STRANDEDNESS: single
  (D) TOPOLOGY: linear (ii) MOLECULE TYPE: cDNA (vii) IMMEDIATE SOURCE:
  (B) CLONE: pbm2

(ix) FEATURE:
  (A) NAME/KEY: CDS
  (B) LOCATION: 30..1373

(xi) SEQUENCE DESCRIPTION: SEQ ID NO: 17:

```
CACAGCTGGG GCCCCTGGGA GGAGACGCC ATG ATC CCC ACC TTC ACG GCT CTG        53
                                Met Ile Pro Thr Phe Thr Ala Leu
                                  1               5

CTC TGC CTC GGG CTG AGT CTG GGC CCC AGG ACC CAC ATG CAG GCA GGG       101
Leu Cys Leu Gly Leu Ser Leu Gly Pro Arg Thr His Met Gln Ala Gly
         10              15                  20

CCC CTC CCC AAA CCC ACC CTC TGG GCT GAG CCA GGC TCT GTG ATC AGC       149
Pro Leu Pro Lys Pro Thr Leu Trp Ala Glu Pro Gly Ser Val Ile Ser
 25              30                  35                      40

TGG GGG AAC TCT GTG ACC ATC TGG TGT CAG GGG ACC CTG GAG GCT CGG       197
Trp Gly Asn Ser Val Thr Ile Trp Cys Gln Gly Thr Leu Glu Ala Arg
                 45                  50                  55

GAG TAC CGT CTG GAT AAA GAG GAA AGC CCA GCA CCC TGG GAC AGA CAG       245
Glu Tyr Arg Leu Asp Lys Glu Glu Ser Pro Ala Pro Trp Asp Arg Gln
             60                  65                  70

AAC CCA CTG GAG CCC AAG AAC AAG GCC AGA TTC TCC ATC CCA TCC ATG       293
Asn Pro Leu Glu Pro Lys Asn Lys Ala Arg Phe Ser Ile Pro Ser Met
             75                  80                  85

ACA GAG GAC TAT GCA GGG AGA TAC CGC TGT TAC TAT CGC AGC CCT GTA       341
Thr Glu Asp Tyr Ala Gly Arg Tyr Arg Cys Tyr Tyr Arg Ser Pro Val
         90                  95                 100

GGC TGG TCA CAG CCC AGT GAC CCC CTG GAG CTG GTG ATG ACA GGA GCC       389
Gly Trp Ser Gln Pro Ser Asp Pro Leu Glu Leu Val Met Thr Gly Ala
105             110                 115                 120

TAC AGT AAA CCC ACC CTT TCA GCC CTG CCG AGT CCT CTT GTG ACC TCA       437
Tyr Ser Lys Pro Thr Leu Ser Ala Leu Pro Ser Pro Leu Val Thr Ser
                125                 130                 135

GGA AAG AGC GTG ACC CTG CTG TGT CAG TCA CGG AGC CCA ATG GAC ACT       485
Gly Lys Ser Val Thr Leu Leu Cys Gln Ser Arg Ser Pro Met Asp Thr
                140                 145                 150

TTT CTT CTG ATC AAG GAG CGG GCA GCC CAT CCC CTA CTG CAT CTG AGA       533
Phe Leu Leu Ile Lys Glu Arg Ala Ala His Pro Leu Leu His Leu Arg
                155                 160                 165

TCA GAG CAC GGA GCT CAG CAG CAC CAG GCT GAA TTC CCC ATG AGT CCT       581
Ser Glu His Gly Ala Gln Gln His Gln Ala Glu Phe Pro Met Ser Pro
    170                 175                 180

GTG ACC TCA GTG CAC GGG GGG ACC TAC AGG TGC TTC AGC TCA CAC GGC       629
Val Thr Ser Val His Gly Gly Thr Tyr Arg Cys Phe Ser Ser His Gly
185                 190                 195                 200

TTC TCC CAC TAC CTG CTG TCA CAC CCC AGT GAC CCC CTG GAG CTC ATA       677
Phe Ser His Tyr Leu Leu Ser His Pro Ser Asp Pro Leu Glu Leu Ile
                205                 210                 215

GTC TCA GGA TCC TTG GAG GGT CCC AGG CCC TCA CCC ACA AGG TCC GTC       725
Val Ser Gly Ser Leu Glu Gly Pro Arg Pro Ser Pro Thr Arg Ser Val
                220                 225                 230

TCA ACA GCT GCA GGC CCT GAG GAC CAG CCC CTC ATG CCT ACA GGG TCA       773
Ser Thr Ala Ala Gly Pro Glu Asp Gln Pro Leu Met Pro Thr Gly Ser
                235                 240                 245

GTC CCC CAC AGT GGT CTG AGA AGG CAC TGG GAG GTA CTG ATC GGG GTC       821
Val Pro His Ser Gly Leu Arg Arg His Trp Glu Val Leu Ile Gly Val
        250                 255                 260

TTG GTG GTC TCC ATC CTG CTT CTC TCC CTC CTC CTC TTC CTC CTC CTC       869
Leu Val Val Ser Ile Leu Leu Leu Ser Leu Leu Leu Phe Leu Leu Leu
265                 270                 275                 280

CAA CAC TGG CGT CAG GGA AAA CAC AGG ACA TTG GCC CAG AGA CAG GCT       917
Gln His Trp Arg Gln Gly Lys His Arg Thr Leu Ala Gln Arg Gln Ala
                285                 290                 295
```

```
                                          -continued

GAT TTC CAA CGT CCT CCA GGG GCT GCC GAG CCA GAG CCC AAG GAC GGG      965
Asp Phe Gln Arg Pro Pro Gly Ala Ala Glu Pro Glu Pro Lys Asp Gly
            300                 305                 310

GGC CTA CAG AGG AGG TCC AGC CCA GCT GCT GAC GTC CAG GGA GAA AAC     1013
Gly Leu Gln Arg Arg Ser Ser Pro Ala Ala Asp Val Gln Gly Glu Asn
            315                 320                 325

TTC TGT GCT GCC GTG AAG AAC ACA CAG CCT GAG GAC GGG GTG GAA ATG     1061
Phe Cys Ala Ala Val Lys Asn Thr Gln Pro Glu Asp Gly Val Glu Met
330                 335                 340

GAC ACT CGG CAG AGC CCA CAC GAT GAA GAC CCC CAG GCA GTG ACG TAT     1109
Asp Thr Arg Gln Ser Pro His Asp Glu Asp Pro Gln Ala Val Thr Tyr
345                 350                 355                 360

GCC AAG GTG AAA CAC TCC AGA CCT AGG AGA GAA ATG GCC TCT CCT CCC     1157
Ala Lys Val Lys His Ser Arg Pro Arg Arg Glu Met Ala Ser Pro Pro
                365                 370                 375

TCC CCA CTG TCT GGG GAA TTC CTG GAC ACA AAG GAC AGA CAG GCA GAA     1205
Ser Pro Leu Ser Gly Glu Phe Leu Asp Thr Lys Asp Arg Gln Ala Glu
            380                 385                 390

GAG GAC AGA CAG ATG GAC ACT GAG GCT GCT GCA TCT GAA GCC CCC CAG     1253
Glu Asp Arg Gln Met Asp Thr Glu Ala Ala Ala Ser Glu Ala Pro Gln
            395                 400                 405

GAT GTG ACC TAC GCC CGG CTG CAC AGC TTT ACC CTC AGA CAG AAG GCA     1301
Asp Val Thr Tyr Ala Arg Leu His Ser Phe Thr Leu Arg Gln Lys Ala
            410                 415                 420

ACT GAG CCT CCT CCA TCC CAG GAA GGG GCC TCT CCA GCT GAG CCC AGT     1349
Thr Glu Pro Pro Pro Ser Gln Glu Gly Ala Ser Pro Ala Glu Pro Ser
425                 430                 435                 440

GTC TAT GCC ACT CTG GCC ATC CAC TAA TCCAGGGGGG ACCCAGACCC           1396
Val Tyr Ala Thr Leu Ala Ile His
                445

CACAAGCCAT GGAGACTCAG GACCCCAGAA GGCATGGAAG CTGCCTCCAG TAGACATCAC   1456

TGAACCCCAG CCAGCCCAGA CCCCTGACAC AGACCACTAG AAGATTCCGG GAACGTTGGG   1516

AGTCACCTGA TTCTGCAAAG ATAAATAATA TCCCTGCATT ATCAAAATAA AGTAGCAGAC   1576

CTCTCAATTC ACAATGAGTT AACTGATAAA ACAAAACAGA AGTCAAAAA               1625

(2) INFORMATION FOR SEQ ID NO: 18:

(i) SEQUENCE CHARACTERISTICS:
        (A) LENGTH: 448 amino acids
        (B) TYPE: amino acid
        (D) TOPOLOGY: linear (ii) MOLECULE TYPE: protein (xi) SEQUENCE DESCRIPTION: SEQ ID NO: 18:

Met Ile Pro Thr Phe Thr Ala Leu Leu Cys Leu Gly Leu Ser Leu Gly
 1               5                  10                  15

Pro Arg Thr His Met Gln Ala Gly Pro Leu Pro Lys Pro Thr Leu Trp
                20                  25                  30

Ala Glu Pro Gly Ser Val Ile Ser Trp Gly Asn Ser Val Thr Ile Trp
            35                  40                  45

Cys Gln Gly Thr Leu Glu Ala Arg Glu Tyr Arg Leu Asp Lys Glu Glu
        50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
```

```
                100             105             110
Leu Glu Leu Val Met Thr Gly Ala Tyr Ser Lys Pro Thr Leu Ser Ala
        115                 120                 125
Leu Pro Ser Pro Leu Val Thr Ser Gly Lys Ser Val Thr Leu Leu Cys
130                 135                 140
Gln Ser Arg Ser Pro Met Asp Thr Phe Leu Leu Ile Lys Glu Arg Ala
145                 150                 155                 160
Ala His Pro Leu Leu His Leu Arg Ser Glu His Gly Ala Gln Gln His
                165                 170                 175
Gln Ala Glu Phe Pro Met Ser Pro Val Thr Ser Val His Gly Gly Thr
        180                 185                 190
Tyr Arg Cys Phe Ser Ser His Gly Phe Ser His Tyr Leu Leu Ser His
        195                 200                 205
Pro Ser Asp Pro Leu Glu Leu Ile Val Ser Gly Ser Leu Glu Gly Pro
210                 215                 220
Arg Pro Ser Pro Thr Arg Ser Val Ser Thr Ala Ala Gly Pro Glu Asp
225                 230                 235                 240
Gln Pro Leu Met Pro Thr Gly Ser Val Pro His Ser Gly Leu Arg Arg
                245                 250                 255
His Trp Glu Val Leu Ile Gly Val Leu Val Val Ser Ile Leu Leu Leu
                260                 265                 270
Ser Leu Leu Leu Phe Leu Leu Leu Gln His Trp Arg Gln Gly Lys His
        275                 280                 285
Arg Thr Leu Ala Gln Arg Gln Ala Asp Phe Gln Arg Pro Pro Gly Ala
        290                 295                 300
Ala Glu Pro Glu Pro Lys Asp Gly Gly Leu Gln Arg Arg Ser Ser Pro
305                 310                 315                 320
Ala Ala Asp Val Gln Gly Glu Asn Phe Cys Ala Ala Val Lys Asn Thr
                325                 330                 335
Gln Pro Glu Asp Gly Val Glu Met Asp Thr Arg Gln Ser Pro His Asp
                340                 345                 350
Glu Asp Pro Gln Ala Val Thr Tyr Ala Lys Val Lys His Ser Arg Pro
                355                 360                 365
Arg Arg Glu Met Ala Ser Pro Pro Ser Pro Leu Ser Gly Glu Phe Leu
370                 375                 380
Asp Thr Lys Asp Arg Gln Ala Glu Glu Asp Arg Gln Met Asp Thr Glu
385                 390                 395                 400
Ala Ala Ala Ser Glu Ala Pro Gln Asp Val Thr Tyr Ala Arg Leu His
                405                 410                 415
Ser Phe Thr Leu Arg Gln Lys Ala Thr Glu Pro Pro Pro Ser Gln Glu
                420                 425                 430
Gly Ala Ser Pro Ala Glu Pro Ser Val Tyr Ala Thr Leu Ala Ile His
        435                 440                 445
```

(2) INFORMATION FOR SEQ ID NO: 19:

(i) SEQUENCE CHARACTERISTICS:
        (A) LENGTH: 2194 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: pbm17

(ix) FEATURE:
        (A) NAME/KEY: CDS
        (B) LOCATION: 67..1959

(xi) SEQUENCE DESCRIPTION: SEQ ID NO: 19:

```
TCTCTGTCCT GCCAGCACTG AGGGCTCATC CCTCTGCAGA GCGCGGGGTC ACCGGAAGGA      60

GACGCC ATG ACG CCC GCC CTC ACA GCC CTG CTC TGC CTT GGG CTG AGT        108
       Met Thr Pro Ala Leu Thr Ala Leu Leu Cys Leu Gly Leu Ser
         1               5                  10

CTG GGC CCC AGG ACC CGC GTG CAG GCA GGG CCC TTC CCC AAA CCC ACC        156
Leu Gly Pro Arg Thr Arg Val Gln Ala Gly Pro Phe Pro Lys Pro Thr
 15              20                  25                  30

CTC TGG GCT GAG CCA GGC TCT GTG ATC AGC TGG GGG AGC CCC GTG ACC        204
Leu Trp Ala Glu Pro Gly Ser Val Ile Ser Trp Gly Ser Pro Val Thr
                 35                  40                  45

ATC TGG TGT CAG GGG AGC CTG GAG GCC CAG GAG TAC CAA CTG GAT AAA        252
Ile Trp Cys Gln Gly Ser Leu Glu Ala Gln Glu Tyr Gln Leu Asp Lys
                 50                  55                  60

GAG GGA AGC CCA GAG CCC TTG GAC AGA AAT AAC CCA CTG GAA CCC AAG        300
Glu Gly Ser Pro Glu Pro Leu Asp Arg Asn Asn Pro Leu Glu Pro Lys
 65                  70                  75

AAC AAG GCC AGA TTC TCC ATC CCA TCC ATG ACA CAG CAC CAT GCA GGG        348
Asn Lys Ala Arg Phe Ser Ile Pro Ser Met Thr Gln His His Ala Gly
 80                  85                  90

AGA TAC CGC TGC CAC TAT TAC AGC TCT GCA GGC TGG TCA GAG CCC AGC        396
Arg Tyr Arg Cys His Tyr Tyr Ser Ser Ala Gly Trp Ser Glu Pro Ser
 95                 100                 105                 110

GAC CCC CTG GAG CTG GTG ATG ACA GGA GCC TAT AGC AAA CCC ACC CTC        444
Asp Pro Leu Glu Leu Val Met Thr Gly Ala Tyr Ser Lys Pro Thr Leu
                115                 120                 125

TCA GCC CTG CCC AGC CCT GTG GTG GCC TCA GGG GGG AAT ATG ACC CTC        492
Ser Ala Leu Pro Ser Pro Val Val Ala Ser Gly Gly Asn Met Thr Leu
                130                 135                 140

CGA TGT GGC TCA CAG AAG AGA TAT CAC CAT TTT GTT CTG ATG AAG GAA        540
Arg Cys Gly Ser Gln Lys Arg Tyr His His Phe Val Leu Met Lys Glu
                145                 150                 155

GGA GAA CAC CAG CTC CCC CGG ACC CTG GAC TCA CAG CAG CTC CAC AGT        588
Gly Glu His Gln Leu Pro Arg Thr Leu Asp Ser Gln Gln Leu His Ser
160                 165                 170

GGG GGG TTC CAG GCC CTG TTC CCT GTG GGC CCC GTG AAC CCC AGC CAC        636
Gly Gly Phe Gln Ala Leu Phe Pro Val Gly Pro Val Asn Pro Ser His
175                 180                 185                 190

AGG TGG AGG TTC ACA TGC TAT TAC TAT TAT ATG AAC ACC CCC CGG GTG        684
Arg Trp Arg Phe Thr Cys Tyr Tyr Tyr Tyr Met Asn Thr Pro Arg Val
                195                 200                 205

TGG TCC CAC CCC AGT GAC CCC CTG GAG ATT CTG CCC TCA GGC GTG TCT        732
Trp Ser His Pro Ser Asp Pro Leu Glu Ile Leu Pro Ser Gly Val Ser
                210                 215                 220

AGG AAG CCC TCC CTC CTG ACC CTG CAG GGC CCT GTC CTG GCC CCT GGG        780
Arg Lys Pro Ser Leu Leu Thr Leu Gln Gly Pro Val Leu Ala Pro Gly
                225                 230                 235

CAG AGT CTG ACC CTC CAG TGT GGC TCT GAT GTC GGC TAC GAC AGA TTT        828
Gln Ser Leu Thr Leu Gln Cys Gly Ser Asp Val Gly Tyr Asp Arg Phe
240                 245                 250

GTT CTG TAT AAG GAG GGG GAA CGT GAC TTC CTC CAG CGC CCT GGC CAG        876
Val Leu Tyr Lys Glu Gly Glu Arg Asp Phe Leu Gln Arg Pro Gly Gln
255                 260                 265                 270

CAG CCC CAG GCT GGG CTC TCC CAG GCC AAC TTC ACC CTG GGC CCT GTG        924
Gln Pro Gln Ala Gly Leu Ser Gln Ala Asn Phe Thr Leu Gly Pro Val
                275                 280                 285
```

-continued

| | |
|---|---|
| AGC CCC TCC AAT GGG GGC CAG TAC AGG TGC TAC GGT GCA CAC AAC CTC<br>Ser Pro Ser Asn Gly Gly Gln Tyr Arg Cys Tyr Gly Ala His Asn Leu<br>290                  295                  300 | 972 |
| TCC TCC GAG TGG TCG GCC CCC AGC GAC CCC CTG AAC ATC CTG ATG GCA<br>Ser Ser Glu Trp Ser Ala Pro Ser Asp Pro Leu Asn Ile Leu Met Ala<br>305                    310                  315 | 1020 |
| GGA CAG ATC TAT GAC ACC GTC TCC CTG TCA GCA CAG CCG GGC CCC ACA<br>Gly Gln Ile Tyr Asp Thr Val Ser Leu Ser Ala Gln Pro Gly Pro Thr<br>320                  325                  330 | 1068 |
| GTG GCC TCA GGA GAG AAC GTG ACC CTG CTG TGT CAG TCA TGG TGG CAG<br>Val Ala Ser Gly Glu Asn Val Thr Leu Leu Cys Gln Ser Trp Trp Gln<br>335                    340                  345                  350 | 1116 |
| TTT GAC ACT TTC CTT CTG ACC AAA GAA GGG GCA GCC CAT CCC CCA CTG<br>Phe Asp Thr Phe Leu Leu Thr Lys Glu Gly Ala Ala His Pro Pro Leu<br>                  355                  360                  365 | 1164 |
| CGT CTG AGA TCA ATG TAC GGA GCT CAT AAG TAC CAG GCT GAA TTC CCC<br>Arg Leu Arg Ser Met Tyr Gly Ala His Lys Tyr Gln Ala Glu Phe Pro<br>          370                  375                  380 | 1212 |
| ATG AGT CCT GTG ACC TCA GCC CAC GCG GGG ACC TAC AGG TGC TAC GGC<br>Met Ser Pro Val Thr Ser Ala His Ala Gly Thr Tyr Arg Cys Tyr Gly<br>385                    390                  395 | 1260 |
| TCA CGC AGC TCC AAC CCC TAC CTG CTG TCT CAC CCC AGT GAG CCC CTG<br>Ser Arg Ser Ser Asn Pro Tyr Leu Leu Ser His Pro Ser Glu Pro Leu<br>400                    405                  410 | 1308 |
| GAG CTC GTG GTC TCA GGA CAC TCT GGA GGC TCC AGC CTC CCA CCC ACA<br>Glu Leu Val Val Ser Gly His Ser Gly Gly Ser Ser Leu Pro Pro Thr<br>415                    420                  425                  430 | 1356 |
| GGG CCG CCC TCC ACA CCT GGT CTG GGA AGA TAC CTG GAG GTT TTG ATT<br>Gly Pro Pro Ser Thr Pro Gly Leu Gly Arg Tyr Leu Glu Val Leu Ile<br>                  435                  440                  445 | 1404 |
| GGG GTC TCG GTG GCC TTC GTC CTG CTG CTC TTC CTC CTC TTC CTC<br>Gly Val Ser Val Ala Phe Val Leu Leu Leu Phe Leu Leu Leu Phe Leu<br>          450                  455                  460 | 1452 |
| CTC CTC CGA CGT CAG CGT CAC AGC AAA CAC AGG ACA TCT GAC CAG AGA<br>Leu Leu Arg Arg Gln Arg His Ser Lys His Arg Thr Ser Asp Gln Arg<br>          465                  470                  475 | 1500 |
| AAG ACT GAT TTC CAG CGT CCT GCA GGG GCT GCG GAG ACA GAG CCC AAG<br>Lys Thr Asp Phe Gln Arg Pro Ala Gly Ala Ala Glu Thr Glu Pro Lys<br>480                    485                  490 | 1548 |
| GAC AGG GGC CTG CTG AGG AGG TCC AGC CCA GCT GCT GAC GTC CAG GAA<br>Asp Arg Gly Leu Leu Arg Arg Ser Ser Pro Ala Ala Asp Val Gln Glu<br>495                    500                  505                  510 | 1596 |
| GAA AAC CTC TAT GCT GCC GTG AAG GAC ACA CAG TCT GAG GAC GGG GTG<br>Glu Asn Leu Tyr Ala Ala Val Lys Asp Thr Gln Ser Glu Asp Gly Val<br>                  515                  520                  525 | 1644 |
| GAG CTG GAC AGT CAG AGC CCA CAC GAT GAA GAC CCC CAC GCA GTG ACG<br>Glu Leu Asp Ser Gln Ser Pro His Asp Glu Asp Pro His Ala Val Thr<br>          530                  535                  540 | 1692 |
| TAT GCC CCG GTG AAA CAC TCC AGT CCT AGG AGA GAA ATG GCC TCT CCT<br>Tyr Ala Pro Val Lys His Ser Ser Pro Arg Arg Glu Met Ala Ser Pro<br>          545                  550                  555 | 1740 |
| CCT TCC CCA CTG TCT GGG GAA TTC CTG GAC ACA AAG GAC AGA CAG GCA<br>Pro Ser Pro Leu Ser Gly Glu Phe Leu Asp Thr Lys Asp Arg Gln Ala<br>560                    565                  570 | 1788 |
| GAA GAG GAC AGA CAG ATG GAC ACT GAG GCT GCT GCA TCT GAA GCC TCC<br>Glu Glu Asp Arg Gln Met Asp Thr Glu Ala Ala Ala Ser Glu Ala Ser<br>575                    580                  585                  590 | 1836 |
| CAG GAT GTG ACC TAC GCC CAG CTG CAC AGC TTG ACC CTT AGA CGG AAG<br>Gln Asp Val Thr Tyr Ala Gln Leu His Ser Leu Thr Leu Arg Arg Lys | 1884 |

```
                        595                 600                 605
GCA ACT GAG CCT CCT CCA TCC CAG GAA GGG GAA CCT CCA GCT GAG CCC        1932
Ala Thr Glu Pro Pro Pro Ser Gln Glu Gly Glu Pro Pro Ala Glu Pro
                610                 615                 620

AGC ATC TAC GCC ACT CTG GCC ATC CAC TAG CCCGGGGGGT ACGCAGACCC         1982
Ser Ile Tyr Ala Thr Leu Ala Ile His
            625                 630

CACACTCAGC AGAAGGAGAC TCAGGACTGC TGAAGGACGG GAGCTGCCCC CAGTGGACAC     2042

CAGTGAACCC CAGTCAGCCT GGACCCCTAA CACAGACCAT GAGGAGACGC TGGGAACTTG     2102

TGGGACTCAC CTGACTCAAA GATGACTAAT ATCGTCCCAT TTTGGAAATA AGCAACAGA     2162

CTTCTCAAGC AGGTCGTCTC GTTCCAAGAT CT                                   2194
```

(2) INFORMATION FOR SEQ ID NO: 20:

(i) SEQUENCE CHARACTERISTICS:
        (A) LENGTH: 631 amino acids
        (B) TYPE: amino acid
        (D) TOPOLOGY: linear (ii) MOLECULE TYPE: protein (xi) SEQUENCE DESCRIPTION: SEQ ID NO: 20:

```
Met Thr Pro Ala Leu Thr Ala Leu Leu Cys Leu Gly Leu Ser Leu Gly
 1               5                  10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
        35                  40                  45

Cys Gln Gly Ser Leu Glu Ala Gln Glu Tyr Gln Leu Asp Lys Glu Gly
     50                  55                  60

Ser Pro Glu Pro Leu Asp Arg Asn Asn Pro Leu Glu Pro Lys Asn Lys
 65                  70                  75                  80

Ala Arg Phe Ser Ile Pro Ser Met Thr Gln His His Ala Gly Arg Tyr
                85                  90                  95

Arg Cys His Tyr Tyr Ser Ser Ala Gly Trp Ser Glu Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Val Val Ala Ser Gly Gly Asn Met Thr Leu Arg Cys
    130                 135                 140

Gly Ser Gln Lys Arg Tyr His His Phe Val Leu Met Lys Glu Gly Glu
145                 150                 155                 160

His Gln Leu Pro Arg Thr Leu Asp Ser Gln Gln Leu His Ser Gly Gly
                165                 170                 175

Phe Gln Ala Leu Phe Pro Val Gly Pro Val Asn Pro Ser His Arg Trp
            180                 185                 190

Arg Phe Thr Cys Tyr Tyr Tyr Met Asn Thr Pro Arg Val Trp Ser
        195                 200                 205

His Pro Ser Asp Pro Leu Glu Ile Leu Pro Ser Gly Val Ser Arg Lys
    210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
                245                 250                 255

Tyr Lys Glu Gly Glu Arg Asp Phe Leu Gln Arg Pro Gly Gln Gln Pro
```

```
                  260                 265                 270
Gln Ala Gly Leu Ser Gln Ala Asn Phe Thr Leu Gly Pro Val Ser Pro
            275                 280                 285
Ser Asn Gly Gly Gln Tyr Arg Cys Tyr Gly Ala His Asn Leu Ser Ser
        290                 295                 300
Glu Trp Ser Ala Pro Ser Asp Pro Leu Asn Ile Leu Met Ala Gly Gln
305                 310                 315                 320
Ile Tyr Asp Thr Val Ser Leu Ser Ala Gln Pro Gly Pro Thr Val Ala
                325                 330                 335
Ser Gly Glu Asn Val Thr Leu Leu Cys Gln Ser Trp Trp Gln Phe Asp
            340                 345                 350
Thr Phe Leu Leu Thr Lys Glu Gly Ala Ala His Pro Pro Leu Arg Leu
        355                 360                 365
Arg Ser Met Tyr Gly Ala His Lys Tyr Gln Ala Glu Phe Pro Met Ser
    370                 375                 380
Pro Val Thr Ser Ala His Ala Gly Thr Tyr Arg Cys Tyr Gly Ser Arg
385                 390                 395                 400
Ser Ser Asn Pro Tyr Leu Leu Ser His Pro Ser Glu Pro Leu Glu Leu
                405                 410                 415
Val Val Ser Gly His Ser Gly Gly Ser Ser Leu Pro Pro Thr Gly Pro
            420                 425                 430
Pro Ser Thr Pro Gly Leu Gly Arg Tyr Leu Glu Val Leu Ile Gly Val
        435                 440                 445
Ser Val Ala Phe Val Leu Leu Leu Phe Leu Leu Leu Phe Leu Leu Leu
    450                 455                 460
Arg Arg Gln Arg His Ser Lys His Arg Thr Ser Asp Gln Arg Lys Thr
465                 470                 475                 480
Asp Phe Gln Arg Pro Ala Gly Ala Ala Glu Thr Glu Pro Lys Asp Arg
                485                 490                 495
Gly Leu Leu Arg Arg Ser Ser Pro Ala Ala Asp Val Gln Glu Glu Asn
            500                 505                 510
Leu Tyr Ala Ala Val Lys Asp Thr Gln Ser Glu Asp Gly Val Glu Leu
        515                 520                 525
Asp Ser Gln Ser Pro His Asp Glu Asp Pro His Ala Val Thr Tyr Ala
    530                 535                 540
Pro Val Lys His Ser Ser Pro Arg Arg Glu Met Ala Ser Pro Pro Ser
545                 550                 555                 560
Pro Leu Ser Gly Glu Phe Leu Asp Thr Lys Asp Arg Gln Ala Glu Glu
                565                 570                 575
Asp Arg Gln Met Asp Thr Glu Ala Ala Ala Ser Glu Ala Ser Gln Asp
            580                 585                 590
Val Thr Tyr Ala Gln Leu His Ser Leu Thr Leu Arg Arg Lys Ala Thr
        595                 600                 605
Glu Pro Pro Pro Ser Gln Glu Gly Glu Pro Pro Ala Glu Pro Ser Ile
    610                 615                 620
Tyr Ala Thr Leu Ala Ile His
625                 630

(2) INFORMATION FOR SEQ ID NO: 21:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear
```

```
    (ii) MOLECULE TYPE: cDNA (vii) IMMEDIATE SOURCE:
          (B) CLONE: pbmnew (ix) FEATURE:
         (A) NAME/KEY: CDS
         (B) LOCATION: 67..1833

(xi) SEQUENCE DESCRIPTION: SEQ ID NO: 21:

TTTGTGTCCT GCCAGGCACC GTGGTCTCAT CCGCCTGCAC AGCTGAGTCC AGTGGGAGCT        60

GACGCC ATG ACC CTC ACC CTC TCA GTC CTG ATT TGC CTC GGG CTG AGT         108
       Met Thr Leu Thr Leu Ser Val Leu Ile Cys Leu Gly Leu Ser
        1               5                  10

GTG GGC CCC AGG ACC TGC GTG CAG GCA GGC ACC CTC CCC AAA CCC ACC        156
Val Gly Pro Arg Thr Cys Val Gln Ala Gly Thr Leu Pro Lys Pro Thr
 15              20                  25                  30

CTC TGG GCT GAG CCA GCC TCT GTG ATA GCT CGG GGG AAG CCC GTG ACC        204
Leu Trp Ala Glu Pro Ala Ser Val Ile Ala Arg Gly Lys Pro Val Thr
                 35                  40                  45

CTC TGG TGT CAG GGG CCC CTG GAG ACT GAG GAG TAC CGT CTG GAT AAG        252
Leu Trp Cys Gln Gly Pro Leu Glu Thr Glu Glu Tyr Arg Leu Asp Lys
             50                  55                  60

GAG GGA CTC CCA TGG GCC CGG AAG AGA CAG AAC CCA CTG GAG CCT GGA        300
Glu Gly Leu Pro Trp Ala Arg Lys Arg Gln Asn Pro Leu Glu Pro Gly
             65                  70                  75

GCC AAG GCC AAG TTC CAC ATT CCA TCC ACG GTG TAT GAC AGT GCA GGG        348
Ala Lys Ala Lys Phe His Ile Pro Ser Thr Val Tyr Asp Ser Ala Gly
         80                  85                  90

CGA TAC CGC TGC TAC TAT GAG ACC CCT GCA GGC TGG TCA GAG CCC AGT        396
Arg Tyr Arg Cys Tyr Tyr Glu Thr Pro Ala Gly Trp Ser Glu Pro Ser
 95                 100                 105                 110

GAC CCC CTG GAG CTG GTG GCG ACA GGA TTC TAT GCA GAA CCC ACT CTT        444
Asp Pro Leu Glu Leu Val Ala Thr Gly Phe Tyr Ala Glu Pro Thr Leu
                 115                 120                 125

TTA GCC CTG CCG AGT CCT GTG GTG GCC TCA GGA GGA AAT GTG ACC CTC        492
Leu Ala Leu Pro Ser Pro Val Val Ala Ser Gly Gly Asn Val Thr Leu
             130                 135                 140

CAG TGT GAT ACA CTG GAC GGA CTT CTC ACG TTT GTT CTT GTT GAG GAA        540
Gln Cys Asp Thr Leu Asp Gly Leu Leu Thr Phe Val Leu Val Glu Glu
             145                 150                 155

GAA CAG AAG CTC CCC AGG ACC CTG TAC TCA CAG AAG CTC CCC AAA GGG        588
Glu Gln Lys Leu Pro Arg Thr Leu Tyr Ser Gln Lys Leu Pro Lys Gly
        160                 165                 170

CCA TCC CAG GCC CTG TTC CCT GTG GGT CCC GTG ACC CCC AGC TGC AGG        636
Pro Ser Gln Ala Leu Phe Pro Val Gly Pro Val Thr Pro Ser Cys Arg
175                 180                 185                 190

TGG AGG TTC AGA TGC TAT TAC TAT TAC AGG AAA AAC CCT CAG GTG TGG        684
Trp Arg Phe Arg Cys Tyr Tyr Tyr Tyr Arg Lys Asn Pro Gln Val Trp
                 195                 200                 205

TCG AAC CCC AGT GAC CTC CTG GAG ATT CTG GTC CCA GGC GTG TCT AGG        732
Ser Asn Pro Ser Asp Leu Leu Glu Ile Leu Val Pro Gly Val Ser Arg
             210                 215                 220

AAG CCC TCC CTC CTG ATC CCG CAG GGC TCT GTC GTG GCC CGC GGA GGC        780
Lys Pro Ser Leu Leu Ile Pro Gln Gly Ser Val Val Ala Arg Gly Gly
             225                 230                 235

AGC CTG ACC CTG CAG TGT CGC TCT GAT GTC GGC TAT GAC ATA TTC GTT        828
Ser Leu Thr Leu Gln Cys Arg Ser Asp Val Gly Tyr Asp Ile Phe Val
        240                 245                 250

CTG TAC AAG GAG GGG GAA CAT GAC CTC GTC CAG GGC TCT GGC CAG CAG        876
```

```
Leu Tyr Lys Glu Gly Glu His Asp Leu Val Gln Gly Ser Gly Gln Gln
255                 260                 265                 270

CCC CAG GCT GGG CTC TCC CAG GCC AAC TTC ACC CTG GGC CCT GTG AGC      924
Pro Gln Ala Gly Leu Ser Gln Ala Asn Phe Thr Leu Gly Pro Val Ser
                275                 280                 285

CGC TCC CAC GGG GGC CAG TAC AGA TGC TAC GGT GCA CAC AAC CTC TCC      972
Arg Ser His Gly Gly Gln Tyr Arg Cys Tyr Gly Ala His Asn Leu Ser
                290                 295                 300

CCT AGG TGG TCG GCC CCC AGC GAC CCC CTG GAC ATC CTG ATC GCA GGA     1020
Pro Arg Trp Ser Ala Pro Ser Asp Pro Leu Asp Ile Leu Ile Ala Gly
                305                 310                 315

CTG ATC CCT GAC ATA CCC GCC CTC TCG GTG CAG CCG GGC CCC AAG GTG     1068
Leu Ile Pro Asp Ile Pro Ala Leu Ser Val Gln Pro Gly Pro Lys Val
                320                 325                 330

GCC TCA GGA GAG AAC GTG ACC CTG CTG TGT CAG TCA TGG CAT CAG ATA     1116
Ala Ser Gly Glu Asn Val Thr Leu Leu Cys Gln Ser Trp His Gln Ile
335                 340                 345                 350

GAC ACT TTC TTT TTG ACC AAG GAG GGG GCA GCC CAT CCC CCG CTG TGT     1164
Asp Thr Phe Phe Leu Thr Lys Glu Gly Ala Ala His Pro Pro Leu Cys
                355                 360                 365

CTA AAG TCA AAG TAC CAG TCT TAT AGA CAC CAG GCT GAA TTC TCC ATG     1212
Leu Lys Ser Lys Tyr Gln Ser Tyr Arg His Gln Ala Glu Phe Ser Met
                370                 375                 380

AGT CCT GTG ACC TCA GCC CAG GGT GGA ACC TAC CGA TGC TAC AGC GCA     1260
Ser Pro Val Thr Ser Ala Gln Gly Gly Thr Tyr Arg Cys Tyr Ser Ala
                385                 390                 395

ATC AGG TCC TAC CCC TAC CTG CTG TCC AGC CCT AGT TAC CCC CAG GAG     1308
Ile Arg Ser Tyr Pro Tyr Leu Leu Ser Ser Pro Ser Tyr Pro Gln Glu
400                 405                 410

CTC GTG GTC TCA GGA CCC TCT GGG GAT CCC AGC CTC TCA CCT ACA GGC     1356
Leu Val Val Ser Gly Pro Ser Gly Asp Pro Ser Leu Ser Pro Thr Gly
415                 420                 425                 430

TCC ACC CCC ACA CCT GGC CCT GAG GAC CAG CCC CTC ACC CCC ACG GGG     1404
Ser Thr Pro Thr Pro Gly Pro Glu Asp Gln Pro Leu Thr Pro Thr Gly
                435                 440                 445

TTG GAT CCC CAG AGT GGT CTG GGA AGG CAC CTG GGG GTT GTG ACT GGG     1452
Leu Asp Pro Gln Ser Gly Leu Gly Arg His Leu Gly Val Val Thr Gly
                450                 455                 460

GTC TCA GTG GCC TTC GTC CTG CTG CTG TTC CTC CTC CTC TTC CTC CTC     1500
Val Ser Val Ala Phe Val Leu Leu Leu Phe Leu Leu Leu Phe Leu Leu
                465                 470                 475

CTC CGA CAT CGG CAT CAG AGC AAA CAC AGG ACA TCG GCC CAT TTC TAC     1548
Leu Arg His Arg His Gln Ser Lys His Arg Thr Ser Ala His Phe Tyr
                480                 485                 490

CGT CCT GCA GGG GCT GCG GGG CCA GAG CCC AAG GAC CAG GGC CTG CAG     1596
Arg Pro Ala Gly Ala Ala Gly Pro Glu Pro Lys Asp Gln Gly Leu Gln
495                 500                 505                 510

AAG AGG GCC AGC CCA GTT GCT GAC ATC CAG GAG GAA ATT CTC AAT GCT     1644
Lys Arg Ala Ser Pro Val Ala Asp Ile Gln Glu Glu Ile Leu Asn Ala
                515                 520                 525

GCC GTG AAG GAC ACA CAG CCC AAG GAC GGG GTG GAG ATG GAT GCT CGG     1692
Ala Val Lys Asp Thr Gln Pro Lys Asp Gly Val Glu Met Asp Ala Arg
                530                 535                 540

GCT GCT GCA TCT GAA GCC CCC CAG GAT GTG ACC TAC GCC CAG CTG CAC     1740
Ala Ala Ala Ser Glu Ala Pro Gln Asp Val Thr Tyr Ala Gln Leu His
                545                 550                 555

AGC TTG ACC CTC AGA CGG GAG GCA ACT GAG CCT CCT CCA TCC CAG GAA     1788
Ser Leu Thr Leu Arg Arg Glu Ala Thr Glu Pro Pro Pro Ser Gln Glu
                560                 565                 570
```

-continued

```
AGG GAA CCT CCA GCT GAA CCC AGC ATC TAC GCC CCC CTG GCC ATC CAC    1836
Arg Glu Pro Pro Ala Glu Pro Ser Ile Tyr Ala Pro Leu Ala Ile His
575                 580                 585                 590

TAG CCCACGGGGG ACCCAGATCT CATACTCAAC AGAAGGAGAC TCAGAGACTC         1889

CAGAAGGCAC AGGAGCTGCC CCCAGTGGAC ACCAATGAAC CCCAGCCAGC CTGGACCCCT  1949

AACAAAGACC ACCAGGACAT CCTGGGAACT CTGGGACTCA CTAGATTCTG CAGTCAAAGA  2009

TGACTAATAT CCTTGCATTT TTGAAATGAA GCCACAGACT TCTCAATAAA TC          2061
```

(2) INFORMATION FOR SEQ ID NO: 22:

(i) SEQUENCE CHARACTERISTICS:
        (A) LENGTH: 590 amino acids
        (B) TYPE: amino acid
        (D) TOPOLOGY: linear (ii) MOLECULE TYPE: protein (xi) SEQUENCE DESCRIPTION: SEQ ID NO: 22:

```
Met Thr Leu Thr Leu Ser Val Leu Ile Cys Leu Gly Leu Ser Val Gly
  1               5                  10                  15

Pro Arg Thr Cys Val Gln Ala Gly Thr Leu Pro Lys Pro Thr Leu Trp
             20                  25                  30

Ala Glu Pro Ala Ser Val Ile Ala Arg Gly Lys Pro Val Thr Leu Trp
         35                  40                  45

Cys Gln Gly Pro Leu Glu Thr Glu Glu Tyr Arg Leu Asp Lys Glu Gly
     50                  55                  60

Leu Pro Trp Ala Arg Lys Arg Gln Asn Pro Leu Glu Pro Gly Ala Lys
 65                  70                  75                  80

Ala Lys Phe His Ile Pro Ser Thr Val Tyr Asp Ser Ala Gly Arg Tyr
                 85                  90                  95

Arg Cys Tyr Tyr Glu Thr Pro Ala Gly Trp Ser Glu Pro Ser Asp Pro
            100                 105                 110

Leu Glu Leu Val Ala Thr Gly Phe Tyr Ala Glu Pro Thr Leu Leu Ala
        115                 120                 125

Leu Pro Ser Pro Val Val Ala Ser Gly Gly Asn Val Thr Leu Gln Cys
130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
                165                 170                 175

Gln Ala Leu Phe Pro Val Gly Pro Val Thr Pro Ser Cys Arg Trp Arg
            180                 185                 190

Phe Arg Cys Tyr Tyr Tyr Arg Lys Asn Pro Gln Val Trp Ser Asn
        195                 200                 205

Pro Ser Asp Leu Leu Glu Ile Leu Val Pro Gly Val Ser Arg Lys Pro
    210                 215                 220

Ser Leu Leu Ile Pro Gln Gly Ser Val Val Ala Arg Gly Gly Ser Leu
225                 230                 235                 240

Thr Leu Gln Cys Arg Ser Asp Val Gly Tyr Asp Ile Phe Val Leu Tyr
                245                 250                 255

Lys Glu Gly Glu His Asp Leu Val Gln Gly Ser Gly Gln Gln Pro Gln
            260                 265                 270

Ala Gly Leu Ser Gln Ala Asn Phe Thr Leu Gly Pro Val Ser Arg Ser
        275                 280                 285

His Gly Gly Gln Tyr Arg Cys Tyr Gly Ala His Asn Leu Ser Pro Arg
```

```
                    290                 295                 300
Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                    325                 330                 335

Gly Glu Asn Val Thr Leu Leu Cys Gln Ser Trp His Gln Ile Asp Thr
                    340                 345                 350

Phe Phe Leu Thr Lys Glu Gly Ala Ala His Pro Pro Leu Cys Leu Lys
                    355                 360                 365

Ser Lys Tyr Gln Ser Tyr Arg His Gln Ala Glu Phe Ser Met Ser Pro
370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                    405                 410                 415

Val Ser Gly Pro Ser Gly Asp Pro Ser Leu Ser Pro Thr Gly Ser Thr
                    420                 425                 430

Pro Thr Pro Gly Pro Glu Asp Gln Pro Leu Thr Pro Thr Gly Leu Asp
                    435                 440                 445

Pro Gln Ser Gly Leu Gly Arg His Leu Gly Val Val Thr Gly Val Ser
450                 455                 460

Val Ala Phe Val Leu Leu Leu Phe Leu Leu Leu Phe Leu Leu Leu Arg
465                 470                 475                 480

His Arg His Gln Ser Lys His Arg Thr Ser Ala His Phe Tyr Arg Pro
                    485                 490                 495

Ala Gly Ala Ala Gly Pro Glu Pro Lys Asp Gln Gly Leu Gln Lys Arg
                    500                 505                 510

Ala Ser Pro Val Ala Asp Ile Gln Glu Glu Ile Leu Asn Ala Ala Val
                    515                 520                 525

Lys Asp Thr Gln Pro Lys Asp Gly Val Glu Met Asp Ala Arg Ala Ala
530                 535                 540

Ala Ser Glu Ala Pro Gln Asp Val Thr Tyr Ala Gln Leu His Ser Leu
545                 550                 555                 560

Thr Leu Arg Arg Glu Ala Thr Glu Pro Pro Pro Ser Gln Glu Arg Glu
                    565                 570                 575

Pro Pro Ala Glu Pro Ser Ile Tyr Ala Pro Leu Ala Ile His
                    580                 585                 590
```

(2) INFORMATION FOR SEQ ID NO: 23:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Probe (xi) SEQUENCE DESCRIPTION: SEQ ID NO: 23:

TATGCGGCCG CCATGATGAC AATGTGGT                                28

(2) INFORMATION FOR SEQ ID NO: 24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Probe (xi) SEQUENCE DESCRIPTION: SEQ ID NO: 24:

TATGCGGCCG CCCCTTGCGA TAGCG                                          25

(2) INFORMATION FOR SEQ ID NO: 25:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO: 25:

ATAGTCGACA ACGCCATCAT GAGATGTGGT G                                   31

(2) INFORMATION FOR SEQ ID NO: 26:

(i) SEQUENCE CHARACTERISTICS:
            (A) LENGTH: 29 Nucleotides
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO: 26:

TAAAGATCTG GGCTCGTTAG CTGTCGGGT                                      29

(2) INFORMATION FOR SEQ ID NO: 27:

(i) SEQUENCE CHARACTERISTICS:
            (A) LENGTH: 33 nucleotides
            (B) TYPE: nucleic acid
            (C) STRANDEDNESS: single
            (D) TOPOLOGY: linear (ii) MOLECULE TYPE: Oligonucleotide (xi) SEQUENCE DESCRIPTION: SEQ ID NO: 27:

TATAGATCTA CCCCCAGGTG CCTTCCCAGA CCA                                 33

(2) INFORMATION FOR SEQ ID NO: 28:

(i) SEQUENCE CHARACTERISTICS:
            (A) LENGTH: 42 amino acids
            (B) TYPE: amino acid
            (D) TOPOLOGY: linear (ii) MOLECULE TYPE: peptide (xi) SEQUENCE DESCRIPTION: SEQ ID NO: 28:

Leu Xaa Leu Ser Xaa Xaa Pro Arg Thr Xaa Xaa Gln Xaa Gly Xaa Xaa Pro
                 5                  10                  15

Xaa Pro Thr Leu Trp Ala Glu Pro Xaa Ser Phe Ile Xaa Xaa Ser Asp Pro
        20                  25                  30

Lys Leu Xaa Leu Val Xaa Thr Gly
 35                  40

(2) INFORMATION FOR SEQ ID NO: 29:

(i) SEQUENCE CHARACTERISTICS:
            (A) LENGTH: 8 amino acids
            (B) TYPE: amino acid

```
        (D) TOPOLOGY: linear (ii) MOLECULE TYPE: peptide (xi) SEQUENCE DESCRIPTION: SEQ ID NO: 29:

Asp Tyr Lys Asp Asp Asp Asp Lys
                5
```

FAMILY OF IMMUNOREGULATORS DESIGNATED LEUKOCYTE IMMUNOGLOBULIN-LIKE RECEPTORS (LIR)

This application is a continuation of application Ser. No. 08/842,248, filed Apr. 24, 1997, now U.S. Pat. No. 6,448,035.

BACKGROUND OF THE INVENTION

Immune system cellular activity is controlled by a complex network of cell surface interactions and associated signaling processes. When a cell surface receptor is activated by its ligand a signal is sent to the cell, and, depending upon the signal transduction pathway that is engaged, the signal can be inhibitory or activatory. For many receptor systems cellular activity is regulated by a balance between activatory signals and inhibitory signals. In some of these it is known that positive signals associated with the engagement of a cell surface receptor by its ligand are downmodulated or inhibited by negative signals sent by the engagement of a different cell surface receptor by its ligand.

The biochemical mechanisms of these positive and negative signaling pathways have been studied for a number of known immune system receptor and ligand interactions. Many receptors that mediate positive signaling have cytoplasmic tails containing sites of tyrosine phosphatase phosphorylation known as immunoreceptor tyrosine-based activation motifs (ITAM). A common mechanistic pathway for positive signaling involves the activation of tyrosine kinases which phosphorylate sites on the cytoplasmic domains of the receptors and on other signaling molecules. Once the receptors are phosphorylated, binding sites for signal transduction molecules are created which initiate the signaling pathways and activate the cell. The inhibitory pathways involve receptors having immunoreceptor tyrosine based inhibitory motifs (ITIM) which, like the ITAMs, are phosphorylated by tyrosine kinases. Receptors having these motifs are involved in inhibitory signaling because these motifs provide binding sites for tyrosine phosphatases which block signaling by removing tyrosine from activated receptors or signal transduction molecules. While many of the details of the activation and inhibitory mechanisms are unknown, it is clear that functional balance in the immune system depends upon opposing activatory and inhibitory signals.

One example of immune system activity that is regulated by a balance of positive and negative signaling is B cell proliferation. The B cell antigen receptor is a B cell surface immunoglobulin which, when bound to antigen, mediates a positive signal leading to B cell proliferation. However, B cells also express Fcγ RIIb1, a low affinity IgG receptor. When an antigen is part of an immune complex with soluble immunoglobulin, the immune complex can bind B cells by engaging both the B cell antigen receptor via the antigen and FcγRIIb1 via the soluble immunoglobulin. Co-engagement of the Fcγ Rib1 with the B cell receptor complex downmodulates the activation signal and prevents B cell proliferation. FcγRIIb1 receptors contain ITIM motifs which are thought to deliver inhibitory signals to B cells via interaction of the ITIMs with tyrosine phosphatases upon co-engagement with B cell receptors.

The cytolytic activity of Natural Killer (NK) cells is another example of immune system activity which is regulated by a balance between positive signals that initiate cell function and inhibitory signals which prevent the activity. The receptors that activate NK cytotoxic activity are not fully understood. However, if the target cells express cell-surface MHC class I antigens for which the NK cell has a specific receptor, the target cell is protected from NK killing. These specific receptors, known as Killer Inhibitory Receptors (KIRs) send a negative signal when engaged by their MHC ligand, downregulating NK cell cytotoxic activity.

KIRs belong to the immunoglobulin superfamily or the C-type lectin family (see Lanier et al., *Immunology Today* 17:86–91,1996). Known human NK KIRs are members of the immunoglobulin superfamily and display differences and similarities in their extracellular, transmembrane and cytoplasmic regions. A cytoplasmic domain amino acid sequence common to many of the KIRs is an ITIM motif having the sequence YxxL/V. In some cases, it has been shown that phosphorylated ITIMs recruit tyrosine phosphatases which dephosphorylate molecules in the signal transduction pathway and prevent cell activation (see Burshtyn et al., *Immunity* 4:77–85, 1996). The KIRs commonly have two of these motifs spaced apart by 26 amino acids [YxxL/V(x)$_{26}$YxxL/V]. At least two NK cell receptors, each specific for a human leukocyte antigen (HLA) C allele (an MHC class I molecule), exist as an inhibitory and an activatory receptor. These receptors are highly homologous in the extracellular portions, but have major differences in their transmembrane and cytoplasmic portions. One of the differences is the appearance of the ITIM motif in the inhibitory receptor and the lack of the ITIM motif in the activating receptor (see Biassoni et al., *Journal. Exp. Med,* 183:645–650, 1996).

An immunoreceptor expressed by mouse mast cells, gp49B1, also a member of the immunoglobulin superfamily, is known to downregulate cell activation signals and contains a pair of ITIM motifs. gp49B1 shares a high degree of homology with human KIRs (Katz et al., *Cell Biology,* 93: 10809–10814, 1996). Mouse NK cells also express a family of immunoreceptors, the Ly49 family, which contain the ITIM motif and function in a manner similar to human KIRs. However, the Ly49 immunoreceptors have no structural homology with human KIRs and contain an extracellular C-type lectin domain, making them a member of the lectin superfamily of molecules (see Lanier et al., *Immunology Today* 17:86–91, 1996).

Clearly, the immune system activatory and inhibitory signals mediated by opposing kinases and phosphatases are very important for maintaining balance in the immune system. Systems with a predominance of activatory signals will lead to autoimmunity and inflammation. Immune systems with a predominance of inhibitory signals are less able to challenge infected cells or cancer cells. Isolating new activatory or inhibitory receptors is highly desirable for studying the biological signal(s) transduced via the receptor. Additionally, identifying such molecules provides a means of regulating and treating diseased states associated with autoimmunity, inflammation and infection.

For example engaging a newly discovered cell surface receptor having ITIM motifs with an agonistic antibody or ligand can be used to downregulate a cell function in disease states in which the immune system is overactive and excessive inflammation or immunopathology is present. On the other hand, using an antagonistic antibody specific to the receptor or a soluble form of the receptor can be used to block the interaction of the cell surface receptor with the receptor's ligand to activate the specific immune function in disease states associated with suppressed immune function. Conversely, since receptors lacking the ITIM motif send activatory signals once engaged as described above, the effect of antibodies and soluble receptors is the opposite of that just described.

SUMMARY OF THE INVENTION

The present invention provides a new family of immunoreceptor molecules of the immunoglobulin superfamily, designated herein as the Leukocyte Immunoglobulin-Like Receptor (LIR) polypeptides. Within the scope of the present invention are DNA sequences encoding LIR family members and their deduced amino acid sequences disclosed herein. Further included in the present invention are polypeptides encoded by DNA that hybridize to oligonucleotide probes having defined sequences or to DNA or RNA complementary to the probes. The present invention also includes recombinant expression vectors comprising DNA encoding LIR family members. Also within the scope of the present invention are nucleotide sequences which, due to the degeneracy of the genetic code, encode polypeptides substantially identical or substantially similar to polypeptides encoded by the nucleic acid sequences described above, and sequences complementary to those nucleotide sequences.

Further, the present invention includes processes for producing polypeptides of the LIR family by culturing host cells transformed with a recombinant expression vector that contains an LIR family member encoding DNA sequence under conditions appropriate for expressing an LIR polypeptide family member, then recovering the expressed LIR polypeptide from the culture. The invention also provides agonistic and antagonistic antibodies to LIR and LIR family members.

Further still within the present invention are fusion proteins which include a soluble portion of an LIR family member and the Fc portion of Ig.

Disorders mediated by autoimmune disease associated with failure of a negative signaling LIR to downregulate cell function may be treated by administering a therapeutically effective amount of an agonistic antibody or ligand of LIR family members to a patient afflicted with such a disorder. Disorders mediated by disease states associated with suppressed immune function can be treated by administering a soluble form of the negative signaling LIR. Conversely, disorders mediated by diseases associated with failure of a activatory signaling LIR can be treated by administering an agonistic antibody of the activatory receptor. Disorders mediated by states associated with autoimmune function can be treated by administering a soluble form of the activatory receptor.

DETAILED DESCRIPTION OF THE INVENTION

A viral glycoprotein having a sequence similarity to MHC class I antigens has been used to isolate and identify a new polypeptide, designated LIR-P3G2, and a new family of cell surface polypeptides designated the LIR polypeptide family. The LIR polypeptide family members possess extracellular regions having immunoglobulin-like domains, placing the members in a new subfamily of the immunoglobulin superfamily. While, the LIR family members are characterized as having very similar extracellular portions, the family includes three groups of polypeptides which are distinguishable by their transmembrane regions and their cytoplasmic regions. One group of the LIR polypeptides has a transmembrane region that includes a positively charged residue and a short cytoplasmic tail and a second group has a nonpolar transmembrane region and a long cytoplasmic tail. A third group includes a polypeptide expressed as a soluble protein having no transmembrane region or cytoplasmic tail. LIR-P3G2 is expressed by a variety of cells and recognizes HLA-B44 and HLA-A2 MHC molecules and, by analogy with known molecules, LIR-P3G2 has a role in immune recognition and self/nonself discrimination.

Examples 1–3 below describe isolating cDNA encoding P3G2 (LIR-P3G2) and a substantially identical polypeptide designated 18A3 (LIR-18A3). Briefly, the LIR-P3G2 family member was isolated by first expressing UL18, a Class I MHC-like molecule and using UL18 to isolate and identify P3G2 and 18A3. The nucleotide sequences of the isolated P3G2 cDNA and 18A3 cDNA are presented in SEQ ID NO:1 and SEQ ID NO:3, respectively. The amino acid sequences encoded by the cDNA presented in SEQ ID NO:1 and SEQ ID NO:3 are presented in SEQ ID NO:2 and SEQ ID NO:4, respectively. The P3G2 amino acid sequence (SEQ ID NO:2) has a predicted extracellular domain of 458 amino acids (1–458) including a signal peptide of 16 amino acids (amino acids 1–16); a transmembrane domain of 25 amino acids (amino acids 459–483) and, a cytoplasmic domain of 167 amino acids (amino acids 484–650). The extracellular domain includes four immunoglobulin-like domains. Ig-like domain I includes approximately amino acids 17–118; Ig-like domain II includes approximately amino acids 119–220; Ig-like domain III includes approximately amino acids 221–318; and Ig-like domain IV includes approximately amino acids 319–419. Significantly, the cytoplasmic domain of this polypeptide includes four ITIM motifs, each having the consensus sequence of YxxL/V. The first ITIM motif pair is found at amino acids 533–536 and 562–565 and the second pair is found at amino acids 614–617 and 644–647. This feature is identical to the ITIM motifs found in KIRs except that KIRs contain only one pair of ITIM motifs.

The 18A3 amino acid sequence has a predicted extracellular region of 459 amino acids (1–459) including a signal peptide of 16 amino acids (amino acids 1–16); a transmembrane domain of 25 amino acids (amino acids 460–484) and a cytoplasmic domain of 168 amino acids (485–652). The 18A3 amino acids sequence (SEQ ID NO:4) is substantially identical to that of P3G2 (SEQ ID NO:2) except that 18A3 has two additional amino acids (at amino acid 438 and 552) and 18A3 possesses an isoleucine residue at amino acid 142 in contrast to a threonine residue for P3G2. Additionally, 18A3 has a serine residue at amino acid 155 and P3G2 has an isoleucine at 155. Finally, the 18A3 polypeptide has a glutamic acid at amino acid 627 and P3G2 has a lysine at 625 which is aligned with the 627 residue of the 18A3 polypeptide. ITIM motifs in the 18A3 cytoplasmic domain are at amino acids 534–537 and 564–567 and at 616–619 and 646–649. Glycosylation sites occur at the amino acid triplet Asn-X-Y, where X is any amino acid except Pro and Y is Ser or Thr. Thus, potential glycosylation sites on LIR-P3G2 occur at amino acids 140–142; 281–283; 302–304; and 341–343. Sites on LIR-18A3 are at 281–283; 302–304; and 341–343. The features of these encoded polypeptides are consistent with type I transmembrane glycoproteins.

Example 8–10 describe isolating and identifying eight additional LIR polypeptide family members by probing cDNA libraries for plasmids that hybridize to a probe obtained from DNA encoding the extracellular region of LIR-P3G2. The nucleotide sequences (cDNA) of the isolated LIR family members are presented in SEQ ID NO:7 (designated pbm25), SEQ ID NO:9 (designated pbm8), SEQ ID NO:11 (designated pbm36-2), SEQ ID NO:13 (designated pbm36-4); SEQ ID NO:15 (designated pbmhh); SEQ ID NO:17 (designated pbm2), SEQ ID NO:19 (designated pbm17) and SEQ ID NO:21 (designated pbmnew). The amino acid sequences encoded thereby are presented in SEQ ID NO:8 (designated pbm25), SEQ ID NO:10 (designated pbm8), SEQ ID NO:12 (designated pbm36-2), SEQ ID NO:14 (designated pbm36-4), SEQ ID NO:16 (designated pbmhh); SEQ ID NO: 18 (designated pbm2); SEQ ID NO: 20 (designated pbm17), and SEQ ID NO:22 (designated pbmnew), respectively.

The identified extracellular, transmembrane and cytoplasmic regions for the LIR family members of SEQ ID NO:10, 12, 14, 16, 18, 20, and 22 are presented below. The polypeptide presented in SEQ ID NO:8 is a soluble protein having no transmembrane and cytoplasmic regions. As will be understood by the skilled artisan, the transmembrane region of P3G2 and 18A3 described above and those of LIR polypeptide family members presented below are identified in accordance with conventional criteria for identifying hydrophobic domains associated with such regions. Accordingly, the precise boundaries of any selected transmembrane region may vary from those presented above. Typically, the transmembrane domain does not vary by more than five amino acids on either end of the domain. Computer programs known in the art and useful for identifying such hydrophobic regions in proteins are available.

The polypeptide presented in SEQ ID NO:8 (LIR-pbm25) has a an extracellular domain that includes the entire amino acid sequence of amino acids 1–439 and a signal peptide of amino acids 1–16. The amino acid sequence presented in SEQ ID NO:10 (LIR-pbm8) has a predicted extracellular region of 458 amino acids (1–458) including a 16 amino acid signal peptide (amino acids 1–16); a transmembrane domain that includes amino acids 459–483; and a cytoplasmic domain that includes amino acids 484–598. The extracellular domain includes four immunoglobulin-like domains and the cytoplasmic domain includes an ITIM motif at amino acids 533–536 and 562–565.

The amino acid sequence presented in SEQ ID NO:12 (LIR-pbm36-2) has a predicted extracellular domain of amino acids including a 16 amino acid signal peptide of from amino acids 1–16; a transmembrane domain which includes amino acids 262–280 and a cytoplasmic domain of from amino acids 281–289. The transmembrane domain includes a charged arginine residue at 264 and the cytoplasmic domain is short, having only a length of only 9 amino acids.

The amino acid sequence presented in SEQ ID NO:14 (LIR-pbm36-4) has a predicted extracellular domain of amino acids 1–461 including a signal peptide from amino acids 1–16; a transmembrane domain that includes amino acids 462–480 and possesses a charged arginine residue at amino acid 464; and a cytoplasmic domain that includes amino acids 481–489. SEQ ID NO:14 is nearly identical to that of SEQ ID NO:12 except that it possesses four immunoglobulin domains in contrast to the two domains found in the extracellular region SEQ ID NO:12. The amino acid sequences presented in SEQ ID NO:12 and SEQ ID NO:14 are likely proteins encoded by alternatively spliced transcripts from the same gene.

The amino acid sequence presented in SEQ ID NO:16 (LIR-pbmhh) has a predicted extracellular domain that includes amino acids 1–449 and a signal peptide from amino acids 1–16; a transmembrane domain that includes amino acids 450–468 with a charged arginine residue at amino acid 452; and a cytoplasmic domain that includes amino acids 469–483. The cytoplasmic domain is short with a length of 15 amino acids. The extracellular domain includes four immunoglobulin-like domains.

The amino acid sequence presented in SEQ ID NO:18 (LIR-pbm2) has a predicted extracellular region that includes amino acids 1–259 and a signal peptide of amino acids 1–16; a transmembrane domain that includes amino acids 260–280; and a cytoplasmic domain that includes amino acids 281–448. This LIR family member has cytoplasmic domain which includes an ITIM motif at amino acids 412–415 and 442–445. The extracellular domain includes two immunoglobulin-like domains.

The amino acid sequence presented in SEQ ID NO:20 (LIR-pbm17) has a predicted extracellular domain of amino acids 1–443 that includes a signal peptide of amino acids 1–16; a transmembrane domain which includes amino acids 444–464; and a cytoplasmic domain of amino acids 465–631. The extracellular domain has four immunoglobulin-like domains. SEQ ID NO:20 has two pairs of ITIM YxxL/V motifs in the cytoplasmic domain. A first pair is at amino acids 514–517 and 543–546, and a second pair is at amino acids 595–598 and 625–628.

The amino acid sequence presented in SEQ ID NO: 22 (LIR-pbmnew) has a predicted extracellular domain of amino acids 1–456 including a signal peptide of amino acids 1–16; a transmembrane domain which includes amino acids 457–479; and a cytoplasmic domain of amino acids 480–590. The extracellular includes four immunoglobulin-like domains. SEQ ID NO: 22 has an ITIM motif at amino acids 554–557 and 584–587.

The sequences presented in SEQ ID NO: 2, 4, 8, 10, 12, 14, 16, 18, 20, and 22 reveal that the LIR family includes three groups of polypeptides. One group includes the polypeptides of SEQ ID NO:12, 14 and 16 which are distinguishable by a charged arginine residue in their transmembrane regions and their short cytoplasmic regions. A second group includes SEQ ID NO: 2, 4, 10, 18, 20 and 22 which are distinguishable by the hydrophobic cytoplasmic domains and the presence of the ITIM motif in their cytoplasmic regions. The third group includes the polypeptide of SEQ ID NO: 8 which is expressed as a soluble polypeptide and has no transmembrane region. This soluble polypeptide may function to block the interactions of cell surface family members with their receptors. Alternatively, this soluble polypeptide may act as an activatory signal when it binds to its receptor. The LIR polypeptides are characterized generally by the ability of their encoding DNA to hybridize to DNA encoding the P3G2 extracellular region.

The extracellular regions of the LIR family members presented in SEQ ID NO:2, 4, 8, 10, 12, 14, 16, 18, 20, and 22 have a high degree of homology which varies from 59%–84%. The extracellular regions of SEQ ID NO: 12 and SEQ ID NO:14 share sequence homology which is close to 100% since these polypeptides are from the same gene. Similarly, SEQ ID NO:2 and SEQ ID NO:4 share sequence homology that is in excess of 95% and it is thought that these may be alleles of the same gene. While sharing some structural similarities with other members of the immunoglobulin superfamily, the LIR family members have limited homology to these members of the immunoglobulin superfamily. Molecules having the closest structural similarity are the human KIRs and mouse gp49. However, LIR extracellular regions share only a 38–42% identity with the extracellular regions of NKAT3 and p58 Cl-39, respectively. The extracellular regions of the LIR family members are only 35–47% homologous with that of mouse gp49. In contrast, KIRs in general are known to share at least a 80% amino acid identity, with NKAT3 and p58 CL-39 being 81% homologous. Additionally, none of the known KIR molecules has four extracellular immunoglobulin domains which is characteristic of all but two of the known LIR family members. In view of the high sequence homology among the LIR related polypeptides disclosed herein and their relatively low homology with KIRs, the LIR polypeptides are members of a new family of immunoregulators.

An analysis of the amino acid sequences of the LIR polypeptides reveals that specific stretches of amino acids of the LIR polypeptides are highly conserved. One conserved region is the sequence of amino acids 5–50. A data base search determined that the LIR family members differ substantially from the most structurally similar prior art polypeptides in this LIR conserved region. The data base search and structural analysis was performed using BLAST NB1, a local alignment search tool for searching data bases and aligning amino acid sequences to determine identities and variations in a given sequence. The BLAST NB1 software is accessible on the internet at http://www3.ncb1.nlm.nih.gov/entrez/blast. The BLAST NB1 search for sequences having homology to the sequence of amino acids 5 to 50 of SEQ ID NO:2 found that the most structurally similar proteins are FcγIIR, gp49B form 2, and gp49B form 1 having identities with amino acids 5 to 50 of SEQ ID NO:2 of 63%, 67%, and 67% respectively. This contrasts with an LIR family identity with amino acids 5 to 50 of SEQ ID NO:2 which ranges from 77% to 100%. Specifically, LIR family members of the present invention have the following identities with amino acids 5–50 of SEQ ID NO:2: SEQ ID NO: 8 has a 96%; SEQ ID NO:10 has a 90% identity; SEQ ID NO:12 has a 96% identity; SEQ ID NO:14 has a 91% identity; SEQ ID NO:16 has a 97% identity; SEQ ID NO:18 has a 77% identity; SEQ ID NO:20 has an 80% identity; and, SEQ ID NO:22 has an 80% identity.

Sequence identity as used herein is the number of aligned amino acids which are identical, divided by the total number of amino acids in the shorter of the two sequences being compared. A number of computer programs are available commercially for aligning sequences and determining sequence identities and variations. These programs provide identity information based upon the above stated definition of identity. One suitable computer program is the GAP program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps. Another similar program, also available from the University of Wisconsin as part of the GCG computer package for sequence manipulation is the BESTFIT program.

In another aspect, the polypeptides of the present invention have conserved regions which are uniquely characterized as having the amino acid sequence (SEQ ID NO:28):
Leu $Xaa_a$ Leu Ser $Xaa_b$ $Xaa_c$ Pro Arg Thr $Xaa_d$ $Xaa_e$ Gln $Xaa_f$ Gly $Xaa_g$ $Xaa_h$ Pro $Xaa_i$ Pro Thr Leu Trp Ala Glu Pro $Xaa_j$ Ser Phe Ile $Xaa_j$ $Xaa_{70}$ Ser Asp Pro Lys Leu $Xaa_k$ Leu Val $Xaa_m$ Thr Gly
where $Xaa_a$ is Gly or Arg; $Xaa_b$ is Leu or Val; $Xaa_c$ is Gly or Asp; $Xaa_d$ is His Arg or Cys; $Xaa_e$ is Val or Met; $Xaa_f$ is Ala or Thr, $Xaa_g$ is His Pro or Thr; $Xaa_h$ Leu Ile or Phe; $Xaa_m$ is Gly Asp or Ala; $Xaa_j$ is Thr Ile Ser or Ala; $Xaa_k$ is Gly or Val; $Xaa_m$ is Met or Ala; and $Xaa_{70}$ is a sequence of 70 amino acids.

As mentioned above, certain LIR family have ITIM motifs ($YxxL/V_{25-26}YxxL/V$) in their cytoplasmic domains. It is known that many immune regulating receptors such as KIRs, CD22, FcγRIIb1 also have ITIMs in their cytoplasmic domain and function to send inhibitory signals which down regulate or inhibit cell function. It has been shown that these receptors associate with SHP-1 phosphatase via binding to the ITIM motifs. Recruitment of the SHP-1 phosphatase by the receptor appears to be required for intracellular signaling pathways that regulate the inhibitory function of the receptors. The experiment described in Example 11 demonstrates that LIR-P3G2 associates with SHP-1 phosphatase. It is known that many immune regulating receptors such as KIRs, CD22, FcγRIIb1 have ITIMs in their cytoplasmic domain and function to send inhibitory signals which down regulate or inhibit cell function. Thus, by analogy with KIRs, CD22 and FcγRIIb1, LIR family members presented in SEQ ID NO:2, 4, 10, 18, 20, and 22 that have IMTM motifs, deliver an inhibitory signal via the interaction of its ITIM with SHP-1 tyrosine phosphatase, or other tyrosine phosphatases, when the LIR is coligated with an appropriate receptor. Also by analogy with immunoregulatory receptors possessing ITIMs, LIR family members have a regulatory influence on humoral, inflammatory and allergic responses.

The LIR family members presented in SEQ ID NO:12, 14, and 16 have relatively short cytoplasmic domains, have transmembrane regions possessing at least one charged residue, and do not possess the ITIM motif. By analogy with membrane proteins that lack ITIM motifs and have charged transmembrane regions, these family members mediate stimulatory or activatory signals to cells. For example, membrane bound proteins containing a charged residue in the transmembrane regions are known to associate with other membrane-bound proteins that possess cytoplasmic tails having motifs known as immunoreceptor tyrosine-based activation motifs (ITAM). Upon association, the ITAMs become phosphorylated and propagate an activation signal.

The LIR polypeptide designated LIR-P3G2 is expressed on the surface of transfected or normal cells. This is evidenced by the results of the experiments described in Example 3 and Example 5 in which flow cytometry and precipitation techniques demonstrate that LIR-P3G2 is found on monocytes, a subpopulation of NK cells, and B cells. P3G2 was not detected on T cells. P3G2 is expressed as a 110–120 kDa glycoprotein. Since P3G2 has four potential glycosylation sites, the molecular size will vary with the degree of its glycosylation. Glycosylation sites occur at the amino acid triplet Asn-X-Y, where X is any amino acid except Pro and Y is Ser or Thr. Potential glycosylation sites on P3G2 occur at amino acids 139–141; 280–282; 302–304; and 340–342.

P3G2-LIR isolated as described in Example 3 was tested for its ability to bind to cell surface ligands distinct from UL18. As demonstrated by the experimental results detailed in Example 7, P3G2 binds HLA-B 44 and HLA-A2, class I MHC antigens. Since Class I MHC molecules play a central role in immune surveillance, self/non-self discrimination, the immune response to infection etc., the LIR-P3G2 polypeptide has a role in regulation of immune responses. It is known that NK cytolytic activity for killing tumor cells and cells infected with a virus is regulated by a delicate modulation of activatory and inhibitory signals. It has been shown that receptors specific for the same HLA class I molecules to which P3G2 binds may be activatory or inhibitory in their triggering mechanism. By analogy, P3G2 which binds MHC class I molecules, plays a role in balancing immune system cell activity and is useful in treating disease states in which the immune system balance is disrupted.

Within the scope of the present invention are polypeptides which include amino acid sequences encoded by DNA that hybridizes to LIR-P3G2 extracellular DNA probes under moderate to highly stringent conditions as taught herein. Probes which hybridize to DNA that encode polypeptides of the present invention include probes which encompass nucleotides 310–1684 of SEQ ID NO:1 or fragments thereof. Fragments of SEQ ID NO:1 utilized as hybridization probes are preferably greater than 17 nucleotides in length and may include nucleotides 358–1684; nucleotides 322–459 (encoding LIR conserved sequence); or DNA or RNA sequences complementary to SEQ ID NO:5, 6, 23, 24, 27 and 1 or fragments thereof. Fragments of SEQ ID NO:5, 6, 23, 24 and 27 include these sequences without the restrictions sites. Conditions for hybridization may be moderately stringent conditions described in, for example, Sambrook et al, *Molecular Cloning: A Laboratory Manual*, 2nd ed., Vol. 1, pp 1.101–104, Cold Spring Harbor Laboratory Press, 1989. Conditions of moderate stringency, as defined by Sambrook et al., include use of a prewashing solution of 5×SSC, 0.5% SDS, 1.0 mM EDTA (pH 8.0) and hybridization conditions of about 55° C., 5×SSC, overnight. Highly stringent conditions include higher temperatures of hybridization and washing. The skilled artisan will recognize that the temperature and wash solution salt concentration may be adjusted as necessary according to factors such as the length of the probe. Preferred embodiments include amino acid sequences encoded by DNA that hybridizes to probes of the extracellular region of LIR-P3G2 having at least 17 nucleotides. Preferred hybridizing conditions include a temperature of 63° C. for 16 hours in a hybridizing solution of Denhart's Solution, 0.05 M TRIS at pH 7.5, 0.9 M NaCl, 0.1% sodium pyrophosphate, 1% SDS and 200 µg/mL salmon sperm DNA, followed by washing with 2×SSC at 63° C. for one hour and the a wash with 1×SSC at 63° C. for one hour.

The present invention includes polypeptides having amino acid sequences that differ from, but are highly homologous to, those presented in SEQ ID NO:2, 4, 8, 10, 12, 14, 16, 18, 20 and 22. Examples include, but are not limited to, homologs derived from other mammalian species, variants (both naturally occurring variants and those generated by recombinant DNA technology), and LIR P3G2 and LIR family member fragments that retain a desired biological activity. Preferably, such polypeptides exhibit a biological activity associated with the LIR polypeptides described in SEQ ID Nos:2, 4, 8, 10, 12, 14, 16, 18 20 and 22 and comprise an amino acid sequence that is at least 80% identical to any of the amino acid sequences of the signal peptide and extracellular domains of the polypeptides presented in SEQ ID NOS:2, 4, 8, 10, 12, 14, 16, 18, 20 and 22. Preferably such polypeptides are at least 90% identical to any of the amino acid sequences of the signal peptide and extracellular domains of the polypeptides presented in SEQ ID NOS: 2, 4, 8, 10, 12, 14, 16, 18, 20 and 22. Determining the degree of identity between polypeptides can be achieved using any algorithms or computer programs designed for analyzing protein sequences. The commercially available GAP program described below is one such program. Other programs include the BESTFIT and GCG programs which are also commercially available.

Within the scope of the present invention are LIR polypeptide fragments that retain a desired biological property of an LIR polypeptide family member such as binding to MHC class I or other ligand. In one such embodiment, LIR polypeptide fragments are soluble LIR polypeptides comprising all or part of the extracellular domain, but lacking the transmembrane region that would cause retention of the polypeptide on a cell membrane. Soluble LIR polypeptides are capable of being secreted from the cells in which they are expressed. Advantageously, a heterologous signal peptide is fused to the N-terminus such that the soluble LIR is secreted upon expression. Soluble LIR polypeptides include extracellular domains incorporating the signal peptide and those in which the signal peptide is cleaved signal peptide.

The use of soluble forms of a LIR family member is advantageous for certain applications. One such advantage is the ease of purifying soluble forms from recombinant host cells. Since the soluble proteins are secreted from the cells, the protein need not be extracted from cells during the recovery process. Additionally, soluble proteins are generally more suitable for intravenous administration and can be used to block the interaction of cell surface LIR family members with their ligands in order to mediate a desirable immune function.

Soluble LIR polypeptides include the entire extracellular domain or any desirable fragment thereof, including extracellular domains that exclude signal peptides. Thus, for example, soluble LIR polypeptides include amino acids $x_1$-458 of SEQ ID NO:2, where $x_1$ is amino acids 1 or 17; amino acids $x_2$-459 of SEQ ID NO:4, where $x_2$ is amino acid 1 or 17; amino acids $x_3$-439 of SEQ ID NO:8, where $x_3$ is amino acid 1 or 17; amino acids $x_4$-458 of SEQ ID NO:10, where $x_4$ is amino acid 1 or 17; amino acids $x_5$-241 of SEQ ID NO:12, where amino acid $x_5$ is amino acid 1 or 17, amino acids $x_6$-461 of SEQ ID NO:14, where $x_6$ is amino acid 1 or 17; amino acids $x_7$-449 of SEQ ID NO: 16, where $x_7$ is amino acid 1 or 17; amino acids $x_8$-259 of SEQ ID NO:18, where $x_8$ is amino acid 1 or 17; amino acids $x_9$-443 of SEQ ID NO:20, where $x_9$ is amino acid 1 or 17; and amino acids $x_{10}$-456 of SEQ ID NO:22, where $x_{10}$ is amino acid 1 or 17. The above identified soluble LIR polypeptides include LIR extracellular regions that include and exclude signal peptides. Additional soluble LIR polypeptides include fragments of the extracellular domains of family members that retain a desired biological activity, such as binding to ligands that include MHC class I molecules.

LIR family member fragments, including soluble polypeptides, may be prepared by any of a number of conventional techniques. A DNA sequence encoding a desired LIR polypeptide encoding fragment may be subcloned into an expression vector for production of the LIR polypeptide fragment. The selected encoding DNA sequence advantageously is fused to a sequence encoding a suitable leader or signal peptide. The desired LIR member encoding DNA fragment may be chemically synthesized using known DNA synthesis techniques. DNA fragments also may be produced by restriction endonuclease digestion of a full length cloned DNA sequence, and isolated by electrophoresis on an appropriate gel. If necessary, oligonucleotides that reconstruct the 5' or 3' terminus to a desired point may be ligated to a DNA fragment generated by restriction enzyme digestion. Such oligonucleotides may additionally contain a restriction endonuclease cleavage site upstream of the desired coding sequence, and position an initiation codon (ATG) at the N-terminus of the coding sequence.

Another technique useful for obtaining a DNA sequence encoding a desired protein fragment is the well known polymerase chain reaction (PCR) procedure. Oligonucleotides which define the termini of the desired DNA are used as probes to synthesize additional DNA from a desired DNA template. The oligonucleotides may also contain recognition sites for restriction endonucleases, to facilitate inserting the amplified DNA fragment into an expression vector. PCR techniques are described in Saiki et al., *Science* 239:487 (1988): *Recombinant DNA Methodology*, Wu et al., eds., Academic Press, Inc., San Diego (1989), pp. 189–196; and *PCR Protocols: A Guide to Methods and Applications*, Innis et al., eds., Academic Press, Inc. (1990).

DNA of LIR family members of the present invention include cDNA, chemically synthesized DNA, DNA isolated by PCR, genomic DNA, and combinations thereof. Genomic LIR family DNA may be isolated by hybridization to the LIR family cDNA disclosed herein using standard techniques. RNA transcribed from LIR family DNA is also encompassed by the present invention.

Within the scope of the present invention are DNA fragments such as LIR polypeptide coding regions and DNA fragments that encode soluble polypeptides. Examples of DNA fragments that encode soluble polypeptides include DNA that encodes entire extracellular regions of LIR family members and DNA that encodes extracellular region fragments such as regions lacking the signal peptide. More specifically, the present invention includes nucleotides 310–2262 of SEQ ID NO:1 (P3G2 coding region); nucleotides $x_1$-1683 of SEQ ID NO:1, where $x_1$ is 310 or 358 (encoding the P3G2 extracellular domain); nucleotides 168–2126 of SEQ ID NO:3 (the 18A3 coding region) and nucleotides $x_2$-1544 of SEQ ID NO:3, where $x_2$ is 168 or 216 (the 18A3 extracellular domain coding region); nucleotides $x_3$-1412 of SEQ ID NO:7, where $x_3$ is 93 or 141 (the pbm25 coding region and extracellular region); nucleotides 184–1980 of SEQ ID NO:9, (the pbm8 coding region) and nucleotides $x_4$-1557 of SEQ ID NO:9, where $x_3$ is 184 or 232 (the pmb8 extracellular domain coding region); nucleotides 171–1040 of SEQ ID NO:11 (pbm36-2 coding region) and nucleotides $x_5$-878 of SEQ ID NO:11, where $x_5$ is 171 or 219 (encoding the pbm36-2 extracellular domain); nucleotides 183–1652 of SEQ ID NO:13 (coding region for pbm36-4) and nucleotides $x_6$-1565 of SEQ ID NO:13, where $x_6$ is 183 or 231 (encoding the pbm36-4 extracellular domain); nucleotides 40–1491 of SEQ ID NO:15 (the pbmhh coding region) and nucleotides $x_7$-1386 of SEQ ID NO:15, where $x_7$ is 40 or 88 (encoding the pbmhh extracellular domain); nucleotides 30–1376 of SEQ ID NO:17 (the pbm2 coding region) and nucleotides $x_8$-806 of SEQ ID NO:17, where $x_8$ is 30 or 78 (encoding the pbm2 extracellular region); nucleotides 66–1961 of SEQ ID NO:19 (the pbm17 coding region) and nucleotides $x_9$-1394 of SEQ ID NO:19, where $x_9$ is 66 or 114 (encoding the pbm17 extracellular domain); and nucleotides 67–1839 of SEQ ID NO:21 (the pbmnew coding region) and nucleotides $x_{10}$-1434 of SEQ ID NO:21, where $x_{10}$ is 67 or 115 (encoding the pbmnew extracellular domain).

Included in the present invention are DNAs encoding biologically active fragments of the LIR family members presented in SEQ ID NOS:2, 4, 8, 10, 12, 14, 16, 18, 20, and 22.

The present invention encompasses nucleotide sequences which, due to the degeneracy of the genetic code, encode polypeptides substantially identical or substantially similar to polypeptides encoded by the nucleic acid sequences described above, and sequences complementary to them. Accordingly, within the present invention are DNA encoding biologically active LIR family members which include the coding region of a native human LIR family member cDNA, or fragments thereof, and DNA which is degenerate as a result of the genetic code to the native LIR polypeptide DNA sequence or the DNA of native LIR family members described herein.

In another aspect, the present invention includes LIR variants and derivatives as well as variants and derivatives of LIR family polypeptides, both recombinanat and non-recombinant, that retain a desired biological activity. An LIR variant, as referred to herein, is a polypeptide substantially homologous to a native LIR polypeptide, as described herein, except the variant amino acid sequence differs from that of the native polypeptide because of one or more deletions, insertions or substitutions.

LIR family variants may be obtained from mutations of native LIR nucleotide sequences. Within the present invention are such DNA mutations or variants which include nucleotide sequences having one or more nucleotide additions, nucleotide deletions, or nucleotide substitutions compared to native DNA of LIR family members and which encode variant LIR polypeptides or variant LIR family members having a desired biological activity. Preferably the biological activity is substantially the same as that of the native LIR polypeptide.

Variant amino acid sequences and variant nucleotide sequences of the present invention preferably are at least 80% identical to that of a native LIR family member sequence. One method for determining the degree of homology or identity between a native amino acid or nucleotide sequence and a variant amino acid or nucleotide sequence is to compare the sequences using computer programs available for such purposes. One suitable computer program is the GAP program, version 6.0, described by Devereux et al. (*Nucl. Acids Res.* 12:387, 1984) and available from the University of Wisconsin Genetics Computer Group (UWGCG). The GAP program utilizes the alignment method of Needleman and Wunsch (*J. Mol. Biol.* 48:443, 1970), as revised by Smith and Waterman (*Adv. Appl. Math* 2:482, 1981). Briefly, the GAP program defines identity as the number of aligned symbols (i.e., nucleotides or amino acids) which are identical, divided by the total number of symbols in the shorter of the two sequences being compared. The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional 0.10 penalty for each symbol in each gap; and (3) no penalty for end gaps.

Alterations of native LIR amino acid sequences may be provided by using any of a number of known techniques. As described above, mutations can be introduced at selected sequence sites by synthesizing oligonucleotides containing a mutant coding sequence, flanked by restriction sites enabling its ligation to fragments of the native sequence. After ligating the synthesized oligonucleotides to the native sequence fragments, the resulting reconstructed nucleotide sequence will encode an analog or variant polypeptide having the desired amino acid insertion, substitution, or deletion. Another procedure suitable for preparing variant polypeptides is oligonucleotide-directed site-specific mutagenesis procedures which provide genes having specific codons altered in accordance with the desired substitution, deletion, or insertion. Techniques for making such alterations include those disclosed in the following references: Walder et al. *Gene,* 42:133, 1986; Bauer et al., *Gene* 37:73, 1985; Craik, *BioTechniques,* 12–19 January, 1985; Smith et al. *Genetic Engineering: Principles and Methods*, Plenum Press, 1981; and U.S. Pat. Nos. 4,518,584 and 4,737,462, all of which are incorporated herein by reference.

Variant polypeptides of the present invention may have amino acid sequences which are conservatively substituted, meaning that one or more amino acid residues of a native LIR polypeptide family member is replaced by different residues, such that the variant polypeptide retains a desired biological activity that is essentially equivalent to that of a native LIR family member. In general, a number of approaches to conservative substitutions are well known in the art and can be applied in preparing variant of the present invention. For example, amino acids of the native polypeptide sequence may be substituted for amino acids which do not alter the secondary and/or tertiary structure of the LIR polypeptide. Other suitable substitutions include those which involve amino acids outside of the ligand-binding domain of interest. One approach to conservative amino acid substitutions involves replacing one or amino acids with those having similar physiochemical characteristics, e.g. substituting one aliphatic residue for another such as Ile, Val, Leu, or Ala for one another); substituting one polar residue for another (such as between Lys and Arg; Glu and Asp; or Gln and Asn); or substituting entire regions having similar hydrophobicity or hydrophilic characteristics.

LIR polypeptide variants can be tested for binding to cells as described in Examples 5 and 6 and for phosphatase binding activity as described in Example 11 to confirm biological activity. Other LIR variants within the present invention include polypeptides which are altered by changing the nucleotide sequence encoding the polypeptide so that selected polypeptide Cys residues are deleted or replaced with one or more alternative amino acids. These LIR variants will not form intramolecular disulfide bridges upon renaturation. Naturally occurring LIR polypeptides selected for alteration by deleting or altering Cys residues preferably do not have biological activities which depend upon disulfide bridges formed by the Cys residue. Other possible variants are prepared by techniques which cause the modification of adjacent dibasic amino acid residues to enhance expression in yeast systems in which KEX2 protease activity is present. EP 212,914 discloses site-specific mutagenesis techniques for inactivating KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys and pairings are considerably less susceptible to KEX2 cleavage, and conversion of Arg-Lys or Lys-Arg to Lys-Lys represents a conservative and preferred approach to inactivating KEX2 sites.

Naturally occurring LIR variants are also encompassed by the present invention. Examples of such variants are proteins that result from alternative mRNA splicing events or from proteolytic cleavage of an LIR polypeptide. Alternative splicing of mRNA may yield a truncated but biologically active LIR polypeptide such as a naturally occurring soluble form of the protein. Variations attributable to proteolysis include difference in the N- or C-termini upon expression in different types of host cells, due to proteolytic removal of one or more terminal amino acids from the LIR polypeptide. In addition, proteolytic cleavage may release a soluble form of LIR from a membrane-bound form of the polypeptide. Other naturally occurring LIR variations are those in which differences from the amino acid sequence of SEQ ID Nos:2, 4, 8, 10, 12, 14, 16, 18, 20 and 22 are attributable to genetic polymorphism, the allelic variation among individuals.

Within the scope of the present invention are derivative LIR family polypeptides which include native or variant LIR polypeptides modified to form conjugates with selected chemical moieties. The conjugates can be formed by covalently linking another moiety to a native or variant LIR or by non-covalently linking another moiety to a native or variant LIR. Suitable chemical moieties include but are not limited to glycosyl groups, lipids, phosphates, acetyl groups, and other proteins or fragments thereof. Techniques for covalently linking chemical moieties to proteins are well known in the art and are generally suitable for preparing derivative LIR polypeptides. For example, active or activated functional groups on amino acid side chains can be used as reaction sites for covalently linking a chemical moiety to a LIR polypeptide. Similarly, the N-terminus or C-terminus can provide a reaction site for a chemical moiety. LIR polypeptides or fragments conjugated with other proteins or protein fragments can be prepared in recombinant culture as N-terminal or C-terminal fusion products. For example, the conjugate or fusion portions may include a signal or leader sequence attached to an LIR molecule at its N-terminus. The signal or leader peptide co-translationally or post-translationally directs transfer of the conjugate from its site of synthesis to a site inside or outside of the cell membrane.

One useful LIR polypeptide conjugate is one incorporating a poly-His or the antigenic identification peptides described in U.S. Pat. No. 5,011,912 and in Hopp et al., *Bio/Technology* 6:1124, 1988. For example, the FLAG-® peptide, Asp-Tyr-Lys-Asp-Asp-Asp-Asp-Lys (DYKDDDDK) is highly antigenic and provides an epitope reversibly bound by a specific monoclonal antibody, thus enabling rapid assay and facile purification of expressed recombinant protein. This sequence is specifically cleaved by bovine mucosal enterokinase at the residue immediately following the Asp-Lys pairing. Fusion proteins capped with this peptide may be resistant to intracellular degradation in *E. coli*. Murine hybridoma designated 4E11 produced a monoclonal antibody that binds the peptide DYKDDDDK in the presence of certain divalent metal cations, and has been deposited with the American Type Culture Collection under accession no HB 9259. Expression systems useful for producing recombinant proteins fused to the FLAG® peptide, and monoclonal antibodies that bind the peptide and are useful in purifying the recombinant proteins, are available from Eastman Kodak Company, Scientific Imaging Systems, New Haven, Conn.

Particularly suitable LIR fusion proteins are those in which an LIR polypeptide is in the form of an oligomer. Oligomers may be formed by disulfide bonds between cysteine residues on more than one LIR polypeptide, or by noncovalent interactions between LIR polypeptide chains. In another approach, LIR oligomers can be formed by joining LIR polypeptides or fragment thereof via covalent or noncovalent interactions between peptide moieties fused to the LIR polypeptide. Suitable peptide moieties include peptide linkers or spacers, or peptides that have the property of promoting oligomerization. Leucine zippers and certain polypeptides derived from antibodies are among the peptides that can promote oligomerization of LIR polypeptides attached thereto.

Other LIR fusion proteins which promote oligomer formation are fusion proteins having heterologous polypeptides fused to various portions of antibody-derived polypeptides (including the Fc domain). Procedures for preparing such fusion proteins are described in Ashkenazi et al. *PNAS USA* 88:10535, 1991; Byrne et al. *Nature* 344:667, 1990, and Hollenbaugh and Aruffo *Current Protocols in Immunology*, Supplement 4, pages 10.19.1–10.19.11, 1992; all of which are incorporated herein by reference. Example 1 and Example 5 below describe methods for preparing UL18:Fc and P3G2:Fc fusion proteins, respectively, by fusing P3G2 and UL18 to an Fc region polypeptide derived from an antibody. This is accomplished by inserting into an expression vector a gene fusion encoding the P3G2:Fc fusion protein and expressing the P3G2:Fc fusion protein. The fusion proteins are allowed to assemble much like antibody molecules, whereupon interchain disulfide bonds form between the Fc polypeptides, yielding divalent P3G2 polypeptide. In a similar approach, P3G2 or any LIR polypeptide may be substituted for the variable portion of an antibody heavy or light chain. If fusion proteins are made with heavy and light chains of an antibody, it is possible to form a LIR oligomer with as many as four LIR regions.

As used herein, a Fc polypeptide includes native and mutein forms, as well as truncated Fc polypeptides containing the hinge region that promotes dimerization. One suitable Fc polypeptide is the native Fc region polypeptide derived from a human IgG 1, which is described in PCT application WO 93/10151, hereby incorporated herein by reference. Another useful Fc polypeptide is the Fc mutein described in U.S. Pat. No. 5,457,035. The amino acid sequence of the mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. This mutein Fc exhibits reduced affinity for immunoglobulin receptors.

Alternatively, oligomeric LIR polypeptide variants may include two or more LIR peptides joined through peptide linkers. Examples include those peptide linkers described in U.S. Pat. No. 5,073,627, incorporated herein by reference. Fusion proteins which include multiple LIR polypeptides separated by peptide linkers may be produced conventional recombinant DNA technology.

Another method for preparing oligomeric LIR polypeptide variants involves use of a leucine zipper. Leucine zipper domains are peptides that promote oligomerization of the proteins in which they are found. Leucine zippers were first identified in several DNA-binding proteins (Landschulz et al. *Science* 240:1759, 1988). Among the known leucine zippers are naturally occurring peptides and peptide derivatives that dimerize or trimerize. Examples of leucine zipper domains suitable for producing soluble oligomeric LIR polypeptides or oligomeric polypeptides of the LIR family are those described in PCT application WO 94/10308, incorporated herein by reference. Recombinant fusion proteins having a soluble LIR polypeptide fused to a peptide that dimerizes or trimerizes in solution may be expressed in suitable host cells, and the resulting soluble oligomeric LIR polypeptide recovered from the culture supernatant.

Numerous reagents useful for cross-linking one protein molecule to another are known. Heterobifunctional and homobifunctional linkers are available for this purpose from Pierce Chemical Company, Rockford, Ill., for example. Such linkers contain two functional groups (e.g., esters and/or maleimides) that will react with certain functional groups on amino acid side chains, thus linking one polypeptide to another.

One type of peptide linker that may be employed in the present invention separates polypeptide domains by a distance sufficient to ensure that each domain properly folds into the secondary and tertiary structures necessary for the desired biological activity. The linker also should allow the extracellular portion to assume the proper spatial orientation to form the binding sites for ligands.

Suitable peptide linkers are known in the art, and may be employed according to conventional techniques. Among the suitable peptide linkers-are those described in U.S. Pat. Nos. 4,751,180 and 4,935,233, which are hereby incorporated by reference. A peptide linker may be attached to LIR polypeptides by any of the conventional procedures used to attach one polypeptide to another. The cross-linking reagents available from Pierce Chemical Company as described above are among those that may be employed. Amino acids having side chains reactive with such reagents may be included in the peptide linker, e.g., at the termini thereof. Preferably, a fusion proteins formed via a peptide linker are prepared by recombinant DNA technology.

The fusion proteins of the present invention include constructs in which the C-terminal portion of one protein is fused to the linker which is fused to the N-terminal portion of another protein. Peptides linked in such a manner produce a single protein which retains the desired biological activities. The components of the fusion protein are listed in their order of occurrence (i.e., the N-terminal polypeptide is listed first, followed by the linker and then the C-terminal polypeptide).

A DNA sequence encoding a fusion protein is constructed using recombinant DNA techniques to insert separate DNA fragments encoding the desired proteins into an appropriate expression vector. The 3' end of a DNA fragment encoding one protein is ligated (via the linker) to the 5' end of the DNA fragment encoding another protein with the reading frames of the sequences in phase to permit translation of the mRNA into a single biologically active fusion protein. A DNA sequence encoding an N-terminal signal sequence may be retained on the DNA sequence encoding the N-terminal polypeptide, while stop codons, which would prevent read-through to the second (C-terminal) DNA sequence, are eliminated. Conversely, a stop codon required to end translation is retained on the second DNA sequence. DNA encoding a signal sequence is preferably removed from the DNA sequence encoding the C-terminal polypeptide.

A DNA sequence encoding a desired polypeptide linker may be inserted between, and in the same reading frame as, the DNA sequences encoding the two proteins using any suitable conventional technique. For example, a chemically synthesized oligonucleotide encoding the linker and containing appropriate restriction endonuclease cleavage sites may be ligated between the sequences encoding Fc and a P3G2 polypeptide.

Within the scope of the present invention are recombinant expression vectors for expressing polypeptides of the LIR family, and host cells transformed with the expression vectors. Expression vectors of the invention include DNA encoding LIR family members operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the LIR DNA sequence. Thus, a promoter nucleotide sequence is operably linked to a LIR DNA sequence if the promoter nucleotide sequence controls the transcription of the LIR DNA sequence. An origin of replication that confers the ability to replicate in the desired host cells, and a selection gene by which transformants are identified, are generally incorporated in the expression vector.

In addition, a sequence encoding an appropriate signal peptide can be incorporated into expression vectors. A DNA sequence for a signal peptide (secretory leader) may be fused in frame to the LIR sequence so that the LIR is initially translated as a fusion protein comprising the signal peptide. A signal peptide that is functional in the intended host cells promotes extracellular secretion of the LIR polypeptide. The signal peptide is cleaved from the LIR polypeptide upon secretion of the LIR polypeptide from the cell.

Suitable host cells for expression of LIR polypeptides include prokaryotes, yeast or higher eukaryotic cells. Appropriate cloning and expression vectors for use with bacterial, fungal, yeast, and mammalian cellular hosts are described, for example, in Pouwels et al. *Coning Vectors: A Laboratory Manual*, Elsevier, N.Y., (1985). Cell-free translation systems could also be employed to produce P3G2 polypeptides using RNAs derived from DNA constructs disclosed herein.

Prokaryote host cells suitable in the practice of the present invention include gram negative or gram positive organisms, for example, *E. coli* or *Bacilli*. Suitable prokaryotic host cells for transformation include, for example, *E. coli, Bacillus subtilis, Salmonella typhimurium*, and various other species within the general *Pseudomonas, Streptomyces,* and *Staphylococcus*. In a prokaryotic host cell, such as *E. coli*, a P3G2 polypeptide may include an N-terminal methionine residue to facilitate expression of the recombinanat polypeptide. The N-terminal Met may be cleaved from the expressed recombinant LIR polypeptide.

Expression vectors for use in prokaryotic host cells generally include one or more phenotypic selectable marker genes. A phenotypic selectable marker gene is, for example, a gene encoding a protein that confers antibiotic resistance or that supplies an autotrophic requirement. Examples of useful expression vectors for prokarytoic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a LIR family DNA may be inserted into the pBR322 vector. Other commercially available vectors include, for example, pKK223–3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al. *Nature* 75:615, 1978; and Goeddel et al., *Nature* 281:544, 1979), tryptophan (trp) promoter system (Goeddel et al., *Nucl. Acids Res.* 8:4057, 1980); and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phase $\lambda P_L$ promoter and a cI857ts thermolabile repressor sequence. Plasmid vectors available from the American Type Culture Collection which incorporate derivatives of the $\lambda P_L$ promoter include plastid pHUB2 (resident in *E. coli* strain JMB9, ATCC 37092) and pPLc28 (resident in *E. coli* RR1, ATCC 53082).

Alternatively, LIR polypeptides may be expressed in yeast host cells, preferably from the *Saccharomyces* genus (e.g., *S. cerevisiae*). Other genera of yeast, such as *Pichia* or *Kluyveromyces* may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem* 255:2073, 1980) or other glycolytic enzymes (Hess et al., *J. Adv. Enzyme Reg.* 7:149, 1968); and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,675. Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA from pBR322 for selection and replication in *E. coli* (Amp$^r$ gene and origin of replication) into the above-described yeast vectors.

The yeast α-factor leader sequence may be employed to direct secretion of the LIR polypeptide. The α-factor leader sequence is often inserted between the promoter sequence and the structural gene sequence. See, e.g., Kurjan et al., *Cell* 30:933,1982 and Bitter et al., *Proc. Natl. Acad. Sci. USA* 81:5330, 1984. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 μg/mL adenine and 20 μg/mL uracil.

Yeast host cells transformed by vectors containing an ⁻ADH2 promoter sequence may be grown for inducing expression in a "rich" medium. An example of a rich medium is one having 1% yeast extract, 2% peptone, and 1% glucose supplemented with 80 μg/mL uracil. Derepression of the ADH2 promoter occurs when glucose is exhausted from the medium.

Mammalian or insect host cell culture systems may be used to express recombinant LIR polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651)(Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CVI/EBNA cell cline derived from the African green monkey cell line CVI (ATCC CCL 70) as described by McMahan et al. (*EMBO J.* 10:2821, 1991). COS-1 (ATCC CRL-1650).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the HIND III site toward the Bg/I site located in the SV40 viral origin of replication site is included.

Suitable expression vectors for use in mammalian host cells can be constructed as disclosed by Okayama and Berg (*Mol. Cell. Biol.* 3:280, 1983). One useful system for stable high level expression of mammalian receptor cDNAs in C127 murine mammary epithelial cells can be constructed substantially as described by Cosman et al. (*Mol. Immunol.* 23:935, 1986). A high expression vector, PMLSV N1/N4, described by Cosman et al., *Nature* 312:768, 1984 has been deposited as ATCC 39890. Additional mammalian expression vectors are described in EP-A-0367566, and in WO 91/18982. Still additional expression vectors for use in mammalian host cells include pDC201 (Sims et al., *Science* 241:585, 1988), pDC302 (Mosley et al. *Cell* 59:335, 1989), and pDC406 (McMahan et al., *EMBO J.* 10:2821, 1991). Vectors derived from retroviruses also may be employed. One preferred expression system employs pDC409 as discussed in Example 5 below.

For expression of LIR polypeptides the expression vector may comprise DNA encoding a signal or leader peptide. In place of the native signal sequence, a heterologous signal sequence may be added, such as the signal sequence for interleukin-7 (IL-7) described in U.S. Pat. No. 4,965,195; the signal sequence for interleukin-2 receptor described in Cosman et al., *Nature* 312:768, 1984); the interleukin-4 signal peptide described in EP 367,566; the type I interleukin-1 receptor signal peptide described in U.S. Pat. No. 4,968,607; and the type II interleukin-1 receptor signal peptide described in EP 460,846.

Further contemplated within the present invention are purified LIR family polypeptides. The purified polypeptides of the present invention may be purified from recombinant expression systems as described above or purified from naturally occurring cells. The desired degree of purity may depend on the intended use of the protein with a relatively high degree of purity preferred when the protein is intended for in vivo use. Preferably, LIR polypeptide purification processes are such that no protein bands corresponding to proteins other than the desired LIR protein are detectable by SDS-polyacrylamide gel electrophoresis (SDS-PAGE). It will be recognized by one skilled in the art that multiple bands corresponding to any LIR polypeptide my be detected by SDS-PAGE, due to differential glycosylation, variations in post-translational processing, and the like, as discussed above. Most preferably, any specific LIR polypeptide is purified to substantial homogeneity, as indicated by a single protein band upon analysis by SDS-PAGE. The protein band may be visualized by silver staining, Coomassie blue staining, or by autoradiography or fluorescence if the protein is appropriately labeled.

One process for providing purified LIR polypeptides includes first culturing a host cell transformed with an expression vector comprising a DNA sequence that encodes the desired polypeptide under conditions that promote expressing the desired LIR polypeptide and then recovering the LIR polypeptide. As the skilled artisan will recognize, procedures for recovering the polypeptide will vary according to such factors as the type of host cells employed and whether the polypeptide is secreted in the culture medium is extracted from cells.

When the expression system secretes the polypeptide into the culture medium, the medium may be first concentrated using a commercially available protein concentration filter, for example, an Amicon or Millipore Pellicon ultrafiltration unit. Following the concentration step, the concentrate can be applied to a suitable purification matrix such as a gel filtration medium. Alternatively, an anion exchange resin can be employed, such as a resin matrix or resin substrate having pendant diethylaminoethyl (DEAE) groups. The matrices can be acrylamide, agarose, dextran, cellulose or other types commonly employed in protein purification. Similarly, a purification matrix having cation exchange groups such as sulfopropyl or carboxymethyl functionalities on an insoluble matrix can be used. Sulfopropyl groups are preferred. Still other purification matrices and methods suitable for providing purified LIR are high performance liquid chromatography using hydrophobic reversed phase media (RP-HPLC). One skilled in the art will recognized the any or all of the foregoing purification steps, in various combinations, can be employed to provide a purified LIR polypeptide.

Alternatively, LIR polypeptides can be purified by immunoaffinity chromatography. An affinity column containing an antibody that binds a LIR polypeptide may be prepared by conventional procedures and employed in purifying LIR. Example 5 describes a procedures for generating monoclonal antibodies directed against P3G2 which may be utilized in immunoaffinity chromatography.

Recombinant protein produced in bacterial culture may be isolated by first disrupting the host cells by any convenient method, including freeze-thaw cycling, sonication, mechanical disruption, or use of cell lysing agents and then extracting the polypeptide from cell pellets if the polypeptide is insoluble, or from the supernatant fluid if the polypeptide is soluble. After the initial isolation step, the purification process may include one or more concentrating, salting out, ion exchange, affinity, or size exclusion chromatography purification steps. For many application a final RP-HPLC purification step is beneficial.

Additional methods for providing LIR polypeptides and purified LIR polypeptides involves fermenting yeast which express proteins as a secreted protein. Secreted recombinant protein resulting from a large-scale fermentation can be purified by methods analogous to those disclosed by Urdal et al. (*J. Chromatog.* 296:171, 1984), involving two sequential, reversed-phase HPLC steps for purification of a recombinant protein on a preparative HPLC column.

LIR-P3G2 DNA in pDC406 vector was deposited with the American Type Culture Collection on Apr. 22, 1997 and assigned accession No. 97995. The deposit was made under the terms of the Budapest Treaty.

As described above, LIR-P3G2 is a MHC class I receptor molecule found on the surface of certain monocytes, B cells, and NK cells. Certain LIR family members have the ITIM motif and by analogy with the structure and function of known MHC class I receptor molecules, are inhibitory receptors mediating negative signaling. Other LIR family members lack the ITIM motif and by analogy with the structure and function of known MHC class I receptors are activatory receptors. Failure of a receptor that mediates negative signaling could result in autoimmune diseases. Thus, engaging an LIR family member having ITIM motifs with an agonistic antibody or ligand can be used to downregulate a cell function in disease states in which the immune system is overactive and excessive inflammation or immunopathology is present. On the other hand, using an antagonistic antibody specific to the ITIM possessing LIR receptor or a soluble form of the receptor can be used to block the interaction of the cell surface receptor with the receptor's ligand to activate the specific immune function in disease states associated with suppressed immune function. Since receptors lacking the ITIM motif send activatory signals once engaged as described above, failure of a receptor that mediates an activatory signal could result in suppressed immune function. Engaging the receptor with its agonistic antibody or ligand can be used to treat diseases associated with the suppressed immune function. Using an antagonistic antibody specific to the activatory LIR receptor or a soluble form of the receptor can be used to block the interaction of the activatory receptor with the receptor's ligand to downregulate the activatory signaling.

Since LIR-P3G2 binds to various cells, LIR-P3G2 may be used to purify or isolate these cells from heterogeneous preparations. Additionally, P3G2 probes can be used to isolate and identify related molecules.

LIR polypeptides of the present invention may be used in developing treatments for any disorder mediated directly or indirectly by defective or insufficient amounts of any of the LIR polypeptides. A therapeutically effective amount of purified LIR protein is administered by a patient afflicted with such a disorder. Alternatively, LIR DNA may be employed in developing a gene therapy approach to treating such disorders. Disclosure herein of native LIR nucleotide sequence permits the detection of defective LIR genes, and the replacement thereof with normal LIR-encoding genes. Defective genes may be detected in vitro diagnostic assays, and by comparison of the native LIR nucleotide sequence disclosed herein with that of an LIR gene derived from a person suspected of harboring a defect in the gene.

The present invention also provides pharmaceutical compositions which may include an LIR polypeptide, or fragments or variants thereof with a physiologically acceptable carrier or diluent. Such carriers and diluents will be nontoxic to recipients at the dosages and concentrations employed. Such compositions may further include buffers, antioxidants such as ascorbic acid, low molecular weight (less than about ten residues) polypeptides, proteins, amino acids, carbohydrates including glucose, sucrose or dextrins, chelating agents such as EDTA, glutathione and other stabilizers and excipients commonly used in pharmaceutical compositions. The pharmaceutical compositions of the present invention may be formulated as a lyophilizate using appropriate excipient solutions as diluents. The pharmaceutical compositions may include an LIR polypeptide in any for described herein, including but not limited to active variants, fragments, and oligomers. LIR polypeptides may be formulated according to known methods that are used to prepare pharmaceutically useful compositions. Components that are commonly employed in pharmaceutical formulations include those described in *Remington's Pharmaceutical Sciences,* 16th ed. (Mack Publishing Company, Easton, Pa., 1980).

The pharmaceutical preparations of the present invention may be administered to a patient, preferably a human, in a manner appropriate to the indication. Thus, for example, the compositions can be administered by intravenous injection, local administration, continuous infusion, sustained release from implants, etc. Appropriate dosages and the frequency of administration will depend on such factors as the nature and severity of the indication being treated, the desired response, the condition of the patient and so forth.

In preferred embodiments an LIR polypeptide used in the pharmaceutical compositions of the present invention is purified such that the LIR polypeptide is substantially free of other proteins of natural or endogenous origin, desirably containing less than about 1% by mass of protein contaminants residual of the production processes. Such compositions, however, can contain other proteins added as stabilizers, carriers, excipients or co-therapeutics.

LIR encoding DNAs and DNA fragments disclosed herein find use in the production of LIR polypeptides, as described above. In one embodiment, such fragments comprise at least about 17 consecutive nucleotides, more preferably at least 30 consecutive nucleotides, of LIR DNA. DNA and RNA complements of the fragments have similar utility. Among the uses of LIR nucleic acid fragments are as probes or primers in polymerase chain reactions. For example, a probe corresponding to a fragment of DNA encoding the extracellular domain of LIR may be employed to detect the presence of LIR nucleic acids in in vitro assays and in other probing assays such as Northern Blot and Southern blot assays. Cell types expressing an LIR polypeptide can be identified using LIR family nucleic acid probes using probing procedures well known in the art. Those skilled in the art have the knowledge to choose a probe of suitable length and apply conventional PCR techniques to isolate and amplify a DNA sequence.

Nucleic acid fragments may also be used as a probe in cross species hybridization procedures to isolate LIR DNA from other mammalian species. As one example, a probe corresponding to the extracellular domain of an LIR polypeptide may be employed. The probes may be labeled (e.g., with $^{32}P$) by conventional techniques.

Other useful fragments of LIR nucleic acids are antisense or sense oligonucleotides which include a single-stranded nucleic acid sequence (either RNA or DNA) capable of binding to a target LIR mRNA (sense) or P3G2 DNA (antisense) sequences. Such fragments are generally at least about 14 nucleotides, preferably from about 14 to about 30 nucleotides. The ability to create an antisense or a sense oligonucleotide based upon a cDNA sequence for a given protein is described in, for example, Stein and Cohen, *Cancer Res.* 48:2659, 1988 and van der Krol et al., *BioTechniques* 6:958, 1988.

Binding antisense or sense oligonucleotides to target nucleic acid sequences results in the formation of duplexes that block translation (RNA) or transcription (DNA) by one of several means, including enhanced degradation of the duplexes, premature termination of transcription or translation, or by other means. The antisense oligonucleotides thus may be used to block LIR expression.

In one embodiment antisense or sense LIR oligonucleotides used in binding procedures may encompass oligonucleotides having modified sugar-phosphodiester backbones (or other sugar linkages, such as those described in WO91/06629) and wherein such sugar linkages are resistant to endogenous nucleases. Oligonucleotides having sugar linkages resistant to endogenous nucleases are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increase affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by inserting he antisense or sense oligonucleotide into a suitable retroviral vector, then contacting the cell with the retroviral vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugating the ligand binding molecule does not substantially interfere with the ability of the ligand binding molecule to bind its corresponding molecule or receptor, or block entry of the sense of antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In still a further aspect, the present invention provides antibodies that specifically bind LIR polypeptides, i.e., antibodies bind to LIR polypeptides via an antigen-binding site of the antibody (as opposed to non-specific binding). Antibodies of the present invention may be generated using LIR polypeptides or immunogenic fragments thereof. Polyclonal and monoclonal antibodies may be prepared by conventional techniques. See, for example, Monoclonal Antibodies, Hybridomas: A New Dimension in Biological Analyses, Kennet et al. (eds.), Plenum Press, New York 1980; and *Antibodies: A Laboratory Manual*, Harlow and Land (eds.), Cold Spring Harbor Laboratory Press, Cold Spring Harbor, N.Y., 1988. An exemplary procedure for producing monoclonal antibodies immunoreactive with P3G2-LIR is further illustrated in Example 5 below.

Included within the scope of the present invention are antigen binding fragments of antibodies which specifically bind to an LIR polypeptide. Such fragments include, but are not limited to, Fab, F(ab'), and F(ab')$_2$. Antibody variants and derivatives produced by genetic engineering techniques are contemplated as within the presented invention.

The monoclonal antibodies of the present invention include chimeric antibodies, e.g., humanized versions of murine monoclonal antibodies. Such antibodies may be prepared by known techniques and offer the advantage of reduced immunogenicity when the antibodies are administered to humans. In one embodiment a humanized monoclonal antibody comprises the variable region of a murine antibody (or just the antigen binding site thereof) and a constant region derived from a human antibody. Alternatively, a humanized antibody fragment may comprise the antigen binding site of a murine monoclonal antibody and a variable region fragment (lacking the antigen-binding site) derived from a human antibody. Procedures for the production of chimeric and further engineered monoclonal antibodies include those described in Riechmann et al., *Nature* 332:232, 1988; Lie et al. *PNAS* 84:3439, 1987; Larrick et al. *Bio/Technology* 7:934, 1989; and Winter and Harris *TIPS* 14:139, 1993.

As mentioned above, antibodies of the present invention are useful in in vitro or in vivo assays to detect the presence of LIR polypeptides and in purifying an LIR polypeptide by affinity chromatography.

Additionally, antibodies capable of blocking an LIR from binding to target cells may be used to inhibit a biological activity of an LIR polypeptide. More specifically, therapeutic compositions of an antibody antagonistic to one or more LIR family members having the ITIM motif may be administered to an individual in order to block the interaction of a cell surface LIR with its ligand. The result is an activation of immune function and is particularly beneficial in disease states in which the immune system is hyporesponsive or suppressed. Conversely, therapeutic compositions of an antibody antagonistic to one or more LIR family members lacking the ITIM motif may be used to obtain the opposite effect and be beneficial in disease states in which the immune system is overactive and excessive inflammation or immunopathology is present.

Pharmaceutical compositions which include at least one antibody that is immunoreactive with an LIR polypeptide and a suitable diluent, excipient, or carrier, are considered with the present invention. Suitable diluents, excipients, and carriers are described in the context of pharmaceutical compositions which include polypeptides of the present invention.

The following examples are provided to illustrate certain embodiments of the invention, and are not to be construed as limiting the scope of the invention.

EXAMPLES

Example 1

Isolating and Expressing Viral Protein

DNA encoding P3G2 polypeptide of the present invention was identified by isolating and expressing a viral glycoprotein, UL18, known to be expressed on cells infected with HCMV, and then expressing and using a UL18/Fc fusion protein to search for UL18 receptors. DNA encoding UL18 and its amino acid sequence are known and described in Beck, S., B. G. Barrell, *Nature* 331:269–272, 1988. The following describes isolating UL18 and preparing the UL 18/Fc fusion protein.

Using standard techniques, total RNA was isolated from Human Foreskin Fibroblasts infected with HCMV (AD169) at three different transcription stages-immediate early (IE, 8 p.i.h.), early (24 p.i.h.) and late (48 p.i.h.). Because UL18 is known to be transcribed early in the infection, the IE total RNA was polyA+ selected and used to construct an HCMV-IE cDNA library using a cDNA kit according to the manufacturer's instructions (Pharmacia TIME SAVER cDNA Kit). In order to isolate the full length UL18 gene, two oligonucleotide primers known to include the terminal sequences of the UL18 gene were synthesized and used to isolate and amplify the UL18 gene from the HCMV-IE cDNA library. The primers had the following sequences and included Not I restriction sites which incorporate into the PCR product.

```
         Not I
5' - TAT GCG GCC GCC ATG ATG ACA ATG TGG T - 3'   (SEQ ID NO:23)

5' - TAT GCG GCC GCC CCT TGC GAT AGC G - 3'       (SEQ ID NO:24)
         Not I
```

The PCR conditions included one 5 minute 95° C. cycle followed by 30 cycles of 45 seconds at 95°, 45 seconds at 58° and 45 seconds at 72°, and then one cycle for 5 minutes at 72° C. The PCR product was electrophoresed on a 1% agarose gel and sized using ethidium bromide to visualize the separated DNA products. The presence of DNA of having the expected size of approximately 1.1 kb was confirmed.

The pDC409 expression vector, a vector derived from pDC406 (McMahan et al., *EMBO J.* 10:2821, 1991) but having a single Bgl II site was selected for the cloning process. The PCR product was subcloned into a pDC409 expression vector through the Not I sites, sequenced and the amino acid sequence deduced from the DNA sequence. The determined nucleotide sequence and amino acid sequence were identical to the previously published sequences (ibid.).

A fusion protein of the extracellular region of UL18 and a mutein human IgG1 Fc region (UL18:Fc) was prepared by first isolating cDNA encoding the extracellular region of UL18 using primers which flank the extracellular region of UL18. The primers were synthesized with Sal I and Bgl II restriction sites inserted at the 5' and 3' termini so that the PCR amplified cDNA introduced Sal I and Bgl II restriction sites at the 5' and 3' ends, respectively. The primers had the following sequences:

```
5' - ATA GTC GAC AAC GCC ATG ATG ACA ATG TGG TG - 3'   (SEQ ID NO:25)
         Sal I

5' - TAA AGA TCT GGG CTC GTT AGC TGT CGG GT - 3'       (SEQ ID NO:26)
         BglII
```

The conditions for the PCR reaction were as described above except that the template was the full length gene isolated as just described.

To prepare a vector construct for expressing fusion protein, sUL18:Fc, for use in cell binding studies, a DNA fragment encoding the Fc region of a human IgG1 antibody was isolated from a plasmid using Bgl II and Not I restriction enzymes. The encoded Fc portion was the mutein Fc described in U.S. Pat. No. 5,457,035 having reduced affinity for immunoglobulin receptors. The Bgl II site on the sUL18 gene was used to ligate the sUL18 gene DNA to the Bgl II site on the Fc gene to form a sUL18:Fc fusion DNA construction having an N-terminal Sal I restriction site and a C-terminal Not I restriction site. This fusion sUL18:Fc DNA construct was then ligated into pDC409 expression vector at its Sal I and Not I sites to form a 409/sUL18/Fc DNA construct.

The monkey cell line COS-1 (ATCC CRL-1650) was used to confirm expression of the fusion protein. COS-1 cells in 6-well plates (2×10$^5$ cells per well) were transfected with about 2 μg of the DNA construct 409/sUL18/Fc per well. The cells were cultured for 2–3 days in 5% FBSDMEM/F12 (available from GIBCO), then washed twice with PBS, starved for 1 hour in cysteine/methionine depleted RPMI (available from GIBCO as RPMI 1640) and metabolically labeled with 100 μCi/mL of $^{35}$S-Met/Cys for 4 hours. The supernatant was spun clear to remove loose cells and 150 μL of the supernatant was incubated with 100 μL of RIPA (0.05% Tween 20, 0.1% SDS, 1% Triton X-100, 0.5% deoxycholate in PBS) buffer and 50 μL of 50% Protein A-Sepharose solid support beads at 4° C. for 1 hour. Protein A-Sepharose is a Sepharose solid support (available from Pharmacia) having immobilized Protein A which binds the Fc portion of the fusion protein. After washing the solid support with RIPA to remove unbound material, fusion protein bound to the Protein A-Sepharose solid support was eluted from the Protein A-Sepharose using 35 μL of SDS-PAGE reducing sample buffer and then heated at 100° C. for 5 minutes. The eluant was then electrophoresed on a 4–20% SDS polyacrylamide gradient gel with $^{14}$C labeled protein molecular weight markers. After electrophoresis the gel was fixed with 8% acetic acid and enhanced at room temperature for 20 minutes with Amplifier available from Amersham. After drying the gel under vacuum it was exposed to x-ray film. Film analysis confirmed that the expected protein, a 100–120 kDa protein which includes the mutein Fc region of IgG and UL18 extracellular domains fused to the Fc, was expressed.

Once cells expressing the fusion protein were identified large scale cultures of transfected cells were grown to accumulate supernatant from cells expressing the fusion protein. This procedure involved transfecting COS-1 cells in T175 flasks with 15 μg of the UL18/Fc/409 fusion DNA per flask. After 7 days of culture in medium containing 0.5% low immunoglobulin bovine serum, a solution of 0.2% azide was added to the supernatant and the supernatant was filtered through a 0.22 μml filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc portion of the sUL18/Fc fusion protein in the supernatant, immobilizing the fusion protein and allowing other components of the supernatant to pass through the column. The column was washed with 30 mL of PBS solution and bound sUL18/Fc was eluted from the HPLC column with citric acid adjusted to pH 3.0. Eluted purified sUL18/Fc was neutralized as it eluted using 1M Hepes solution at pH 7.4. The pooled eluted protein was analyzed using SDS PAGE with silver staining, confirming expression of the 100–120 kDa UL18/Fc fusion protein.

Example 2

Screening Cell Lines for Binding to UL18

The sUL18/Fc protein isolated as described in Example 1 was used to screen cells lines to which it binds using quantitative binding studies according to standard flow cytometry methodologies. For each cell line screened, the procedure involved incubating approximately 100,000 of the cells blocked with 2% FCS (fetal calf serum), 5% normal goat serum and 5% rabbit serum in PBS for 1 hour. Then the blocked cells were incubated with 5 µg/mL of sUL18/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the anti human Fc/biotin to bind to any bound sUL18/Fc and the SAPE to bind to the anti human Fc/biotin resulting in a fluorescent identifying label on sUL18/Fc which is bound to cells. The cells were analyzed for any bound protein using fluorescent detection flow cytometry. The results indicated that UL18 binds well to B cell lines CB23, RAJI and MP-1; monocytic cell lines Thp-1 and U937; and primary B cell and primary monocytes. UL18 does not bind detectably to T cell lines nor does it bind to primary T cells.

Example 3

Isolating a P3G2 cDNA and Polypeptide

The following describes screening cDNA of one of the cell lines found to bind UL18 and the isolation of a novel polypeptide expressed by the cell line. A CB23 cDNA library in the mammalian expression vector pDC406, prepared as described in U.S. Pat. No. 5,350,683 (incorporated herein by reference) was obtained and plasmid DNA was isolated from pools consisting of approximately 2,000 clones per pool. The isolated DNA was transfected into CV1-EBNA cells (ATCC CRL 10478) using DEAE-dextran followed by chloroquine treatment. The CV1-EBNA cells were maintained in complete medium (Dulbecco's modified Eagles' media containing 10% (v/v) fetal calf serum, 50 U/mL penicillin, 50 U/mL streptomycin, and 2 mM L-glutamine) and were plated to a density of approximately $2\times10^5$ cells/well in single-well chambered slides. The slides had been pre-treated with 1 mL of a solution of 10 µg/mL human fibronectin in PBS for 30 minutes followed by a single washing with PBS. Media was removed from adherent cells growing in a layer and replaced with 1.5 mL complete medium containing 66.6 µM chloroquine sulfate. About 0.2 mL of a DNA solution (2 µg DNA, 0.5 mg/mL DEAE-dextran in complete medium containing chloroquine) was added to the cells and the mixture was incubated at 37 C for about five hours. Following incubation, the media was removed and the cells were shocked by addition of complete medium containing 10% DMSO (dimethylsulfoxide) for 2.5 minutes. Shocking was followed by replacing the solution with fresh complete medium. The cells were grown in culture for two to three days to permit transient expression of the inserted DNA sequences. These conditions led to a 30% to 80% transfection frequency in surviving CV1-EBNA cells.

Each slide was incubated with 1 mL of UL18:Fc at a concentration of 11 µg/mL in binding buffer (RPMI 1640 containing 25 mg/mL bovine serum albumin, 2 mg/mL sodium azide, 20 mM Hepes at pH 7.2, and 50 mg/mL nonfat dry milk) at room temperature for 1 hour. The incubated slides were washed with the binding buffer and then incubated with Fc specific $^{125}$I-mouse anti-human IgG (see Goodwin et al., Cell 73:447–456, 1993). This was followed by a second wash with buffer after which the slides were fixed with a 2.5% glutaraldehyde/PBS solution, washed with PBS solution and allowed to air dry. The dried slides were dipped in Kodak GTNB-2 photographic emulsion (6× dilution in water). After air drying, the slides were placed in a dark box and refrigerated. After three days the slides were developed in Kodak D19 developer, rinsed in water and fixed in Agfa G433C fixer. The fixed slides were individually examined under a microscope at 25–40× magnification. Positive cells demonstrating binding of sUL18:Fc were visualized by the presence of autoradiographic silver grains against the film background. Two positive pools were identified. Bacterial clones from each pool were titered and plated to provide plates containing approximately 200 colonies each. Each plate was scraped to provide pooled plasmid DNA for transfection into CV1-EBNA cells and screening as described above. Following subsequent breakdowns and screenings, two positive individual colonies were obtained. The cDNA inserts of the two positive clones were 2922 and 2777 nucleotides in length as determined by automated DNA sequences. The coding regions of the two inserts, designated P3G2 and 18A3 were 1953 (nucleotides 310–2262) and 1959 (nucleotides 168–2126) nucleotides, respectively. The two cDNA clones encode proteins that are substantially similar and probably represent different alleles of the same gene.

The cDNA sequence and encoded amino acid of P3G2 are presented in SEQ ID NO:1 and SEQ ID NO:2, respectively. The cDNA sequence and encoded amino acid of 18A3 are presented in SEQ ID NO:3 and SEQ ID NO:4, respectively. The P3G2 amino acid sequence (SEQ ID NO:2) has a predicted signal peptide of 16 amino acids (amino acids 1–16); an extracellular domain of 442 amino acids (amino acids 17–458); a transmembrane domain of 25 amino acids (amino acids 459–483) and, a cytoplasmic domain of 167 amino acids (amino acids 484–650. The extracellular domain includes four immunoglobulin-like domains. Ig-like domain I includes approximately amino acids 17–118; Ig-like domain II includes approximately amino acids 119–220; Ig-like domain III includes approximately amino acids 221–318; and Ig-like domain IV includes approximately amino acids 319–419. Significantly, the cytoplasmic domain of this polypeptide includes four ITIM motifs, each having the consensus sequence of YxxL/V. The first ITIM motif pair is found at amino acids 533–536 and 562–565 and the second pair is found at amino acids 614–617 and 644–647. The amino acid sequence of 18A3 is nearly identical having the features describes above.

The features of these encoded polypeptides are consistent with a type I transmembrane glycoprotein.

Example 4

Preparing P3G2 Fusion Protein

The following describes procedures used to generate a P3G2 fusion protein which was then used to identify cell lines to which it binds and finally isolate a normal cell-surface P3G2 ligand which is distinct from UL18. A fusion protein of the extracellular region of P3G2 and the mutein human Fc region (sP3G2:Fc) was prepared by first isolating cDNA encoding the extracellular region of P3G2 using primers which flank the extracellular region of P3G2. The primers were synthesized with Sal I and Bgl II restriction sites inserted at the 5' and 3' termini so that the PCR amplified cDNA introduced Sal I and Bgl II restriction sites at the 5' and 3' ends, respectively. The primers had the following sequences:

```
              Sal I
5' - TAT GTC GAC CAT GAC CCC CAT CCT CAC GGT - 3'                          (SEQ ID NO:5)

Bgl II      Xa
5' - TAT GGG CTC TGC TCC AGG AGA AGA TCT TCC TTC TAT AAC CCC CAG GTG CCT T  (SEQ ID NO:6)
```

The conditions for the PCR reaction were as described above and the template was the full length gene P3G2 gene isolated as described in Example 3 above.

To prepare a vector construct for expressing fusion protein sP3G2:Fc for use in cell binding studies, the mutein human Fc region of IgG 1 was cut from the plasmid described above in Example 1 using Bgl II and Not I restriction enzymes. The Bgl II site on the sP3G2 gene was used to ligate the sP3G2 gene DNA to the Bgl II site on the human mutein Fc gene to form a sP3G2/Fc fusion DNA construction having an N-terminal Sal I restriction site and a terminal Not I restriction site. This fusion sP3G2:Fc DNA construct was then ligated into pDC409 expression vector at its Sal I and Not I sites to form a 409/sP3G2/Fc DNA construct.

The monkey cell line COS-1 (ATCC CTL-1650) was used to confirm expression of the fusion protein. COS-1 cells in 6-well plates (2×10⁵ cells per well) were transfected with about 2 μg of the DNA construct 409/sP3G2/Fc per well. The cells were cultured in 5% FBS/DMEM/F12 (available from GIBCO) and at day two or three following transfection, the cells were starved for 1 hour in cysteine/methionine depleted RPMI and the transfected cells were metabolically labeled with 100 μCi/mL of $^{35}$S-Met/Cys for 4 hours. The supernatant was spun clear to removed loose cells and debris and 150 μL of the supernatant was incubated with 100 μL of RIPA buffer and 50 μL of 50% Protein A-Sepharose solid support beads at 4° C. for 1 hour. After washing the solid support with RIPA to remove unbound material, fusion protein bound to the Protein A-Sepharose solid support was eluted from the Protein A-Sepharose using 30 μL of SDS-PAGE reducing sample buffer and then heated at 100° C. for 5 minutes. The eluant was then electrophoresed on a 4–20% SDS polyacrylamide gradient gel with $^{14}$C labeled protein molecular weight markers. After electrophoresis the gel was fixed with 8% acetic acid and enhanced at room temperature for 20 minutes with Amplifier available from Amersham. After drying the gel under vacuum it was exposed to x-ray film. Film analysis confirmed that the expected protein, having a molecular weight of 120–130 kDa, was expressed.

Once fusion protein expression was verified, large scale cultures of transfected cells were grown to accumulate supernatant from COS-1 cells expressing the fusion protein as described in Example 1 above. The P3G2/Fc fusion protein was purified according to the procedure described in Example 3 above using the BioCad system and the POROS 20A column from PerSeptive Biosystems. The pooled eluted protein was analyzed using SDS PAGE with silver staining, confirming expression.

Example 5

Generating LIR-P3G2 Antibody

The following example describes generating monoclonal antibody to P3G2 that was used in flow cytometry analysis to identify cells on which P3G2 is expressed. Purified P3G2/Fc fusion protein was prepared by COS-1 cell expression and affinity purification as described in Example 4. The purified protein or cells transfected with an expression vector encoding the full length protein can generate monoclonal antibodies against P3G2 using conventional techniques, for example those techniques described in U.S. Pat. No. 4,411,993. Briefly BALB-C mice were immunized at 0, 2 and 6 weeks with 10 μg P3G2/Fc. The primary immunization was prepared with TITERMAX adjuvant, from Vaxcell, Inc., and subsequent immunization were prepared with incomplete Freund's adjuvant (IFA). At 11 weeks, the mice were IV boosted with 3–4 μg P3G2 in PBS. Three days after the IV boost, splenocytes were harvested and fused with an Ag8.653 myeloma fusion partner using 50% aqueous PEG 1500 solution. Hybridoma supernatants were screened by ELISA using P3G2 transfected COS-1 cells in PBS at 2×10³ cells per well and dried to polystyrene 96-well microtiter plates as the platecoat antigen. Positive supernatants were subsequently confirmed by FACS analysis and RIP using P3G2 transfected COS-1 cells. Hybridomas were cloned and followed using the same assays. Monoclonal cultures were expanded and supernatants purified by affinity chromatography using BioRad Protein A agarose.

The monoclonal antibodies to P3G2/Fc were used to screen cells and cell lines using standard flow cytometry procedures to identify cells on which P3G2 is expressed. Cell lines and cells screened in the flow cytometry analyses were CB23, CB39, RAJI, AK778, K299, PS-1, U937, THP-1, JURKAT and HSB2. For each cell line or cell sample screened, the procedure involved incubating approximately 100,000 of the cells blocked with 2% FCS (fetal calf serum), 5% normal Goat serum and 5% rabbit serum in PBS with 5 μg of FITC conjugated mouse anti-P3G2 antibody for 1 hour. Following the incubation the sample was washed 2 times with FACS buffer (2% FCS in PBS). The cells were analyzed for any bound protein using fluorescent detection flow cytometry to detect FITC. The results indicated that LIR-P3G2 antibody binds well to B cell lines CB23 and RAJI1; monocytic cell lines THP-1 and U937; and primary B cell and primary monocytes. The highest expression of LIR-P3G2 was shown on monocytes that stained brightly for CD16 and less brightly for CD14 and CD64. The antibody does not bind detectably to T cell lines nor does it bind detectably to primary T cells.

In a related experiment, the P3G2 antibody generated as described above was used in immunoprecipitation experiments. The immunoprecipitation analyses involved first surface biotinylating 2.5×10⁶ monocytes by washing the cells with PBS and suspending the cells in a biotinylation buffer of 10 mM sodium borate and 150 mM NaCl at pH 8.8, followed by adding 5 μL of a 10 mg/mL solution of biotin-CNHS-ester (D-biotinoyl-e-aminocaproic acid-N-hydroxysuccinimide ester purchased from Amersham) in DMSO to the cells. After quenching the reaction with 10 μL of 1 M ammonium chloride per 1 mL of cells and washing the cells in PBS, the cells were lysed in 1 mL of 0.5% NP40-PBS and the lysate was recovered following centrifugation. Then 100 μL of 0.5%NP40-PBS was added to 150 μL of the lysate and the resulting mixture was incubated with 2 μg/mL of antibody, at 4° C. for 16 hours. Fifty microliters of 50% Protein A-Sepharose slurry was added to the antibody mixture and the slurry was shaken at 4° C. for 1 hour. The slurry was centrifuged and the resulting pellet was washed with 0.75 mL of 0.5% NP40 in PBS six times. Protein bound to the Protein A-Sepharose was eluted with 30 μL of SDS-PAGE reducing sample buffer and heating at 100° C. for five minutes.

The eluted proteins were analyzed using 4–20% gradient SDS-PAGE with enhanced chemiluminescence (ECL) protein markers. Then the electrophoreses samples were transferred in a Western Blot onto nitrocellulose membranes. The membranes were treated with blocking reagent (0.1% Tween-20 and 3% nonfat dry milk in PBS) for one hour at room temperature and then they were washed once for 15 minutes followed and twice for 5 minutes with 0.1% Tween-20 in PBS. The washed membranes were incubated with 10 mL of 1:100 HRP-Streptavidin for 30 minutes and then washed 1 times for 15 minutes followed by 4 times for 5 minutes with 0.1% Tween-20 in PBS.

Bound streptavidin HRP was detected with ECL Detection Reagents purchased from Amersham and used according to manufacturer's instructions. The developed membranes were exposed to x-ray film and then visualized. The results showed that LIR-P3G2 was immunoprecipitated from CB23 cells and P3G2 transfected COS-1 cells, indicating that P3G2 is expressed by these cells.

Example 6

Screening Cells and Cell Lines for Binding to P3G2

The following describes flow cytometry analyses used to identify cells and cell lines which bind to P3G2. The cells and cell lines tested were CB23, HSB2, MP-1, Jurkat, primary T cells, primary B cells, and primary NK cells. For each cell line or cell line tested the procedure involved washing the cells three times with FACS buffer (2% FCS in PBS with 0.2% azide) and incubating each sample ($10^5$ cells) in 100 μL blocking buffer (2% FCS, 5% NGS, 5% rabbit serum in PBS) for one hour. For each cell line 4 test samples were prepared, one each having 0, 2, 5, or 10 μg of W6/32 (ATCC HB-95) in 100 μL blocking buffer added to the samples, respectively. W6/32 is an antibody against MHC Class I heavy chains (an anti HLA-A, B, and C molecule). Following the addition of the W6/32 solution, the samples were incubated on ice for 1 hour and then washed three times with 200 μL of FACS buffer. Then 5 μg of P3G2/Fc in blocking buffer was added to each sample and they were incubated on ice for one hour. The P3G2/Fc competes with W6/32 for binding sites on the cells.

Following the incubation, the cells were washed three times with 200 μL of FACS buffer and treated with mouse anti human Fc/biotin and SAPE for 45 minutes. This treatment causes the anti human Fc/biotin to bind to any cell bound sP3G2/Fc and the SAPE to bind to the anti human F/Biotin. Since the SAPE is a fluorescing compound its detection using appropriate excitation and emission conditions positively identifies cell bound P3G2/Fc. Finally the treated cells were washed three times with FACS buffer and subjected to flow cytometry to identify cells bound to protein.

The results demonstrated that W6/32 competed with P3G2 for binding to all cells and cell lines tested. The P3G2 binding was totally blocked at 5 μg W6/32 indicating that W6/32 and P3G2 are binding to the same or overlapping sites on the MHC Class I heavy chains.

Example 7

Screening HSB2 cDNA Library to Isolate a P3G2 Binding Ligand

The following describes screening a cDNA library from of one of the cell lines, HSB-2, a T lymphoblastic leukemia cell line, found to bind P3G2, and identifying a P3G2 binding ligand. An HSB2 cDNA library in the mammalian expression vector pDC302, was prepared as generally described in U.S. Pat. No. 5,516,658 and specifically in Kozlosky et al. *Oncogene* 10.299–306, 1995. Briefly, mRNA was isolated from sorted HSB-2 cells and a first cDNA strand was synthesized using 5 μg polyA$^+$ and the reverse transcriptase AMV RTase from Life Science. The second cDNA strand was synthesized using DNA polymerase I from BRL at concentration of 1.5 U/μL. Using standard techniques as described in Haymerle et al., *Nucl. Acids Res.* 14:8615, 1986, the cDNA was ligated into the appropriate site of the pDC302 vector.

*E. coli.* strain DH5α cells were transformed with the cDNA library in pDC302. After amplifying the library a titer check indicated that there was a total of 157,200 clones. The transformed cells were plated into 15 different plates. Plasmid DNA was isolated from pools consisting of approximately 2,000 clones per pool. The isolated DNA was transfected into CV1-EBNA cells (ATCC CRL 10478) using DEAE-dextran followed by chloroquine treatment. The CV1-EBNA cells were maintained in complete medium (Dulbecco's modified Eagles' media containing 10% (v/v) fetal calf serum, 50 U/mL penicillin, 50 U/mL streptomycin, and 2 mM L-glutamine) and were plated to a density of approximately $2\times10^5$ cells/well in single-well chambered slides. The slides had been pre-treated with 1 mL of a solution of 10 μg/mL human fibronectin in PBS for 30 minutes followed by a single washing with PBS. Media was removed from adherent cells growing in a layer and replaced with 1.5 mL complete medium containing 66.6 μM chloroquine sulfate. About 0.2 mL of a DNA solution (2 μg DNA, 0.5 mg/mL DEAE-dextran in complete medium containing chloroquine) was added to the cells and mixture was incubated at 37 C for about five hours. Following incubation media was removed and the cells were shocked by adding complete medium containing 10% DMSO for 2.5 minutes. After shocking the cells the complete medium was replaced with fresh complete medium and the cells were grown in culture for three days to permit transient expression of the inserted DNA sequences. These conditions led to a 30% to 80% transfection frequency in surviving CV1-EBNA cells.

Each slide was incubated with 1 mL of P3G2:Fc at a concentration of 0.45 μg/mL in binding buffer (RPMI 1640 containing 25 mg/mL bovine serum albumin, 2 mg/mL sodium azide, 20 mM Hepes at pH 7.2, and 50 mg/mL nonfat dry milk) at room temperature for 1 hour. After incubating the slides, they were washed with binding buffer and then incubated with Fc specific $^{125}$I-mouse anti-human IgG (see Goodwin et al. *Cell* 73:447–456, 1993). This was followed by a second wash with buffer after which the slides were fixed with a 2.5% glutaraldehyde/PBS solution, washed in PBS and allowed to air dry. The slides were dipped in Kodak GTNB-2 photographic emulsion (6× dilution in water). After air drying the slides were placed in a dark box and refrigerated. After three days the slides were developed in Kodak D19 developer, rinsed in water and fixed in Agfa G433C fixer. The fixed slides were individually examined under a microscope at 25–40× magnification. Positive pools demonstrating binding of sP3G2:Fc were visualized by the presence of autoradiographic silver grains against the film background. Two positive pools were titered and plated to provide plates containing approximately 200 colonies each. Each plate was scraped to provide pooled plasmid DNA for transfection into CV1-EBNA cells and screening as described above. Following subsequent breakdowns and screenings, one positive individual colony was obtained for each pool. The cDNA insert of the positive clones were identified as HLA-B44 and HLA-A2, class I MHC antigens.

Example 8

Northern Blot Analysis

Since the experiments described in Example 4 resulted in the detection of LIR-P3G2 surface expression on a number of cell lines, conventional Northern Blot analysis procedures were used to study the expression of LIR-P3G2 and any LIR-P3G2 related mRNAs in different tissue types. The cell lines selected for Northern Blot analysis were RAJI, PBT, PBM, YT, HEP3B, HELA, KB, KG-1, IMTLH, HPT, HFF, THP-1, and U937. The following describes the Northern Blot analysis and the analysis results.

The cDNA encoding the extracellular region of P3G2 was isolated using primers which flank the extracellular region of P3G2 and having the following sequences:

```
        Sal I
5' - TAT GTCGAC CAT GAC CCC CAT CCT CAC GGT - 3'   (SEQ ID NO:5)

Bgl II
5' - TAT AGATCT ACC CCC AGG TGC CTT CCC AGA CCA    (SEQ ID
                                                   NO:27)
```

The PCR template was the full length P3G2 gene isolated as described in Example 3 above. The conditions for the PCR reaction were as follows: One cycle at 95° C. for 5 minutes; 30 cycles which included 95° C. for 45 seconds, 64° C. for 45 seconds and 72° C. for 45 seconds; and, one cycle at 72° C. for 5 minutes. The PCR product was cloned into PCR II vector, purchased from Invitrogen, in accordance with the supplier's instructions. The isolated DNA encoding the extracellular region of P3G2 was used to make a riboprobe with the Ambion MAXISCRIPT Kit according to the manufacturer's instructions.

Northern blots containing poly A+ selected RNA or total RNA from a variety of human cell lines were prepared by resolving RNA samples on a 1.1% agarose-formaldehyde gel, blotting onto Hybond-N as recommended by the manufacturer (Amersham Corporation) and staining with methylene blue to monitor RNA concentrations. The blots were prepared using 1 µg of the PolyA+ RNA or 10 µg of total RNA and each blot was probed with $10^6$ cpm/mL RNA extracellular P3G2 riboprobe, prepared as just described, at 63° C. for 16 hours. The probed blots were washed with 2×SSC at 63° C. for 30 minutes 2 times; 1×SSC at 63° C. for 30 minutes 2 times; and, 0.1×SSC at 63° C. for 5 minutes 2 times.

The probed blots were autoradiographically developed. The developed blots showed that the P3G2 RNA hybridized to a 3.5 kb RNA expressed by RAJI, CB23 and U937; an approximately 1.5 kb RNA expressed by THP-1; and multiple RNAs ranging from 1.5 kb to 3.5 kb expressed by PBM. These results suggest that different genes having extracellular domains similar in structure to that of P3G2 may be expressed by peripheral blood monocytes.

Example 9

Probing PBM cDNA Library to Isolate LIR Polypeptides

The following describes steps taken to screen a peripheral blood monocyte cDNA library to isolate polypeptides relating to the P3G2 polypeptide using conventional Southern Blot methodologies. A peripheral blood monocyte cDNA library was prepared using substantially the same procedures described in Example 7.

DNA from an initial 15 pools of cDNA having 10,000 clones per pool was digested with Bgl II restriction enzyme and electrophoresed on a 1% agarose gel at 100 V for 2 hours. Southern Blots were prepared by electroblotting the electrophoresed DNA in 0.55% TBE buffer onto Hybond membranes. The blotted DNA was denatured in 0.5 M NaOH in 0.6M NaCl solution for 5 minutes and then neutralized in 0.5 M TRIS in 1.5 M NaCl at pH 7.8 for 5 minutes. The membranes were placed in a STRATALINKER UV crosslinker for 20 seconds to crosslink the blotted DNA to the membrane. The membrane and bound DNA were placed in pre-hybridization solution of 10× Denhart's Solution, 0.05M TRIS at pH 7.5, 0.9M NaCl, 0.1% sodium pyrophosphate, 1% SDS and 200 µg/mL salmon sperm DNA at 63° C. for 2 hours and then the bound DNA was probed with $^{32}$P labeled probe of DNA encoding the extracellular region of LIR-P3G2, including the signal peptide and Sal I and Bgl II restriction sites. The concentration of the DNA probe in hybridization solution was $10^6$ CPM per mL of hybridization solution. The probed blots were incubated for 16 hours at 63° C. and then washed with 2×SSC at 63° C. for 1 hour with one solution change; 1× with SSC at 63° C. for one hour with one solution change; and, with 0.1×SSC at 68° C. for 45 minutes with one solution change. After drying the blots they were autoradiographically developed and visualized for DNA bands which hybridized to the P3G2 extracellular DNA probe.

The results of the autoradiography visualization indicated that all pools contained DNA which hybridized to the probe. One pool showing 7 positive DNA bands was selected and subsequently subdivided to 10 pools having 3,000 clones per pool. Applying subsequent Southern Blotting methodologies to the 10 pools resulted in one pool showing 9 positively hybridizing DNA sequences. Single hybridizing clones were isolated by standard colony hybridization techniques.

Duplicate bacterial colonies on filters were probed with the P3G2 extracellular probe described above at a concentration of 500,000 cpm/mL at 63° C. for 16 hours. The hybridized filters were washed with 2×SSC at 63° C. for 30 minutes; with 1×SSC at 63° C. for 30 minutes; and finally with 0.1×SSC at 68° C. for 15 minutes.

Forty-eight clones were visualized as hybridizing on duplicate filters by autoradiography and DNA obtained from these clones using standard DNA preparation methodologies was digested with Bgl II. Then Southern Blots of the digests were obtained and probed with the P3G2 extracellular probe described above. Seven different sized cloned inserts were identified as positively hybridizing to the P3G2 probe. The nucleotide sequence of each of the inserts was obtained using automated sequencing technology. Of the 8 different cloned inserts, one was identical in sequence to LIR-P3G2. The others were identified as DNA encoding polypeptides of the new LIR family of polypeptides. The nucleotide sequences (cDNA) of the isolated LIR family members are presented in SEQ ID NO:7 (designated pbm25), SEQ ID NO:9 (designated pbm8), SEQ ID NO:11 (designated pbm36-2), SEQ ID NO:13 (designated pbm36-4); SEQ ID NO:15 (designated pbmhh); SEQ ID NO:17 (designated pbm2) and SEQ ID NO:19 (designated pbm17). The amino acid sequences encoded thereby are presented in SEQ ID NO:8 (designated pbm25), SEQ ID NO:10 (designated pbm8), SEQ ID NO:12 (designated pbm36-2), SEQ ID NO:14 (designated pbm36-4), SEQ ID NO:16 (designated pbmhh); SEQ ID NO:18 (designated pbm2); and SEQ ID NO:20 (designated pbm17).

Example 10

Screening a Human Dendritic Cell cDNA Library for LIR cDNA Sequences

The following describes the isolation and identification of an LIR family member by screening a human bone marrow-derived dendritic cell cDNA library in the λ Zap vector with a radiolabeled Hh0779 cDNA fragment. The Hh0779 cDNA fragment is a 0.7 kb insert of the Hh0779 clone previously isolated from a human dendritic cell cDNA library and obtained by restriction digestion with the enzymes PstI and-SpeI. The Hh0779 cDNA fragment was labeled with [a-$^{32}$P]dCTP using the DECAprime II DNA labeling kit purchased from Ambion.

The λ Zap cDNA library was plated at a density of 20,000 pfu per plate to provide a total of 480,000 plagues for the initial screening. The λ Zap cDNA was blotted in duplicate onto Hybond membranes, purchased from Amersham, and then denatured in a solution of 0.5N NaOH and 0.5M NaCl for 5 minutes. The membranes were neutralized in a solution of 0.5M Tris (pH 7.8) and 1.5M NaCl for 5 minutes, and then washed in 2×SSC for 3 minutes. The cDNA was crosslinked to the Hybond membranes using a STRATALINKER UV crosslinker in the auto setting.

The membranes were pre-hybridized at 65° C. for 2.25 hours in hybridization buffer containing 10× Denhardt's, 0.05M Tris (pH 7.5), 0.9M NaCl, 0.1% sodium pyrophosphate, 1% SDS and 4 mg/mL heat denatured salmon sperm DNA. After the pre-hybridization, the radio-labeled Hh0779 cDNA was added to the hybridization buffer to a final concentration of 0.54×10$^6$ cpm/mL. After 24 hours of hybridization, the membranes were washed in 0.25×SSC, 0.25% SDS at 65° C. for 1.5 hours. The blots were then exposed to autoradiographic film to visual positive clones.

A total of 146 positive clones showing hybridization signals in both membranes of a duplicate set were identified, isolated, and saved for future use. Of the 146 clones, 35 were selected for secondary screening. The selected clones were plated at low density and single clones were isolated after hybridization to the HH0779 probe using the hybridization conditions described above. The plasmids were then isolated from the λ Zap clones using the VCSM13 helper phage purchased from Stratagene. The plasmid DNA was analyzed by restriction digestion and PCR, and the clones containing the 24 largest inserts were selected and sequenced. Of the 24 sequenced clones, 6 encoded LIR-P3G2, 3 encoded LIR-pbm2, 8 encoded LIR-pbm36-4 and LIR-pbm36-2, 1 encoded LIR-pbm8, 2 encoded LIR-pmbhh, and 1 encoded a novel sequence designated LIR-pbmnew. Three clones were identified as encoding amino acid sequences that are not relevant to the LIR polypeptide family.

Example 11

Association of LIR-P3G2 and Tyrosine Phosphatase. SHP-1

The following describes the tests performed to demonstrate that LIR-P3G2 and SHP-1 associate. CB23 cells were cultured in RPMI medium supplemented with 10% FBS, concentrated by centrifugation and finally subdivided into two aliquots. One aliquot was stimulated with a solution of 50 mM/mL sodium pervanadate for 5 minutes. The second aliquot was not stimulated. After stimulation, the cells in each aliquot were immediately lysed in RIPA buffer containing 1% NP-40, 0.5% sodium deoxycholate, 50 mM Tris pH 8, 2 mM EDTA, 0.5 mM sodium orthovanadate, 5 mM sodium fluoride, 25 mM β-glycerol phosphate, and protease inhibitors. Samples of 24×10$^6$ cell equivalents were incubated for 2 hours at 4° C. with either 5 µg/mL of anti-SHP-1 antibody purchased from Transduction Laboratories, or 5 µg/mL of an isotype-matched antibody control (anti-Flag-M5 IgG1). The resulting immunocomplexes were precipitated by incubation with protein G-agarose (Boehringer Mannheim), washed, and resuspended in 40 mL of 2×SDS-PAGE sample buffer. Twenty microliters of each immuno-precipitate were loaded onto electrophoresis gels, electrophoresed under reducing conditions, and transferred to nitrocellulose membranes purchased from Amersham. Western blots were probed with anti-LIR-P3G2 polyclonal antisera and the immunocomplexes were detected by enhanced chemiluminescence (NEN).

A protein having a molecular weight of approximately 120 kDa and corresponding to LIR-P3G2 was readily detected in SHP-1 immunoprecipitates, but not in anti-Flag-M5 antibody. The LIR-P3G2 band was not seen in the absence of sodium pervanadate treatment, showing that tyrosine phosphorylation of LIR-P3G2 is essential for the association of LIR-1 and SHP-1. This data demonstrates that LIR-P3G2, by analogy with molecules possesses the ITIM motif, sends an inhibitory signal intracellularly when it interacts with its counterstructures, viral or cellular MHC class I molecules.

Example 12

Generating Antibodies Immunoreactive with LIR Polypeptides

The following describes generating monoclonal antibody immunoreactive with LIR family members. A purified LIR polypeptide is prepared by COS-1 cell expression and affinity purification as described in Example 4. The purified protein or cells transfected with an expression vector encoding the full length protein can generate monoclonal antibodies against the LIR polypeptide using conventional techniques, for example those techniques described in U.S. Pat. No. 4,411,993. Briefly BALB-C mice are immunized at 0, 2 and 6 weeks with 10 µg of the LIR polypeptide. The primary immunization is prepared with TITERMAX adjuvant and subsequent immunizations are prepared with incomplete Freund's adjuvant (IFA). At 11 weeks, the mice are IV boosted with 3–4 μg the LIR polypeptide in PBS. Three days after the IV boost, splenocytes are harvested and fused with an Ag8.653 myeloma fusion partner using 50% aqueous PEG 1500 solution. Hybridoma supernatants are screened by ELISA using the LIR transfected cells in PBS at $7 \times 10^3$ cells per well and dried to polystyrene 96-well microtiter plates as the platecoat antigen. Positive supernatants are subsequently confirmed by FACS analysis and RIP using LIR transfected cells. Hybridomas are cloned and followed in the same manner of screening. Monoclonal cultures are expanded and supernatants purified by affinity chromatography.

What is claimed is:

1. An isolated antibody or an immunoglobulin fragment thereof which specifically binds to a polypeptide comprising SEQ ID NO:2.

2. The antibody according to claim 1 which is a monoclonal antibody or an immunoglobulin fragment thereof.

3. A composition comprising the antibody or the immunoglobulin fragment thereof according to claim 1, in a pharmaceutical acceptable carrier or diluent.

4. A method for producing the antibody according to claim 1, comprising inoculating an animal with a polypeptide comprising SEQ ID NO:2 or an immunogenic fragment thereof under conditions in which said animal produces an antibody which specifically binds to said polypeptide, thereby producing said antibody.

5. The antibody according to claim 1 or claim 2 wherein said immunoglobulin fragment is a Fab, a F(ab'), or a F(ab')2.

6. The antibody according to claim 2 which is a chimeric antibody.

7. The antibody according to claim 2 which is a humanized monoclonal antibody.

8. The antibody or the immunoglobulin fragment thereof according to claim 1 which is antagonistic to the interaction between said polypeptide and its ligands.

9. A composition comprising the antibody or the immunoglobulin fragment thereof according to claim 8 in a pharmaceutical acceptable carrier or diluent.

* * * * *

UNITED STATES PATENT AND TRADEMARK OFFICE
CERTIFICATE OF CORRECTION

PATENT NO.         : 7,014,853 B2
APPLICATION NO. : 10/143618
DATED                 : March 21, 2006
INVENTOR(S)       : David J. Cosman It is certified that error appears in the above-identified patent and that said Letters Patent is hereby corrected as shown below:

Title page, Item (57) ABSTRACT, Line 2: after "superfamily" delete ","

Column 1, Line 57: change "Fcγ Rib1" to -- FcγRIIb1 --

Column 9, Line 41: change "one hour and the a" to -- one hour and then a --

Column 9, Line 53: change "16, 18 20" to -- 16, 18, 20 --

Column12, Line 8: change "recombinanat" to -- recombinant --

Column. 13, Line 23: change "one or amino acids" to -- one or more amino acids --

Column 16, Line 16: change "Preferably, a" to -- Preferably, --

Column 17, Line 30: change "recombinanat" to -- recombinant --

Column 17, Line 38: change "prokarytoic" to -- prokaryotic --

Column 18, Line 42: change "⁻ADH2" to -- ADH2 --

Column 18, Line 59: change "cline derived" to -- line derived --

Column 19, Line 53: change "my be" to -- may be--

Column 20, Line 22: change "will recognized the" to -- will recognize that --

Column 20, Line 30: change "describes a procedures" to -- describes a procedure --

Column 20, Line 42: change "application" to -- applications --

Column 21, Line 50: change "in any for" to -- in any form --

Column 23, Line 10: change "he antisense" to -- the antisense --

Column 27, Line 5: change "screen cells lines" to -- screen cell lines--

Column 28, Line 40: change "(amino acids 484-650." to -- (amino acids 484-650). --

Column 28, Line 52: change " describes" to -- described --

UNITED STATES PATENT AND TRADEMARK OFFICE
CERTIFICATE OF CORRECTION

PATENT NO.         : 7,014,853 B2
APPLICATION NO. : 10/143618
DATED              : March 21, 2006
INVENTOR(S)        : David J. Cosman It is certified that error appears in the above-identified patent and that said Letters Patent is hereby corrected as shown below:

Column 29, Line 37: change "removed" to -- remove --

Column 30, Line 19: change "immunization" to -- immunizations --

Column 31, Line 21: change "1 times" to -- 1 time --

Signed and Sealed this

Sixteenth Day of January, 2007

JON W. DUDAS
*Director of the United States Patent and Trademark Office*